(12) United States Patent
Lynch et al.

(10) Patent No.: US 11,098,307 B2
(45) Date of Patent: *Aug. 24, 2021

(54) COMPOSITIONS AND METHODS FOR RAPID AND DYNAMIC FLUX CONTROL USING SYNTHETIC METABOLIC VALVES

(71) Applicant: DUKE UNIVERSITY, Durham, NC (US)

(72) Inventors: Michael David Lynch, Durham, NC (US); Ashley Trahan, Hillsborough, NC (US); Daniel Rodriguez, Durham, NC (US); Zhixia Ye, Raleigh, NC (US); Charles Cooper, Durham, NC (US); Ahmet Bozdag, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/849,455

(22) Filed: Apr. 15, 2020

(65) Prior Publication Data

US 2020/0347388 A1 Nov. 5, 2020

Related U.S. Application Data

(62) Division of application No. 15/317,768, filed as application No. PCT/US2015/035306 on Jun. 11, 2015, now Pat. No. 10,662,426.

(60) Provisional application No. 62/010,574, filed on Jun. 11, 2014.

(51) Int. Cl.
| | | |
|---|---|---|
| C12N 15/63 | (2006.01) | |
| C12N 15/70 | (2006.01) | |
| C12N 15/11 | (2006.01) | |
| C12N 15/113 | (2010.01) | |

(52) U.S. Cl.
CPC ........ *C12N 15/111* (2013.01); *C12N 15/1137* (2013.01); *C12N 15/63* (2013.01); *C12N 15/70* (2013.01); *C12N 2310/14* (2013.01); *C12N 2320/50* (2013.01)

(58) Field of Classification Search
None
See application file for complete search history.

(56) References Cited

U.S. PATENT DOCUMENTS

| | | | |
|---|---|---|---|
| 8,916,358 B2 | 12/2014 | Swartz | |
| 10,036,001 B2 | 7/2018 | Swartz | |
| 10,662,426 B2* | 5/2020 | Lynch | C12N 15/63 |
| 2010/0297736 A1 | 11/2010 | Duhring et al. | |
| 2011/0125118 A1 | 5/2011 | Lynch | |
| 2011/0244575 A1 | 10/2011 | Lipscomb | |
| 2012/0052547 A1 | 3/2012 | Swartz | |
| 2012/0107892 A1 | 5/2012 | Agbogbo et al. | |
| 2012/0214170 A1 | 8/2012 | Moore | |
| 2015/0072399 A1 | 3/2015 | Lynch et al. | |
| 2017/0183688 A1* | 6/2017 | Bowie | C12Y 203/01012 |
| 2019/0390232 A1* | 12/2019 | Lynch | C12Y 106/03001 |
| 2020/0056211 A1* | 2/2020 | Lynch | C12N 9/0008 |
| 2020/0299687 A1* | 9/2020 | Lynch | C12P 7/18 |

FOREIGN PATENT DOCUMENTS

| | | |
|---|---|---|
| EP | 2562249 A1 | 2/2013 |
| EP | 2842542 A1 | 3/2015 |
| WO | 2001068883 A1 | 9/2001 |
| WO | 2003054140 | 2/2004 |
| WO | 2008141174 A2 | 11/2008 |
| WO | 2010141468 A1 | 12/2010 |
| WO | 2012129450 A1 | 9/2012 |
| WO | 2013176772 A1 | 11/2013 |
| WO | 2014160025 A2 | 10/2014 |
| WO | 2015191638 A1 | 12/2015 |
| WO | 2018156646 A1 | 8/2018 |

OTHER PUBLICATIONS

Ziemann et al. Gene name errors are widespread in the scientific literature. 2016. Geneome Biology. vol. 17, No. 177, 3 pages. (Year: 2016).*

Lynch et al., "Standarized two-stage bioprocess development using synthetic metabolic valves and dynamic metabolic control". Abstracts of Papers ; ACS National Meeting & Exposition; 249th National Meeting and Exposition of the American-Chemical-Society (ACS), vol. 249, p. BIOT418.

Brockman et al., "Dynamic knockdown of E. coli central metabolism for redirecting fluxes of primary metabolites", Metabolic Engineering, vol. 28., pp. 104-113.

Qi et al., "Repurposing CRISPR as an RNA-guided platform for sequence-specific control of gene expression," Cell (2013); vol. 152, pp. 1173-1183.

(Continued)

*Primary Examiner* — Channing S Mahatan
(74) *Attorney, Agent, or Firm* — Benesch, Friedlander, Coplan & Aronoff LLP

(57) ABSTRACT

This invention relates to metabolically engineered microorganisms, such as bacterial and or fungal strains, and bioprocesses utilizing such strains. These strains enable the dynamic control of metabolic pathways, which can be used to optimize production. Dynamic control over metabolism is accomplished via a combination of methodologies including but not limited to transcriptional silencing and controlled enzyme proteolysis. These microbial strains are utilized in a multi-stage bioprocess encompassing at least two stages, the first stage in which microorganisms are grown and metabolism can be optimized for microbial growth and at least one other stage in which growth can be slowed or stopped, and dynamic changes can be made to metabolism to improve the production of desired product, such as a chemical or fuel.

10 Claims, 15 Drawing Sheets

Specification includes a Sequence Listing.

(56) References Cited

OTHER PUBLICATIONS

Office Action issued in European patent application No. 15845669.9, dated Dec. 3, 2018, 6 pages.
Extended European search report issued in patent application No. 15845669.9, dated Jan. 3, 2018, 10 pages.
Yuki Soma et al.: "Metabolic flux redirection from a central metabolic pathway toward a synthetic pathway using a metabolic toggle switch", Metabolic Engineering, vol. 23, May 1, 2014, pp. 175-184.
Kathleen E. McGinness et al.: "Engineering Controllable Protein Degradation", Molecular Cell., vol. 22, No. 5, Jun. 1, 2006, pp. 701-707.
Levchenko Igor et al:"A specificity-enhancing factor for the ClpXP degradation machine", Science, vol. 289, No. 5488, Sep. 29, 2000, pp. 2354-2356.
UK Examination Report dated Apr. 1, 2019 from related UK Application No. GB1511937.3.
English Translation of Mar. 12, 2019 Office Action related to Japanese application JP2016-572578.
Kim et al., "A genetic strategy to identify targets for the development of drugs that prevent bacterial persistence", Proc. Natl. Acad. Sci USA (2013); vol. 110, p. 19095-19100.
Examination Report issued in European patent application No. 15845669.9 dated Sep. 26, 2019.
Torella, et al. Tailored fatty acid synthesis via dynamic control of fatty acid elongation. Proc Natl Acad Sci U S A. Jul. 9, 2013; 110(28): 11290-5. doi: 10.1073/pnas. 1307129110. Epub 2013.
International Preliminary Report on Patentability dated Dec. 15, 2016 from related International App. No. PCT/US2015035306.
UK Combined Examination and Search Report dated Dec. 8, 2016, from related UK Application No. GB1511937.3.
International Search Report and Written Opinion dated Apr. 27, 2016 from related International Application No. PCT/US2015/035306.
Fang, Shi-Ming et al., "A Practical Strategy to Discover New Antitumor Compounds by Activating Silent Metabolite Production in Fungi by Diethyl Sulphate Mutagenesis," Marine Drugs, vol. 12, pp. 1788-1814, 2014.
Imaizumi,A. et al., Improved production of L-lysine by disruption of stationary phase-specific rmf gene in *Escherchia coli*. Journal of Biotechnology, 117 (2005) 111-118.
Office Action issued in JP Application No. JP 2020-033434, dated Mar. 30, 2021.

* cited by examiner

COMPOSITIONS AND METHODS FOR RAPID AND DYNAMIC FLUX CONTROL USING SYNTHETIC METABOLIC VALVES

CROSS-REFERENCE TO RELATED APPLICATIONS

This application is a divisional of U.S. application Ser. No. 15/317,768 which is a § 371 U.S. National Stage of International Application PCT/US2015/035306, filed Jun. 11, 2015, which claims the benefit of U.S. Provisional Application No. 62/010,574, filed Jun. 11, 2014, the entire content of which are incorporated by reference herein in their entirety.

FEDERALLY SPONSORED RESEARCH OR DEVELOPMENT

This invention was made with government support under Federal Grant No. MCB-1445726 awarded by the National Science Foundation and Federal Contract No. HR0011-14-C-0075 awarded by the Defense Advanced Research Projects Agency of the United States Department of Defense. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "OLG Ref 210-44_ST25.txt". The sequence listing is 184,352 bytes in size, and was created on Jun. 11, 2015. It is hereby incorporated by reference in its entirety.

FIELD OF THE INVENTION

This invention relates to metabolically engineered microorganisms, such as bacterial and or fungal strains, and bioprocesses utilizing such strains. These strains enable the dynamic control of metabolic pathways.

BACKGROUND OF THE INVENTION

Petroleum is the primary feedstock, not only for the fuels we use, but the majority of the chemicals we consume as well. The chemical industry is heavily reliant on this non-renewable resource. Replacement of petroleum with renewable feedstocks ensures longer-term viability and environmental sustainability. Novel fermentation based processes to make chemicals have been a contributing technology, enabling the change to renewable feedstocks (Werpy & Peterson, Top Value Added Chemicals from Biomass. Volume I—Results of Screening for Potential Candidates from Sugars and Synthesis Gas., Yixiang et al. "Green" Chemicals from Renewable Agricultural Biomass—A Mini Review. The Open Agriculture Journal, 2008). These fermentation processes have made rapid advancements in recent years due to technology developments in the fields of fermentation science, synthetic biology, as well as metabolic and enzyme engineering (Jarboe, L. R., et al., Metabolic engineering for production of biorenewable fuels and chemicals: contributions of synthetic biology. J Biomed Biotechnol, 2010, Lee, J. W., et al., Systems metabolic engineering of microorganisms for natural and non-natural chemicals. Nat Chem Biol, 2012). Despite these substantial advances, most successful examples of rationale directed engineering approaches have also greatly relied on numerous cycles of trial and error. The field of metabolic engineering has historically been limited in predicting the behavior of complex biological systems in-vivo, from simplified models and basic in-vitro biochemical principles. Such rational approaches have required significant a priori knowledge of microbial physiology that in many cases is incomplete. This is particularly true for complex phenotypes that require an intricate balance between the activities of many seemingly unrelated gene products. In many cases it has proven much more difficult than expected to integrate a possibly well characterized production pathway into a living host and balance the complex requirements of both biomass growth and production.

One solution is the development of platform microbial strains that utilize synthetic metabolic valves (SMVs) that can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

A simplified two-stage bioprocess using synthetic metabolic valves is depicted in FIG. 1, strains are grown in a minimal media with a single limiting nutrient such as inorganic phosphate. During this growth phase cells are not producing any product other than biomass and as a result are not subject to any possible toxic or unwanted side effects of product formation. Biomass growth and yield can be optimized. As the limiting nutrient is depleted, cell growth is stopped. Simultaneously, these strains will be engineered to contain synthetic metabolic valves, which silence genes and enzymes essential for growth and redirect carbon, electrons and energy to any molecule of interest. This process utilizes a novel combination of a two-stage production and concurrent metabolic engineering strategy.

There is significant precedent in the biotechnology industry for using and scaling two stage processes similar to that described in FIG. 1. Many similar processes are routinely used for the heterologous expression of proteins. In these standard processes cells are grown to a productive or "primed" state for protein synthesis (such as mid-exponential phase in E. coli) and then induced to express a heterologous protein. In many cases, the diversion of cellular amino acids and energy to the heterologous protein has a significant effect on, if not halting, cellular growth. It is not surprising that these types of processes have not been developed for the biological production of small molecules as historically most successful efforts to metabolically engineer the production of small molecules have leveraged the power of anaerobic metabolism to couple product formation with growth.

Anaerobic growth-coupled product formation enables the use of powerful growth based selections to identify better producers. The faster the cells grow the more product they make. This has allowed for the classical selection of industrial strains for many natural products such as ethanol and isobutanol. However, the requirement for anaerobic production greatly limits the number and variety of different molecules or products that can be made using synthetic biology. Numerous products would require aerobic metabolism to supply the needed energy and cofactors to allow for a thermodynamically feasible metabolic pathway. In these cases a generic and robust aerobic production platform would greatly simplify the optimization and scale up of a diverse number of products. A controlled multi-stage process, enabled by synthetic metabolic valves, supplies such a platform.

Synthetic metabolic valves enable synthetic biologists and metabolic engineers the ability to decouple the complex metabolic and thermodynamic needs of growth from those of product formation. This decoupling also enables the removal of growth based regulatory mechanisms that may inhibit product formation and allows for the silencing of essential metabolic pathways that may detract from or interfere with production. These essential interfering metabolic pathways could include amino acid biosynthesis or the citric acid cycle as well as the biosynthesis of many secondary metabolites, and those pathways involved in maintaining intracellular redox and energy balances. These pathways have traditionally been off limits to many metabolic engineering strategies, as attempts at manipulation have led to growth defects.

SUMMARY OF THE INVENTION

According to one embodiment, the invention is directed to methods to construct controllable synthetic metabolic valves. In certain of these embodiments synthetic metabolic valves are used to controllably reduce or eliminate flux through one more metabolic pathways. In further embodiments, flux is reduced or eliminated through one or more metabolic pathways whose enzymes are essential for microbial growth in a given environment. In other embodiments, the invention is related to genetically modified microorganisms that utilize one or more synthetic metabolic valves thereby enabling dynamic control over metabolic pathways. Other embodiments of the invention are directed to multistage bioprocesses that utilize genetically modified microorganism that in turn utilize one or more synthetic metabolic valves that enable dynamic flux control. Still in other embodiments of the invention, the transitions between stages in multistage bioprocesses using genetically modified microorganisms are controlled by the addition of chemical inducers or by the control of key nutrient levels. Additional genetic modifications may be added to a microorganism to enable the conversion of carbon feedstocks to chemical or fuel products. In certain embodiments, carbon feedstocks can include, but are not limited to the sugars: glucose, sucrose xylose, arabinose, mannose, lactose, or alternatively carbon dioxide, carbon monoxide, methane, methanol, formaldehyde, or oils. In addition, genetic modifications to produce chemical or fuel products from various carbon feedstocks can include metabolic pathways utilizing, but not limited to, the central metabolites acetyl-CoA, malonyl-CoA, pyruvate, oxaloacetate, erthyrose-4-phosphate, xylulose-5-phosphate, alpha-ketoglutarate and citrate. Products that can be derived from these central metabolites include but are not limited to acetate, alcohols (ethanol, butanol, hexanol, and longer n-alcohols), organic acids (3-hydroxy-prpionic acid, lactic acid, itaconic acid), amino acids (alanine, serine, valine), fatty acids and their derivatives (fatty acid methyl esters (FAMEs), fatty aldehydes, alkenes, alkanes) and isoprenoids.

In various embodiments, the increased production of acetate from acetyl-phosphate may occur via the increased expression of an acetate kinase. A non-limiting example is the acetate kinase from E. coli encoded by the ackA gene. Increased expression of an acetate kinase may optionally be combined with genetic modifications that result decreased activity phosphoacetyltransferase such as that encoded by the pta gene of E. coli.

In various embodiments, the increased production of ethanol from acetyl-CoA may occur via the increased expression of an oxygen tolerant ethanol dehydrogenase, such as the enzyme from E. coli encoded by the adhE gene with a mutation Glu568Lys as taught by Dellomonaco et al, AEM. August 2010, Vol. 76, No. 15, p 5067. and Holland-Staley et al. JBACs. November 2000, Vol. 182, No. 21, p 6049.

In various embodiments, the increased production of butyrate from acetyl-CoA may occur via the increased expression of butyrate pathway enzymes including an acetoacetyl-CoA thiolase, crotonase, crotonyl-CoA reductase, butyrate phospho-transferase and butyrate kinase as taught by Fischer et al, Appl Microbiol Biotechnol. 2010, September, Vol. 88, No. 1, p. 265-275. Alternatively, increased butyrate may be accomplished via the increased expression of butyrate pathway enzymes including an acetoacetyl-CoA synthase, crotonase, crotonyl-CoA reductase and butyryl-CoA thioesterase as taught by PCT/US2012/030209.

In various embodiments, the increased production of n-butanol from acetyl-CoA may occur via the increased expression of n-butanol pathway enzymes including an acetoacetyl-CoA thiolase, crotonase, crotonyl-CoA reductase, butyryl-CoA reductase and butyraldehyde reductase as taught by Atsumi et al, Metabolic Engineering. 2008. November, Vol. 10, No. 6, p. 305).

In various embodiments, the increased production of fatty acids of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, and a acyl-CoA thioesterase as taught by PCT/US2012/030209.

In various embodiments, the increased production of fatty acid methyl esters from acetyl-CoA may occur via the increased expression of fatty acid methyl ester synthesis pathway enzymes including an ketoacetyl-CoA synthase, 3-hydroxyacyl-CoA dehydratase, an enoyl-CoA reductase, and a acyl-CoA wax ester synthase as taught by: PCT/US2012/030209 and US 20110146142 A1.

In various embodiments, the increased production of n-hexanol from acetyl-CoA may occur via the increased expression of a fatty acid synthesis pathway enzymes including an ketoacetyl-CoA thiolases, 3-hydroxyacyl-CoA dehydratase, an enoyl-CoA reductase, and a acyl-CoA thioesterase as taught by Dekishima et al. J Am Chem Soc. 2011. August. Vol. 133, No. 30, p. 1139.

In various embodiments, the increased production of n-alcohols of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, as taught by PCT/US2012/030209 and a fatty acyl-CoA reductase and fatty aldehyde reductase as taught by Yan-Ning Zheng et al. Microbial Cell Factories. 2012. Vol. 11:65.

In various embodiments, the increased production of n-alkenes can be accomplished by first producing n-alcohols as described elsewhere followed by the chemical dehydration of the n-alcohol to an n-alkene by catalytic methods well known in the art.

In various embodiments, the increased production of n-alkanes can be accomplished by first producing fatty acids as described elsewhere followed by the chemical decarboxylation of the n-alcohol to an alkane by catalytic methods well known in the art.

In various embodiments, the increased production of isoprene from acetyl-CoA may occur via the increased expression of pathway enzymes including an acetoacetyl-CoA thiolase, hydroxymethylglutaryl-CoA synthase, hydroxymethylglutaryl-CoA reductase, mevalonate kinase, phosphomevalonate kinase, mevalonte diphosphate decarboxylase, isopentenyl-diphosphate isomerase and isoprene synthase as taught by US 20120276603 A1.

In various embodiments, the increased production of a product from acetyl-CoA may occur via both the increased expression of an acetyl-CoA carboxylase enzyme which can convert acetyl-CoA into malonyl-CoA and the increased expression of a production pathway comprising multiple pathway enzymes which can convert malonyl-CoA further to a product.

In various embodiments, the increased production of a product from malonyl-CoA may occur via both the increased activity of an acetyl-CoA carboxylase enzyme which can caused by mutation of one or more fatty acid synthesis enzymes such as is taught by PCT/US2012/030209, PCT/US2011/0222790 and 3. UK Patent GB2473755 and the increased expression of a production pathway comprising multiple pathway enzymes which can convert malonyl-CoA further to a product.

Within the scope of the invention are genetically modified microorganism, wherein the microorganism is capable of producing an acetyl-CoA derived product at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

Within the scope of the invention are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
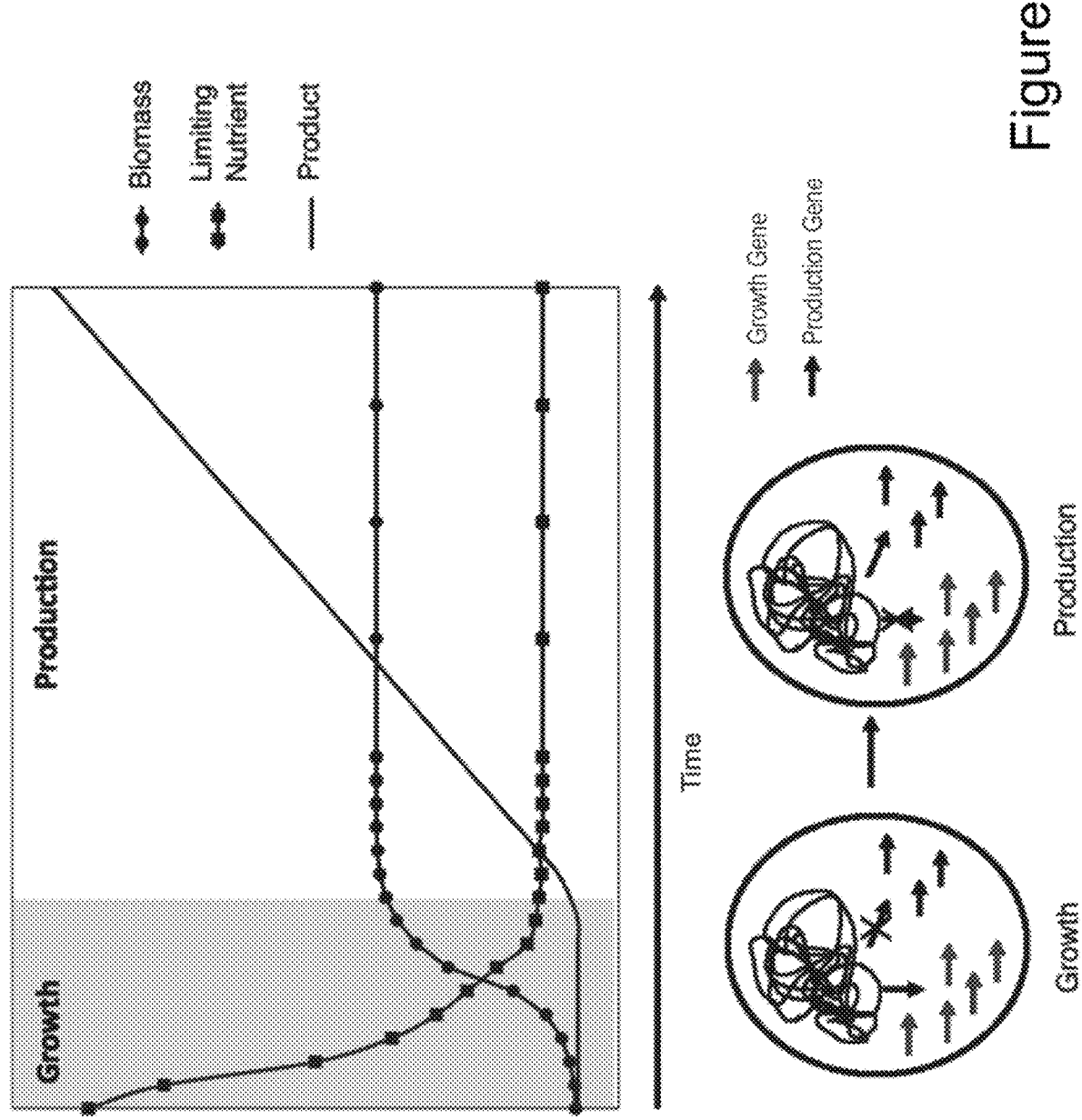
FIG. 1 depicts an overview of a two-phase fermentation processes utilizing a microbe with synthetic metabolic valves. Top Panel: Overview of the fermentation process. Biomass is grown in minimal media with a single limiting macronutrient, such as inorganic phosphate. As the biomass level (black line) or number of cells increases the limiting nutrient (red line) is depleted. When the limiting nutrient is completely consumed, biomass growth is halted. Simultaneously the limitation induces metabolic changes to initiate product biosynthesis through engineered synthetic valves. Lower Panel: Metabolic Changes in the Two Phase Process. In correlation with the system level changes, metabolic changes are induced upon depletion of the limiting nutrient. Specifically, genes encoding metabolic pathways essential for cellular growth "growth genes" are active in the growth phase while genes encoding product biosynthesis "product genes" are silenced. Upon entry into the production phase triggered by nutrient depletion, "growth genes" are silenced and "product genes" are activated.

The present invention is related to various production methods and/or genetically modified microorganisms that have utility for fermentative production of various chemical products, to methods of making such chemical products that utilize populations of these microorganisms in vessels, and to systems for chemical production that employ these microorganisms and methods. Among the benefits of the present invention is the increased ability to reduce or eliminate metabolic pathways required for microbial growth that may interfere with production.

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, *Enzyme Nomenclature*, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as an nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Prophetic examples provided herein are meant to be broadly exemplary and not limiting in any way.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

More particularly, based on the various criteria described herein, suitable microbial hosts for the bio-production of a chemical product generally may include, but are not limited to the organisms described in the Common Methods Section III. Media and Culture Conditions In addition to an appropriate carbon source, such as selected from one of the herein-disclosed types, bio-production media must contain suitable minerals, salts, cofactors, buffers and other components, known to those skilled in the art, suitable for the growth of the cultures and promotion of the enzymatic pathway necessary for chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The following published resources are incorporated by reference herein for their respective teachings to indicate the level of skill in these relevant arts, and as needed to support a disclosure that teaches how to make and use methods of industrial bio-production of chemical product(s) produced under the invention, from sugar sources, and also industrial systems that may be used to achieve such conversion with any of the recombinant microorganisms of the present invention (Biochemical Engineering Fundamentals, $2^{nd}$ Ed. J. E. Bailey and D. F. Ollis, McGraw Hill, New York, 1986, entire book for purposes indicated and Chapter 9, pages 533-657 in particular for biological reactor design; Unit Operations of Chemical Engineering, $5^{th}$ Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli,* under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf, gltA, ppc, udhA, lpd, sucD, aceA, pfkA, lon, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutyrate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI. Synthetic Metabolic Valves

Figure 2:
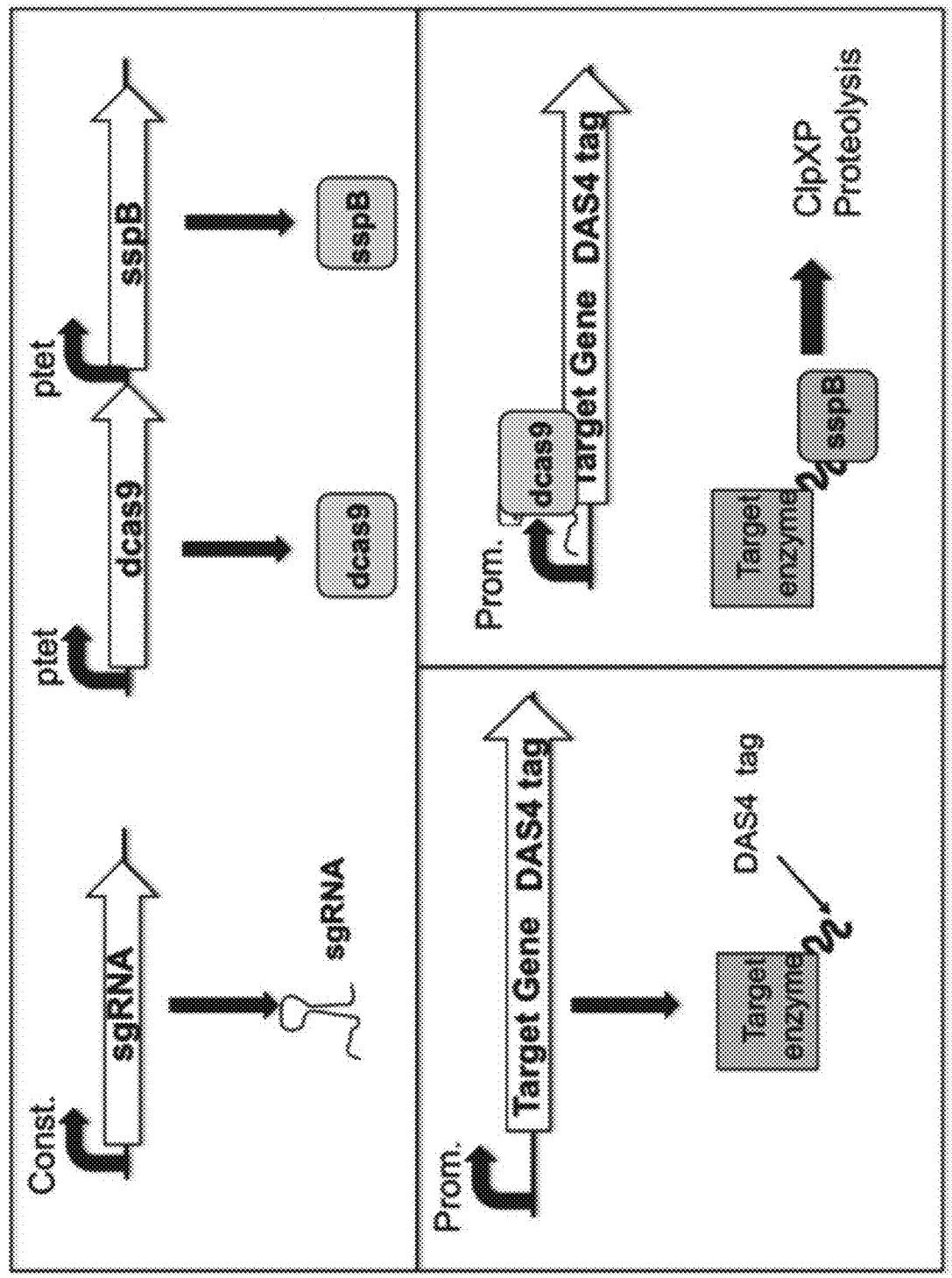
FIG. 2 depicts an overview of a synthetic metabolic valve in *E. coli* using a combination of CRISPR interference gene silencing and controlled protein degradation. Upper Panel: (LEFT) Constructs are made to express small guide RNAs to target a gene of interest in addition to (RIGHT) the controlled induction of a cascade protein complex such as catalytically inactive Cas9 or dCas9 as well as the controlled induction of the chaperone (clpXP enhancing factor) sspB. Expression can be controlled such as by the controlled ptet promoter induced by aTc. The constructs produce dCas9 and sspB proteins in addition to a targeting sgRNA. Bottom Panel: (LEFT) The target gene/protein contains a C-terminal DAS4 tag for binding to sspB. (RIGHT) When expression is induced, dCas9 is targeted to the gene of interest by the targeting sgRNA thereby silencing transcription. Concurrently, the expression of sspB results in the binding of sspB to the DAS4 C-terminal tag of protein that has already been translated. The sspB/DAS4 complex is then targeted for degradation by the clpXP protease.
Figure 3:
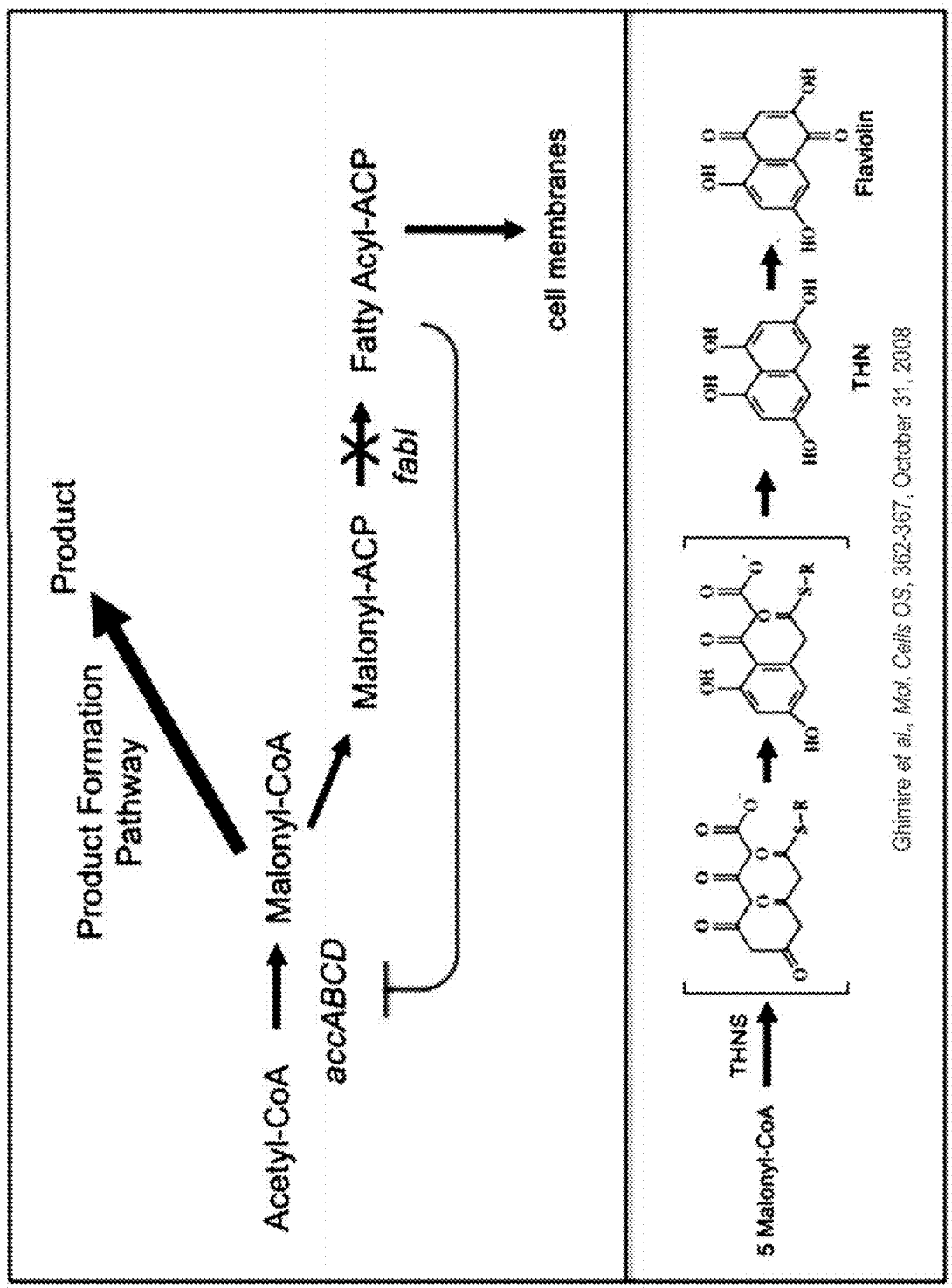
FIG. 3 depicts the production of tetrahydroxynapthalene (THN) by redirecting flux from malonyl-CoA. Upper Panel: An overview of redirecting flux from growth to product by controlling fabI (enoyl-coA reductase levels) in E. coli. In E. coli, the primary fate of the intermediate malonyl-CoA is to provide precursors for fatty acid synthesis. The key enzyme controlling the rate of lipid synthesis, acetyl-CoA carboxylase, encoded by the accABCD genes, is strongly inhibited by the fatty acid production intermediates, fatty acyl-ACPs. Removal of fabI leads to a decrease in acyl-ACP pools and a reduction in inhibition of acetyl-CoA carboxylase allowing malonyl-CoA levels to accumulate and be used for product synthesis. The removal of fabI limits lipid production and halts growth. Lowe Panel: One potential product from malonyl-CoA is tetrahydroxynapthalene (THN). THN is produced from 5 molecules of malonyl-CoA via the polyketide synthase, THN synthase encoded by the rppA gene of S. coelicolor.

In particular the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis. An example of the combination of CRISPR interference based gene silencing and controlled proteolysis is illustrated in FIG. 2.

VI.A Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67(4) p657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p1173-1183. DOI: 10.1016/j.cell.2013.02.022. In addition, methodologies and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular the invention describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22(5) p701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example Schmidt et al, "ClpS is the recognition component for *Escherichia coli* substrates of the N-end rule degradation pathway" Molecular Microbiology March 2009. 72(2), 506-517. doi:10.1111, teaches that an N-terminal sequence can be added to a protein of interest in enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to help enable the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in *Saccharomyces cerevisiae*" Molecular Systems Biology 3, Article 127. doi:10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

VII. Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.) These published resources are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls. Subject matter in the Examples is incorporated into this section to the extent not already present.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology and biochemistry.

The names and city addresses of major suppliers are provided herein.

Example 1

Dynamic Flux Control Using Temperature Sensitive Enzymes to Improve Malonyl-CoA Flux in *E. coli*

Figure 4:
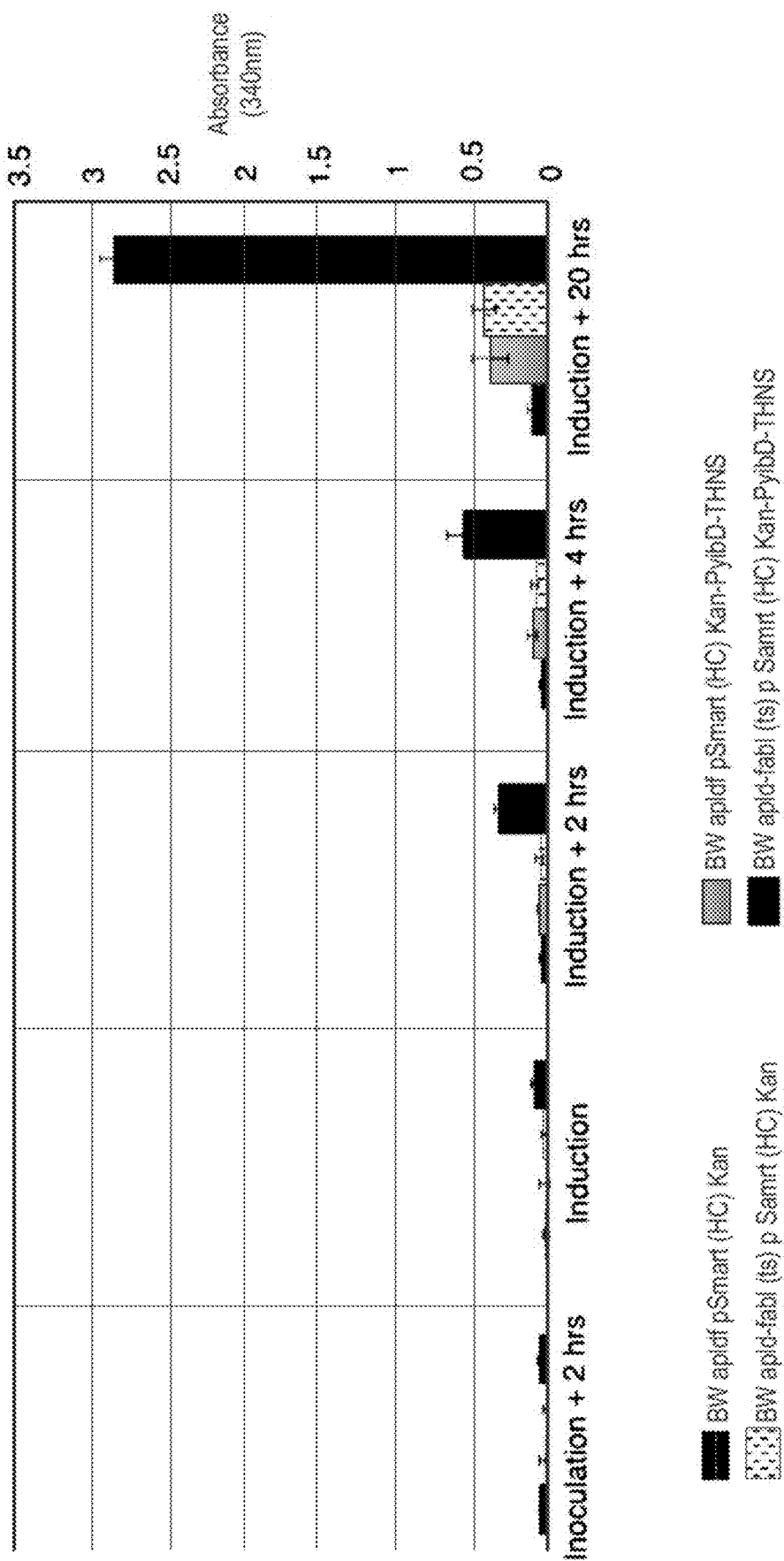
FIG. 4 depicts increased production of tetrahydroxynapthalene from malonyl-CoA in a two stage process as a result of the controlled inactivation of a temperature sensitive fabI allele. Improved production of THN by redirecting malonyl-CoA flux, using a temperature controlled process to inactivate a temperature sensitive allele of fabI. Strains as listed BWalpdf (BW25113: ΔldhA, ΔpflB, ΔpoxB, ΔackA-pta, ΔadhE), BWalpdf-fabI(ts) (BW25113: ΔldhA, ΔpflB, ΔpoxB, ΔackA-pta, ΔadhE, fabI(F241S), gentR). Plasmids are i) pSMART-HC-Kan-yibD-THNS and ii) pSMART-HC-Kan (control).

This example describes the increased production of tetrahydroxynaphtalene (THN) in *E. coli* from the intermediate malonyl-CoA using the controlled inactivation of fabI via a temperature sensitive allele. Briefly, strain BWapldf (BW25113:ΔldhA, ΔpflB, ΔpoxB, ΔackA-pta, ΔadhE) was further genetically modified so that the fabI gene was mutated to contain both a temperature sensitive (ts) mutation (F241S) as well as to incorporate gentamicin resistance cassette a the C-terminus of the fabI gene. This was accomplished using standard recombineering protocols. The strain was further modified to express the tetrahydroxynapthalene (THN) synthase gene (rppA from *Steptomyces coelicolor*) under phosphate limiting conditions by transformation with the plasmid pSMART-HC-Kan-yibD-THNS (SEQ ID NO:1). Control strains were made with a control empty vector pSMART-HC-Kan (Genbank Accession #AF532107.1), obtained from Lucigen. This high copy plasmid conferring kanamycin resistance was constructed using routine molecular biology methods utilizing the pSMART-HC-Kan kit obtained from Lucigen. The rppA gene under the control of the promoter of low phosphate induced yibD(waaH) gene of *E. coli*. This strain, as well as controls, were evaluated for THN production using the two-stage protocol as outline in the Common Methods section "Shake Flask Protocol-1". Relative THN production was quantified by measuring the absorbance of the supernatant at 340 nm. FIG. 4 summarizes the results.

Example 2

A Synthetic Metabolic Valve to Improve Malonyl-CoA Flux in *E. coli*

Figure 5:
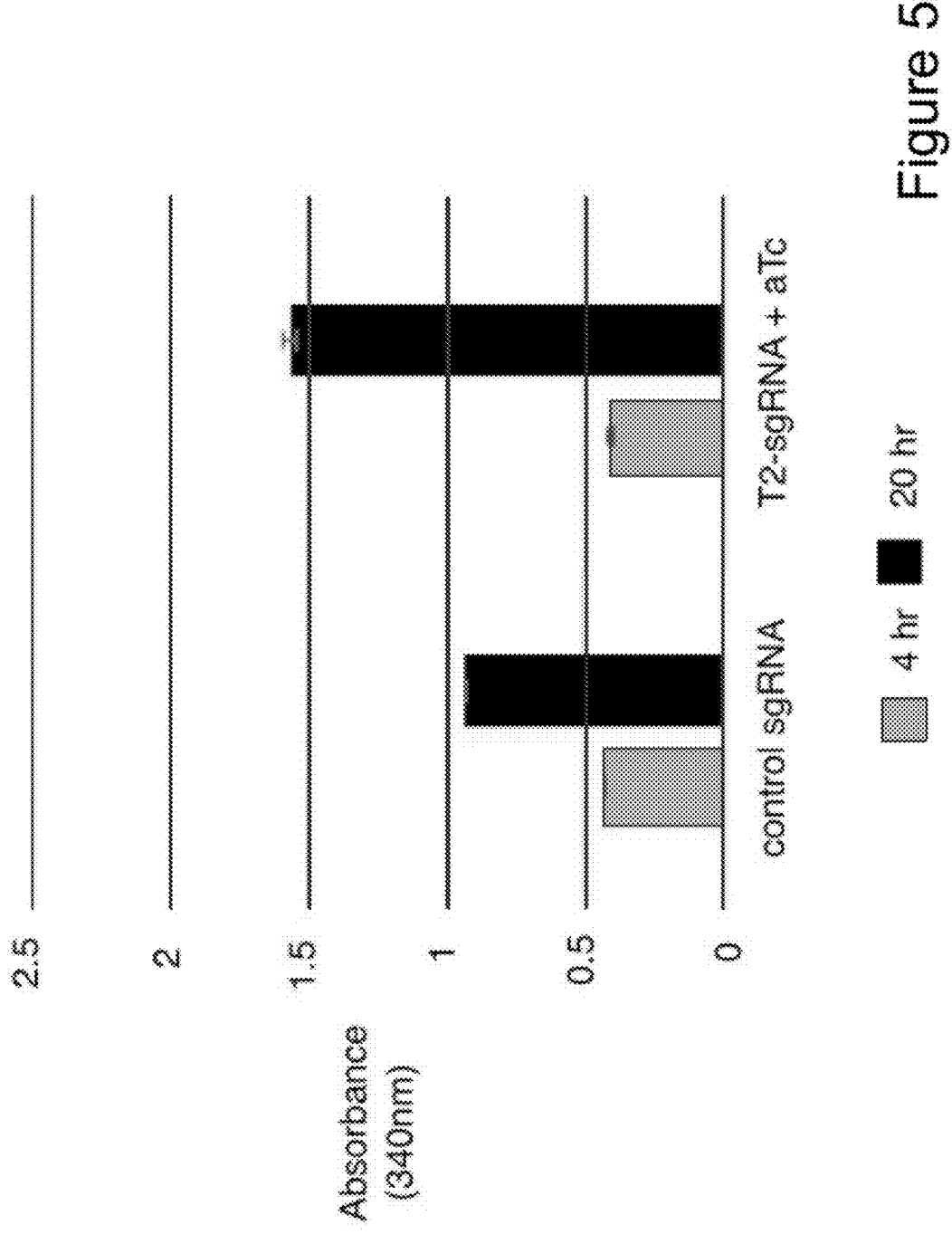
FIG. 5 depicts increased production of tetrahydroxynapthalene from malonyl-CoA in a two stage process as a result of a combination of controlled protein degradation and gene silencing. Improved production of THN by redirecting malonyl-CoA flux, using a synthetic metabolic vlae comprising a combination of CRISPR interference gene silencing and controlled proteolysis as outlined in FIG. 2. THN production at 4 hrs and 20 hrs is compared for two strains. LEFT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-control lacking a targeting sgRNA. RIGHT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-T2-fabIsgRNA expressing a sgRNA targeting fabI.

This example describes the increased production of tetrahydroxynaphtalene (THN) in *E. coli* from the intermediate malonyl-CoA using the controlled repression of fabI using synthetic metabolic valve technology. In this example a combination of CRISPR interference gene silencing technology and controlled protein degradation was used in a two-stage process. Briefly, strain BWapldf (BW25113: ΔldhA, ΔpflB, ΔpoxB, ΔackA-pta, ΔadhE) was further genetically modified so that the fabI gene was tagged to contain a C-terminal DAS4 tag as well as to incorporate gentamicin resistance cassette a the C-terminus of the fabI gene. The C-terminal nucleotide sequence encoding the DAS4 tag was integrated as the following sequence: 5'-GCGGCCAACGATGAAAACTATTCTGAAAAC-TATGCGGATGCGTCT-34 (SEQ ID NO: 48). This was accomplished using standard recombineering protocols. In addition, the strain was further modified so as to delete the sspB gene. This was also performed with standard recombineering methods. In addition, these strains were still further modified to contain three plasmids, the first plasmid expresses the tetrahydroxynapthalene (THN) synthase gene, pSMART-HC-Kan-yibD-THNS (SEQ ID NO:1), as described above. The second plasmid was constructed to express a small guide RNA targeting the fabI gene from a high copy spectinomycin resistance plasmid derived from pCDF-1b, which was obtained from EMD Millipore Biosciences. The plasmid, pCDF-T2-fabIsgRNA (SEQ ID NO:2), expresses a small guide RNA to use with *S. pyogenes* dCas9. The specific fabI T2 targeting sequence is given by 5'-CAGCCTGCTCCGGTCGGACCG-3' (SEQ ID NO:47). A control plasmid was also made missing any targeting sequence as described by Qi et al. Cell February 2013; 152(5) p 1173-1183. DOI: 10.1016/j.cell.2013.02.022. The last plasmid, pdCas9-ptet-sspB (SEQ ID NO:3), was derived from the plasmid pdCas9-bacteria, from Qi et al, which was obtained from Addgene (Cambridge, Mass. 02139; Plasmid ID 44249). Briefly, pdCas9-bacteria was linearized and the sspB gene was introduced under the control of an additional ptet promoter at the 3' of the catalytically inactive dcas9 gene. The addition of anhydrotetracycline (aTc) will induce expression of both dCas9 as well as sspB from this Chloramphenicol resistance conferring plasmid. All plasmids were constructed using standard molecular biology methods and sequences confirmed by DNA sequencing. These strains, as well as controls, were evaluated for THN production using the two-stage protocol as outline in the Common Methods section "Shake Flask Protocol-2". Relative THN production was quantified by measuring the absorbance of the supernatant at 340 nm. FIG. 5 summarizes the results.

Example 3

General Example

Numerous microbial strains, such as any of the strains listed in the Common Methods Section, may be genetically modified to express enzymes for the biosynthesis of a product. In addition these modified microbial strains can be further modified to contain a controllable synthetic metabolic valve for the dynamic reduction in enzyme activity of one or more metabolic pathways including those required for growth. These valves may utilize one or a combination of methods including gene silencing and controlled proteolysis. Further these modified strains may be used in a multistage fermentation process wherein transition between stages is concurrent with controlled activation of these valves. Specifically, any of these microbial strains may also be further engineered to express a heterologous production pathway enabling the product formation.

Example 4

*E. coli* Host Strain Construction

Briefly, strain BWapldf (BW25113:ΔldhA, ΔpflB, ΔpoxB, ΔackA-pta, ΔadhE) was further genetically modified for the deletion of the following genes: arcA, iclR and sspB, to construct strain DLF_0002. This was also performed with standard scarless recombineering methods. To construct a strain capable of both crispr based gene silencing using the native CASCADE system in *E. coli* as well as controlled proteolysis, the cas3 gene of *E. coli* was first deleted. This gene was replaced with a sequence to enable both constitutive expression of the casABCDE-cas1,2 operon enabling CASCADE based gene silencing, as well as a construct allowing for the low phosphate induction of the sspB chaperone. The DNA sequence integrated was ordered as a single synthetic construct: SEQ ID NO:4, and integrated using standard recombineering methodologies. In the place of the cas3 gene, this construct integrates a transcriptional terminator, followed by the low phosphate inducible *E. coli* ugpB gene promoter and the sspB gene. The sspB gene is followed by another transcriptional terminator and a subsequent constitutive proB promoter adapted from (Davis, J H., Rubin, A J., and Sauer, R T. NAR. February 2011; 39(3) p 131-1141. DOI: 10.1093) to drive constant expression of the CASCADE operon. The resulting strain is termed DLF_0025.

A derivative of *E. coli* strain DLF 0025 was constructed to utilize a non-PTS dependent glucose uptake system. PTS (phosphotransferase system) based sugar uptake is well known in the art and links the phosphorylation of glucose to the production of pyruvate. Alternative uptake has been previously described in *E. coli*, (Hernandez-Montalvo, V., et al., Biotechnol Bioeng. September 2003; 83(6) p687-694.), and relies on the overexpression of the *E. coli* galP permease and glucokinase (glk gene) along with the deletion of the *E. coli* ptsG gene. The ptsG gene was deleted and replaced with a constitutively expressed glucokinase construct, this construct was ordered as a single synthetic linear DNA construct (SEQ ID NO:5) and integrated according to standard methodologies. In addition, the galP promoter was also replaced via chromosomal replacement using another single synthetic linear DNA construct (SEQ ID NO:6), the resulting strain was called DLF_0286. In both cases the proC promoter was used to drive constitutive expression (Davis, J H., Rubin, A J., and Sauer, R T. NAR. February 2011; 39(3) p 1131-1141. DOI: 10.1093).

*E. coli* strains DLF_0025 and DLF_0286 were further modified for the controlled proteolysis of key enzymes in central metabolism including: 1) enoyl-ACP reductase encoded by the fabI gene, involved in fatty acid biosynthesis, 2) citrate synthase encoded by the gltA gene, involved in citric acid cycle, 3) soluble transhydrogenase encoded by the udhA gene, involved in NADPH metabolism, 4) glucose-6-phosphate-1-dehydrogenase encoded by the zwf gene, involved in the pentose phosphate pathway and 5) the lipoamide dehydrogenase or E3 component of the pyruvate dehydrogenase complex encoded by lpd gene. C-terminal DAS+4 tags enabling sspB controlled proteolysis were integrated at the 3' end of each of the above genes as the following sequence: 5'-GCGGCCAACGATGAAAACTAT-TCTGAAAACTATGCGGATGCGTCT-3' (SEQ ID NO:48). This was accomplished by the insertion of single DNA cassettes containing the DAS4 tags, targeting sequences as well as a downstream antibiotic resistance cassette. The fabI-DAS4 tag and lpd-DAS4 tag were followed by a gentamicin resistance cassette, the gltA-DAS4 tag was followed by a zeocin resistance cassette, and the udhA-DAS4 and zwf-DAS4 tags were both followed by a blasticidin resistance cassette. The integrated sequences used for the C-terminal tagging fabI, lpd, gltA, udhA and zwf are SEQ ID NO:7, SEQ ID NO:8, SEQ ID NO:9 SEQ ID NO:10 and SEQ ID NO:11 respectively. Strains with single and combinations of DAS4 tagged enzymes were constructed. Host strain genotypes are listed in Table 1.

TABLE 1

*E. coli* Host Strains

| Strain ID | Genotype |
|---|---|
| BW25113 | F-, λ⁻, Δ(araD-araB)567, ΔlacZ4787(::rrnB-3), rph-1, Δ(rhaD-rhaB)568, hsdR514 |
| BWapldf | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt |
| DLF_0002 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB |
| DLF_0025 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB |
| DLF_0286 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP |
| DLF_0043 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS+4:zeoR |
| DLF_0028 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR |
| DLF_0031 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR |
| DLF_0038 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflBxfrt, ΔackA-pta::frt, ΔadhE::frt, ΔiclR, ΔarcA, ΔsspB, Δcas3::ugpBp-sspB-proB, fabI-DAS+4:gentR, udhA-DAS+4:bsdR |
| DLF_0040 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR zwf-DAS+4:bsdR |
| DLF_0039 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, gltA-DAS+4:zeoR |
| DLF_0047 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR, gltA-DAS+4:zeoR, udhA-DAS+4:bsdR |
| DLF_0167 | F-, λ⁻, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS+4:gentR gltA-DAS+4:zeoR zwf-DAS+4:bsdR |

TABLE 1-continued

E. coli Host Strains

| Strain ID | Genotype |
|---|---|
| DLF_0041 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, |
| DLF_0165 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, zwf-DAS+4:bsdR |
| DLF_0042 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, udhA-DAS+ 4:bsdR |
| DLF_0049 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, udhA-DAS+4:bsdR |
| DLF_0048 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4:gentR, gltA-DAS+4:zeoR, zwf-DAS+4:bsdR |
| DLF_0045 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflBxfrt, ΔackA-pta::frt, ΔadhE::frt, ΔiclR, ΔarcA, ΔsspB, Δcas3::ugpBp-sspB-proB, gltA-DAS+4:zeoR, udhA-DAS+4:bsdR |
| DLF_0044 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS+4:zeoR, zwf-DAS+4:bsdR |
| DLF_0287 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR |
| DLF_0288 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, zwf-DAS+4:bsdR |
| DLF_0289 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, udhA-DAS+4:bsdR |
| DLF_0290 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflBxfrt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, zwf-DAS+4:bsdR, fabI-DAS+4:gentR |
| DLF_0291 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS+4:zeoR, udhA-DAS+4:bsdR, fabI-DAS+4:gentR |

Example 5

Low Phosphate Gene Expression in E. coli

Figure 6:
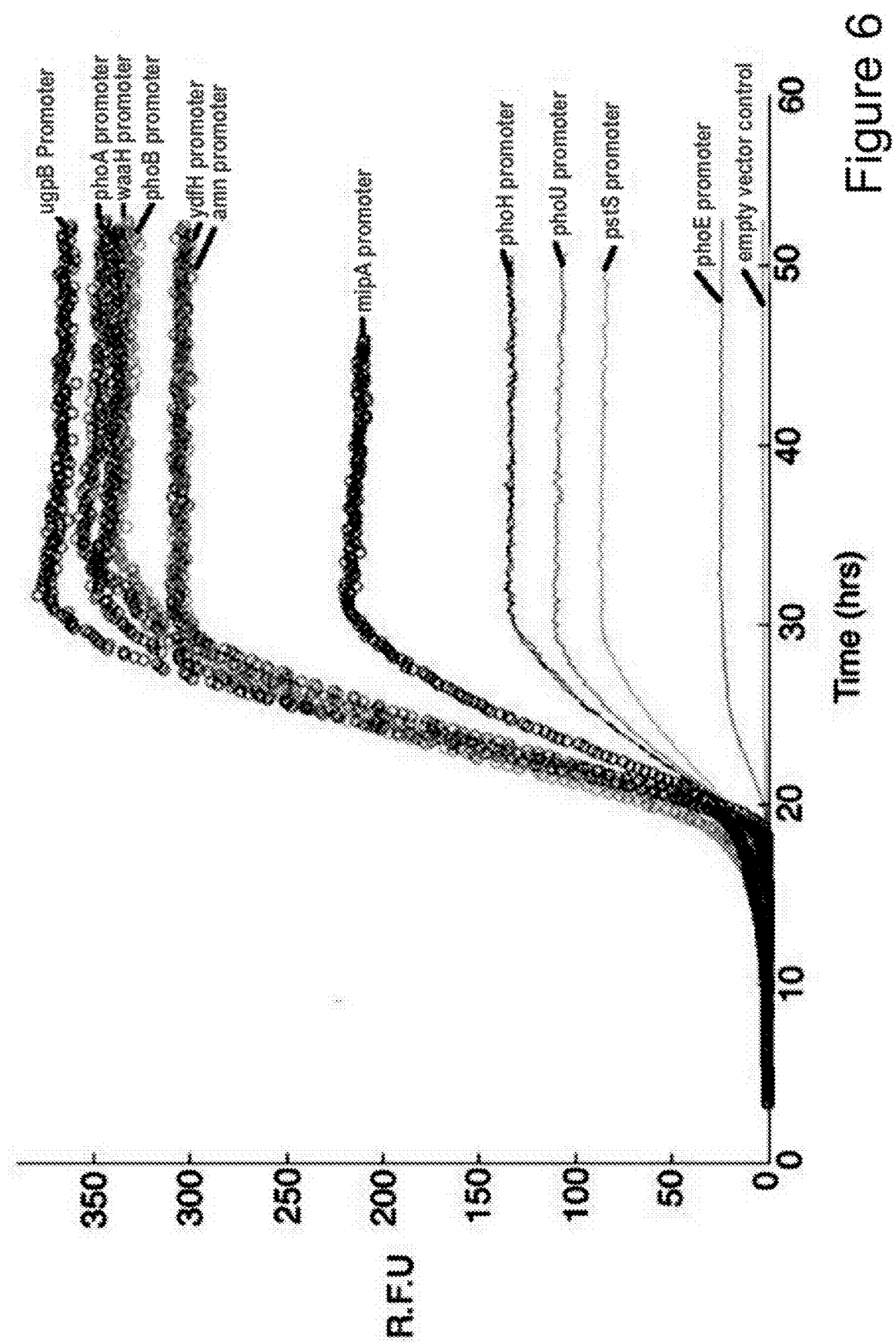
FIG. 6 depicts the low phosphate induction of a GFP reporter with various low phosphate inducible promoters. A comparison of the low phosphate inducible expression for the following gene promoters: amn, phoA, phoB, phoE, phoH, phoU, mipA, pstS, ugpB, waaH and ydfH, is shown. An ultraviolet excitable, green fluorescent protein (GFPuv) reporter gene was used and relative fluorescence units (RFU) are plotted as a function of time. Growth stops and phosphate depletion begins at about 15-20 hrs.

In order to evaluate different low phosphate induction schemes to control synthetic metabolic valves, several known low phosphate inducible promoters form E. coli were evaluated with a ultraviolet excitable, green fluorescent protein (GFPuv) reporter gene. These gene promoters included those for the following genes: amn, phoA, phoB, phoE, phoH, phoU, mipA, pstS, ugpB, waaH and ydfH, were evaluated for low phosphate induction. Reporter plasmids linking each promoter to a GFPuv gene reporter were constructed and sequences are as follows: pSMART-amnp-GFPuv (SEQ ID NO:36), pSMART-phoAp-GFPuv (SEQ ID NO:37), pSMART-phoBp-GFPuv (SEQ ID NO:38), pSMART-phoEp-GFPuv (SEQ ID NO:38), pSMART-phoHp-GFPuv (SEQ ID NO:40), pSMART-phoUp-GFPuv (SEQ ID NO:41), pSMART-mipAp-GFPuv (SEQ ID NO:42), pSMART-pstSp-GFPuv (SEQ ID NO:43), pSMART-ugpBp-GFPuv (SEQ ID NO:12), pSMART-waaHp-GFPuv (SEQ ID NO:44), and pSMART-ydfHp-GFPuv (SEQ ID NO:45). Briefly, plasmids were transformed into E. coli strain BWapldf (Refer to Example 4). Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 µL of normalized culture was used to inoculate 760 µL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence. Cells were incubated in the Microreactor at 37 degrees Celsius and a shaking speed of 1200 rpm for 60 hrs. Growth stopped and phosphate depletion begins at about 15-20 hrs (data not shown for clarity). Fluorescence results for each reporter construct as well as an empty vector control are reported as relative fluorescence units (R.F.U) in FIG. 6. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*.

Example 6 pCASCADE Plasmid Cloning pCASCADE-control (SEQ ID NO:13) was prepared by swapping the tetracycline inducible promoter in perRNA plasmid (Luo et al. "Repurposing endogenous type I CRISPR-Cas systems for programmable gene repression" NAR. October 2014; DOI: 10.1093.) with an insulated ugpB promoter. The plasmid was constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations.

Additional pCASCADE plasmids with single RNA guides were prepared via Q5 site-directed mutagenesis (New England Biolabs, Ipswich, Mass., USA),) following manufacturer's protocol, except that 5% v/v DMSO was added to the Q5 PCR reaction. For example pCASCADE-gltA2 (SEQ ID NO:14) was prepared using pCASCADE-control as template and the following primers: gltA2-FOR 5'-GGGACAGTTATTAGTTCGAGTTCCCCGCGCCA GCGGGGATAAACCGAAAAAAAAACCCC-3' (SEQ ID NO:49) and gltA2-REV 5'-GAATGAATTGGT-CAATACGGTTTATCCCCGCTGGCGCGGG-GAACTCGAGGTGGT ACCAGATCT-3' (SEQ ID NO:50). Additional pCASCADE plasmids including pCASCADE-fabI (SEQ ID NO:15), pCASCADE-udhA, (SEQ ID NO:16), pCASCADE-zwf (SEQ ID NO:17) and pCAS-CADE-gltA1 (SEQ ID NO:18) were prepared in a similar manner by exchanging the guide RNA targeting sequence using Q5 mutagenesis.

Additional pCASCADE plasmids with multiple RNA guides were prepared as follows. For example pCASCADE-gltA2-udhA (SEQ ID NO:19) plasmid was prepared by amplifying gltA2 guide half and udhA guide half from pCASCADE-gltA2 and pCASCADE-udhA respectively using Q5 High-Fidelity 2× Master Mix (NEB, MA). The primers used: G2U-FOR1: 5'-CCGGATGAGCATT-CATCAGGCGGGCAAG-3' (SEQ ID NO:51), REV1: 5'-CGGTTTATCCCCGCTGGCGCGGG-GAACTCGAACTTCATAACTTTTAC-3' (SEQ ID NO:52) and FOR2: 5'-GCGCCAGCGGGGATAAACCGTTAC-CATTCTGTTG-3' (SEQ ID NO:53) and REV2: 5'-CTTGCCCGCCTGATGAATGCTCATCCGG-3' (SEQ ID NO:54). PCR products were purified by gel-extraction and were then used for Gibson Assembly (NEB, MA). pCASCADE-fabI-udhA (SEQ ID NO:20), pCASCADE-fabI-gltA1 (SEQ ID NO:21), pCASCADE-fabI-gltA2 (SEQ ID NO:22), pCASCADE-fabI-zwf (SEQ ID NO:23), pCAS-CADE-gltA1-udhA (SEQ ID NO:24), pCASCADE-gltA2-udhA (SEQ ID NO:25), pCASCADE-gltA1-zwf (SEQ ID NO:26), pCASCADE-gltA2-zwf (SEQ ID NO:27), were all prepared in a similar way by amplification of each guide and part of the vector backbone followed by Gibson Assembly. All plasmid sequences were confirmed by DNA sequencing (Eton Bioscience, Research Triangle Park, NC, USA).

Example 7

Figure 7:
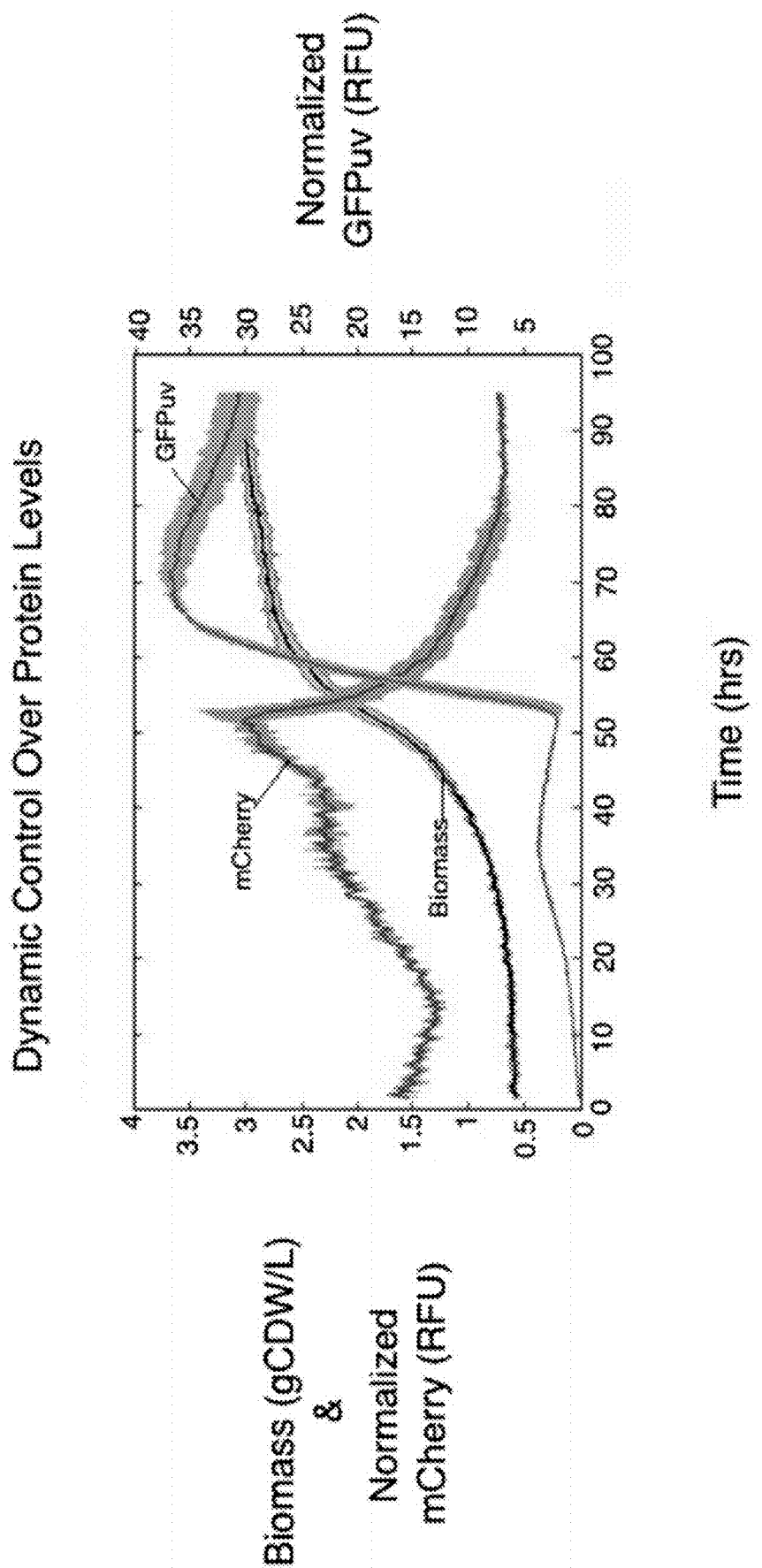
FIG. 7 depicts the dynamic control over protein levels in E. coli using the CASCADE System and controlled proteolysis. Strain DLF_0025 (enabling low phosphate DAS+4 degradation) has been modified to constitutively express a mCherry protein with a C-terminal DAS+4 degradation tag. In addition the strain has been modified for the low phosphate induction of GFPuv as well as a guide RNA repressing mCherry expression. As cells grow phosphate is depleted, and cells "turn off" mCherry and "turn on" GFPuv. Biomass is plotted as grams cell dry weight per liter, GFPuv and mCherry are plotted as relative fluorescence units (RFU) which are normalized to biomass levels.

Dynamic Control Over Protein Levels in *E. coli* Using the CASCADE System and Controlled Proteolysis All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*. First a plasmid expressing a low phosphate inducible (utilizing the low phosphate inducible waaH gene promoter from *E. coli*), ultraviolet excitable, green fluorescent protein (GFPuv) was constructed using standard cloning techniques and called pSMART-waaHp-GFPuv (SEQ ID NO:12). Secondly, a compatible vector with the constitutive expression of a red fluorescent protein (mCherry), tagged with a DAS+4 tag enabling controlled proteolysis was constructed pBT1-mCherry-DAS+4 (SEQ ID NO:28). Constitutive expression was achieved using a proD promoter (Davis, J H., Rubin, A J., and Sauer, R T. NAR. February 2011; 39(3) p 1131-1141. DOI: 10.1093). Lastly, another compatible vector enabling the low phosphate expression (utilizing the low phosphate inducible ugpB gene promoter from *E. coli*) expression of a gene silencing guide RNA targeting the proD promoter was constructed (Refer to Example 6 for methods) and called pCASCADE-proD (SEQ ID NO:29). These plasmids were transformed into several host strains as described in Example 4, including strain DLF_0025 to create several strains. Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 μL of normalized culture was used to inoculate 760 μL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence and biomass levels. Cells were incubated in the Microreactor at 37 degrees Celsius and a shaking speed of 1200 rpm for 60 hrs. Fluorescence results for each reporter construct as well as an empty vector control are reported as relative fluorescence units (R.F.U) normalized to biomass levels are depicted in FIG. 7. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*.

Example 8

E. coli Pathway Plasmid Cloning

All production plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in E. coli.

A plasmid expressing an NADPH dependent 3-hydroxypropionic acid (3-HP) production pathway was constructed as an operon of two genes. The mcr gene from Chloroflexus auranticus (CaMCR), encoding a malonyl-CoA reductase (Uniprot #A9WIU3), and the ydfG gene from E. coli, encoding an NADPH dependent 3-HP dehydrogenase (Uniprot #P39831) were used. Only the C-terminal end (residues 550-1219) of the mcr enzyme encoding the malonyl-CoA reductase domain was utilized (Liu, C., Wang, Q., Ding., Y and Zhao, Gu., PLOS One. September 2013. DOI: 10.1371). The operon was assembled into the pSMART-HC-Kan vector, resulting in plasmid pSMART-3HP1, (SEQ ID NO:30).

A plasmid expressing a malonic acid production pathway was constructed from a single gene encoding a triple mutant (E95N/Q384A/F304R) Pseudomonas fulva (strain 12-X) isobutyryl-CoA thioesterase (Uniprot #F6AA82), with altered specificity (Steen, E., Patent Application PCT/US2014/047645). This gene was cloned behind the phosphate dependent waaH gene promoter from E. coli. The gene was then assembled into the pSMART-HC-Kan vector (Lucigen, Middleton Wis.), resulting in plasmid pSMART-F6AA82M, (SEQ ID NO:31).

A plasmid expressing an NADPH dependent L-alanine production pathway was constructed from a single gene encoding a double mutant (Leu197Arg Asp196Ala) Bacillus subtilis alanine dehydrogenase (AlaDH) (Uniprot #Q08352), with NADPH cofactor specificity (Haas, T., et al. Patent Application PCT/EP2013/057855). This gene was cloned behind the phosphate dependent waaH gene promoter from E. coli. The gene was then assembled into the pSMART-HC-Kan vector (Lucigen, Middleton Wis.), resulting in plasmid pSMART-Ala1, (SEQ ID NO:32). A additional plasmid expressing the same NADPH dependent L-alanine production pathway was constructed using the phosphate dependent ugpB gene promoter from E. coli. The gene was then assembled into the pSMART-HC-Kan vector (Lucigen, Middleton Wis.), resulting in plasmid pSMART-Ala2, (SEQ ID NO:46).

A plasmid expressing a mevalonate production pathway was constructed from two genes assembled into two transcriptional units. First, the mvaE gene from Enterococcus faecalis encoding a bifunctional acetoacetyl-CoA thiolase, and NADPH dependent HMG-CoA reductase (Uniprot #Q9FD70) was cloned behind an insulated version of the phosphate dependent waaH gene promoter from E. coli. Additionally, the mvaS gene, also from E. faecalis, encoding a hydroxymethylglutaryl-CoA synthase (Uniprot #Q9FD71) was cloned behind an insulated version of the phosphate dependent mipA gene promoter from E. coli. The mvaS expression construct was cloned behind the mvaE construct and both assembled into the pSMART-HC-Kan vector, resulting in plasmid pSMART-Mev1, (SEQ ID NO:33).

A plasmid expressing an NADH dependent 2,3-butanediol production pathway was constructed as an operon of three genes. The budA, budB and budC genes from Enterobacter cloacae subsp. dissolvens SDM, encoding an α-acetolactate decarboxylase, an acetolactate synthase and acetoin reductase, respectively, were cloned behind the phosphate dependent waaH gene promoter from E. coli. The operon was assembled into the pSMART-HC-Kan vector, resulting in plasmid pSMART-2,3-BDO1, (SEQ ID NO:34).

A plasmid expressing an NADPH dependent 2,3-butanediol production pathway was constructed as an operon of three genes. The budA, budB genes from Enterobacter cloacae subsp. dissolvens SDM, encoding an α-acetolactate decarboxylase, an acetolactate synthase, and a Glu221Ser/Ile222Arg/Ala223Ser triple mutant bdhI gene from S. cerevisiae, encoding an NADPH dependent acetoin reductase (Ehsani, M., Fernandez, M R., Biosca J A and Dequin, S. Biotechnol Bioeng. 2009 Oct. 1; 104(2):381-9. doi: 10.1002) respectively, were cloned behind the phosphate dependent waaH gene promoter from E. coli. The operon was assembled into the pSMART-HC-Kan vector, resulting in plasmid pSMART-2,3-BDO2 (SEQ ID NO:35).

Example 9

Production of 3-Hydroxypropionic Acid (3-HP) in E. coli, From Malonyl-CoA and NADPH in 96 Well Plates Several E. coli strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 2.

TABLE 2

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |
| 11 | DLF_0286 | | Empty vector | 0 | 0 |
| 12 | DLF_0039 | | pSMART-3HP1 | 0 | 0 |
| 13 | DLF_0028 | pCASCADE-fabI | pSMART-3HP1 | 0 | 0 |
| 14 | DLF_0028 | pCASCADE-fabI-zwf | pSMART-3HP1 | 0 | 0 |
| 15 | DLF_0043 | pCASCADE-fabI | pSMART-3HP1 | 0 | 0 |
| 16 | DLF_0025 | pCASCADE-fabI | pSMART-3HP1 | 0.02 | 0.03 |
| 17 | DLF_0045 | pCASCADE-udhA-gltA2 | pSMART-3HP1 | 0.11 | 0.06 |

TABLE 2-continued

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 18 | DLF_0025 | | pSMART-3HP1 | 0.16 | 0.14 |
| 19 | DLF_0043 | pCASCADE-gltA2 | pSMART-3HP1 | 0.19 | 0.06 |
| 20 | DLF_0025 | pCASCADE-fabI-udhA | pSMART-3HP1 | 0.36 | 0.18 |
| 21 | DLF_0046 | | pSMART-3HP1 | 0.41 | 0.14 |
| 22 | DLF_0039 | pCASCADE-fabI-gltA2 | pSMART-3HP1 | 0.45 | 0.29 |
| 23 | DLF_0028 | | pSMART-3HP1 | 0.55 | 0.24 |
| 24 | DLF_0025 | pCASCADE-udhA | pSMART-3HP1 | 0.57 | 0.14 |
| 25 | DLF_0046 | pCASCADE-fabI-udhA | pSMART-3HP1 | 0.58 | 0.09 |
| 26 | DLF_0025 | pCASCADE-fabI-zwf | pSMART-3HP1 | 0.66 | 0.26 |
| 27 | DLF_0046 | pCASCADE-fabI-zwf | pSMART-3HP1 | 0.89 | 0.11 |
| 28 | DLF_0047 | pCASCADE-fabI-gltA1 | pSMART-3HP1 | 1.00 | 1.74 |
| 29 | DLF_0038 | pCASCADE-fabI-udhA | pSMART-3HP1 | 1.58 | 0.32 |
| 30 | DLF_0039 | pCASCADE-gltA1 | pSMART-3HP1 | 1.66 | 0.34 |
| 31 | DLF_0047 | pCASCADE-fabI | pSMART-3HP1 | 1.82 | 0.41 |
| 32 | DLF_0047 | pCASCADE-fabI-zwf | pSMART-3HP1 | 2.05 | 0.16 |
| 33 | DLF_0038 | | pSMART-3HP1 | 2.09 | 0.34 |
| 34 | DLF_0047 | pCASCADE-fabI-udhA | pSMART-3HP1 | 2.28 | 0.39 |
| 35 | DLF_0047 | pCASCADE-udhA | pSMART-3HP1 | 2.33 | 1.30 |
| 36 | DLF_0291 | pCASCADE-gltA2 | pSMART-3HP1 | 3.17 | 0.93 |
| 37 | DLF_0291 | pCASCADE-udhA-gltA2 | pSMART-3HP1 | 4.95 | 2.18 |

Example 10

Figure 8:
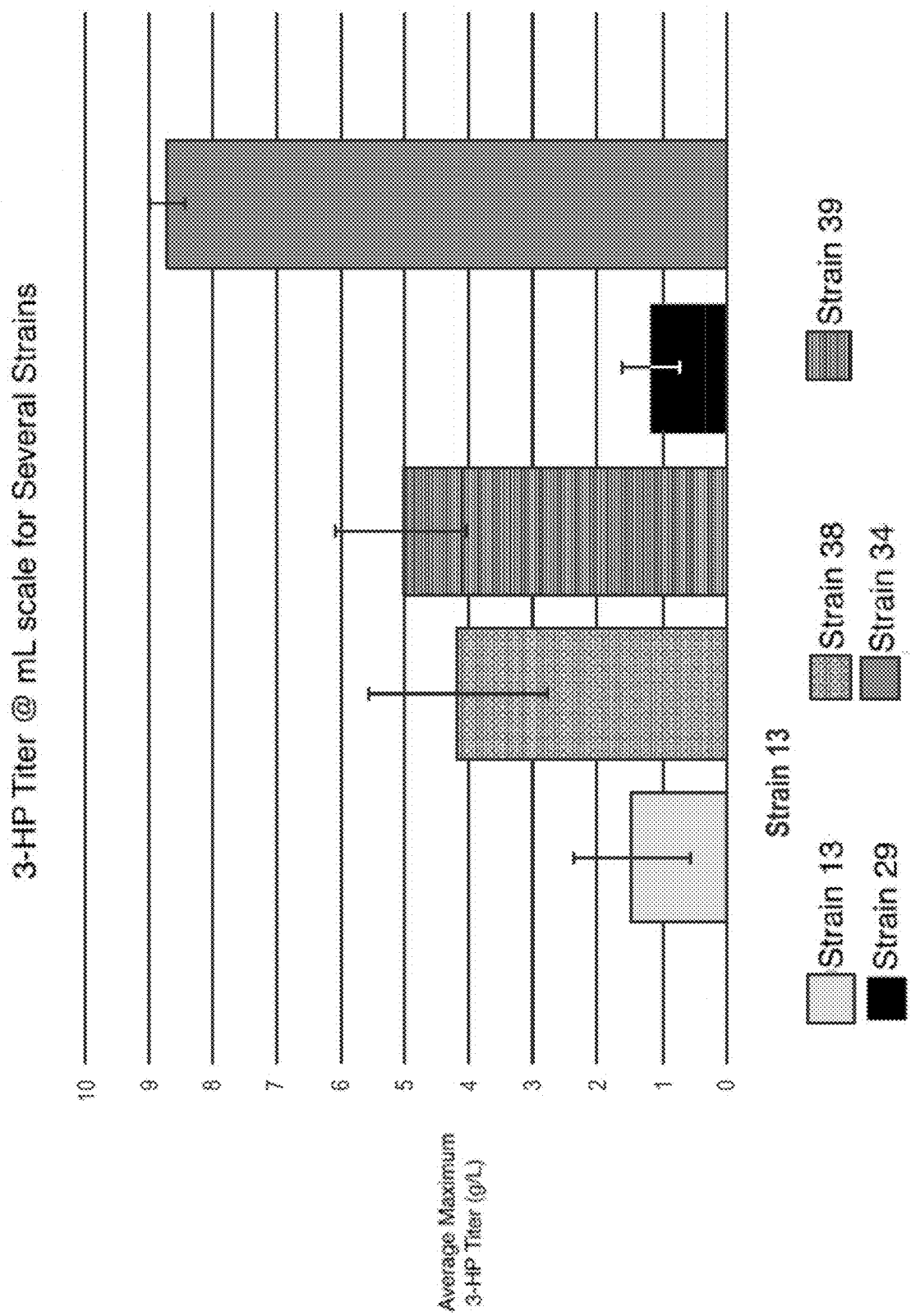
FIG. 8 depicts the production of 3-HP from malonyl-CoA and NADPH at mL scale. Average Maximal 3-HP titers are plotted for several production strains.

Production of 3-Hydroxypropionic Acid (3-HP) in E. coli, From Malonyl-CoA and NADPH at mL Scale Several E. coli strains were constructed utilizing a combination of host strains as described in Example 5, production pathway plasmids as described in Example 6 and CASCADE based gene silencing constructs such as those described in Example 7. Strains were then evaluated for product formation using the standard mL scale evaluation protocol "Micro24 Protocol—1" as described in the Common Methods Section. Products levels were then measured using the analytical methods as described in the Common Methods Section. Summary metrics are listed in Table 3 and shown in FIG. 8.

TABLE 3

3-HP Summary Production metrics for 3-HP produced from malonyl-CoA and NADPH at mL scale.

| Strain | Host Strain | pCASCADE plasmid | Production Plasmid | Final 3-HP Titer (g/L) |
|---|---|---|---|---|
| 18 | DLF_0025 | | pSMART-3HP1 | Below Detection |
| 13 | DLF_0028 | pCASCADE-fabI | pSMART-3HP1 | 1.48 ± 0.91 |
| 38 | DLF_0038 | pCASCADE-fabI | pSMART-3HP1 | 4.19 ± 1.39 |
| 39 | DLF_0038 | pCASCADE-udhA | pSMART-3HP1 | 5.07 ± 1.03 |
| 29 | DLF_0038 | pCASCADE-fabI-udhA | pSMART-3HP1 | 1.17 ± 0.44 |
| 34 | DLF_0047 | pCASCADE-fabI-udhA | pSMART-3HP1 | 8.71 ± 0.28 |

Example 11

Figure 9:
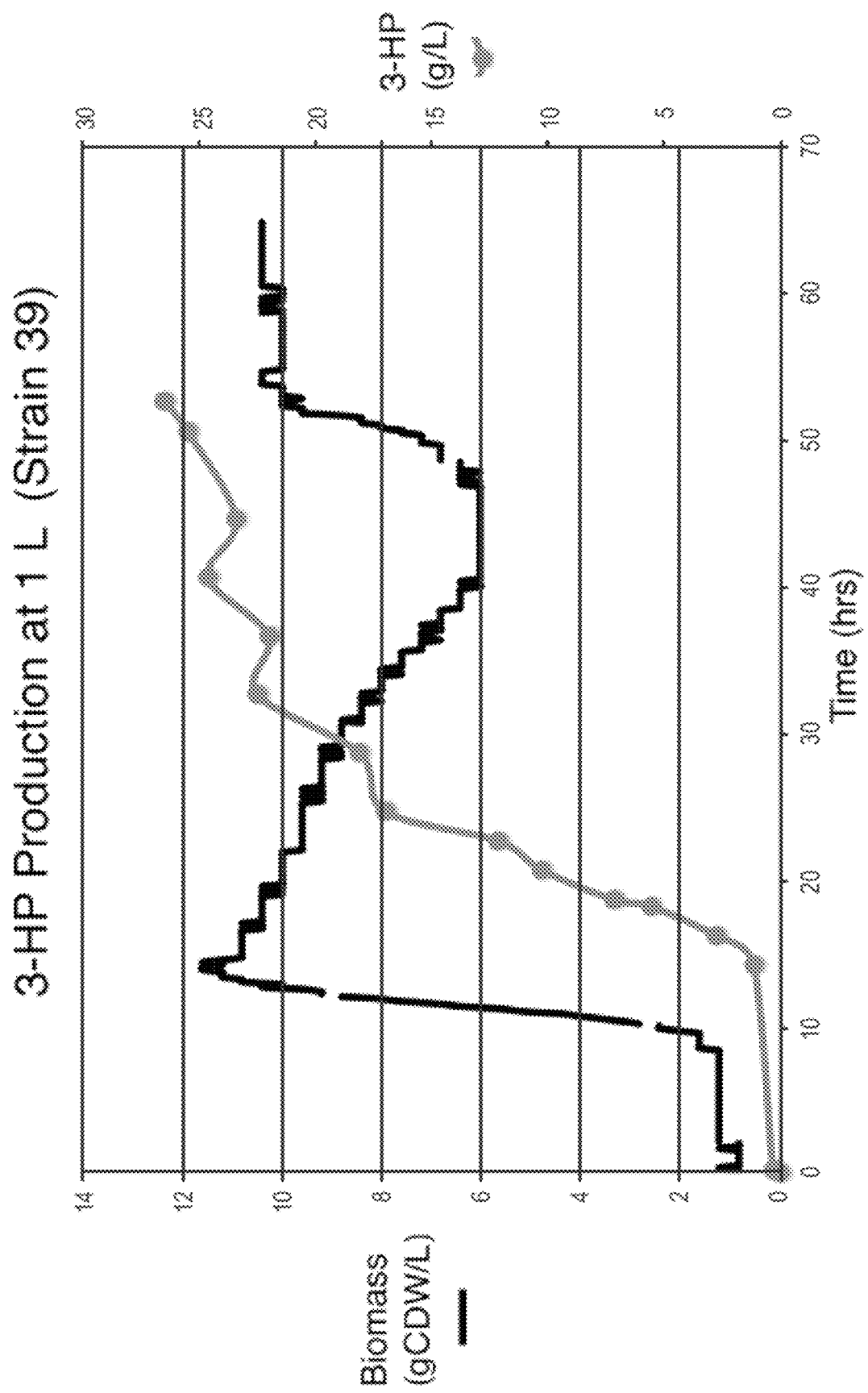
FIG. 9 depicts the production of 3-HP from malonyl-CoA and NADPH at L scale. Biomass and 3-HP titers are plotted as a function of time.

Production of 3-Hydroxypropionic Acid (3-HP) in E. coli, From Malonyl-CoA and NADPH L Scale E. coli strain 39 from Example 10, was evaluated at 1 L scale using the standard evaluation protocol "1 L Fermentation Protocol—1" as described in the Common Methods Section. Products levels were then measured using the analytical methods as described in the Common Methods Section. Biomass growth and 3-HP production are shown in FIG. 9.

Example 12

Production of Malonic Acid in E. coli, From Malonyl-CoA in 96 Well Plates

Several E. coli strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 4.

TABLE 4

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |

TABLE 4-continued

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 11 | DLF_0286 | | Empty vector | 0 | 0 |
| 40 | DLF_0025 | pCASCADE-control | Empty vector | 0 | 0 |
| 41 | DLF_0025 | pCASCADE-control | pSMART-F6AA82M | 0 | 0 |
| 42 | DLF_0028 | pCASCADE-control | pSMART-F6AA82M | 0.19 | 0.095 |
| 43 | DLF_0039 | pCASCADE-control | pSMART-F6AA82M | 0 | 0 |
| 44 | DLF_0039 | pCASCADE-gltA1 | pSMART-F6AA82M | 0 | 0 |
| 45 | DLF_0039 | pCASCADE-gltA2 | pSMART-F6AA82M | 0 | 0 |
| 46 | DLF_0039 | pCASCADE-zwf | pSMART-F6AA82M | 0 | 0 |
| 47 | DLF_0290 | pCASCADE-control | pSMART-F6AA82M | 0.017 | 0.029 |
| 48 | DLF_0167 | pCASCADE-control | pSMART-F6AA82M | 0.45 | 0.04 |

Example 13

Production of Alanine in *E. coli*, From Pyruvate in 96 Well Plates

Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 5.

TABLE 5

Alanine Production from pyruvate and NADPH in 96 well plates

| Strain | Host Strain | pCASCADE plasmid | Production Plasmid | Final Alanine Titer (g/L) | Final Alanine Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 49 | DLF_0042 | | pSMART-Ala1 | 2.62 | 0.069 |
| 50 | DLF_0043 | pCASCADE-udhA-gltA1 | pSMART-Ala2 | 0 | 0 |
| 51 | DLF_0041 | pCASCADE-udhA-gltA1 | pSMART-Ala2 | 0.23 | 0.075 |
| 52 | DLF_0041 | | pSMART-Ala1 | 0.71 | 0.256 |
| 53 | DLF_0049 | pCASCADE-udhA-gltA2 | pSMART-Ala2 | 1.26 | 0.737 |
| 54 | DLF_0025 | | pSMART-Ala1 | 1.39 | 0.338 |
| 55 | DLF_0049 | | pSMART-Ala1 | 1.48 | 0.136 |
| 56 | DLF_0031 | | pSMART-Ala1 | 1.62 | 0.245 |
| 57 | DLF_0042 | pCASCADE-udhA | pSMART-Ala2 | 1.63 | 0.190 |
| 58 | DLF_0043 | | pSMART-Ala1 | 1.64 | 0.104 |
| 59 | DLF_0043 | pCASCADE-gltA2 | pSMART-Ala2 | 1.72 | 0.355 |
| 60 | DLF_0049 | pCASCADE-udhA | pSMART-Ala2 | 2.42 | 0.105 |
| 61 | DLF_0045 | pCASCADE-udhA-gltA2 | pSMART-Ala2 | 2.44 | 0.125 |
| 62 | DLF_0049 | pCASCADE-gltA2 | pSMART-Ala2 | 2.74 | 0.551 |
| 63 | DLF_0041 | pCASCADE-gltA2 | pSMART-Ala2 | 3.32 | 1.501 |
| 64 | DLF_0045 | | pSMART-Ala1 | 3.65 | 0.441 |
| 65 | DLF_0043 | pCASCADE-udhA-gltA2 | pSMART-Ala2 | 4.03 | 0.202 |

Example 14

Production of Alanine in *E. coli*, From Pyruvate at mL Scale

Figure 10:
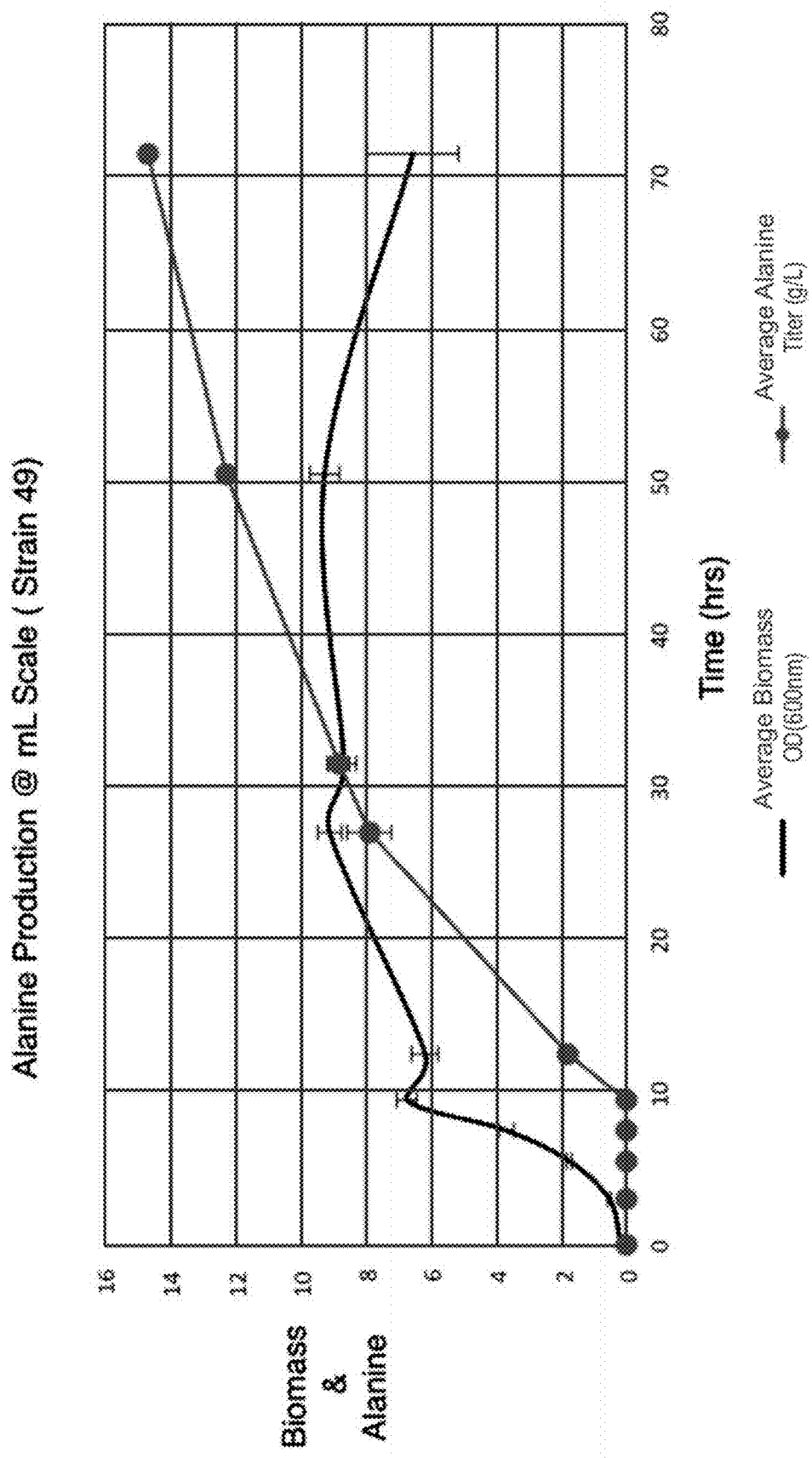
FIG. 10 depicts the production of alanine from pyruvate and NADPH at mL scale. Biomass and alanine titers are plotted as a function of time.

*E. coli* strain 49 from Example 13, was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 10.

Example 15

Production of Alanine in *E. coli*, From Pyruvate at L Scale

Figure 11:
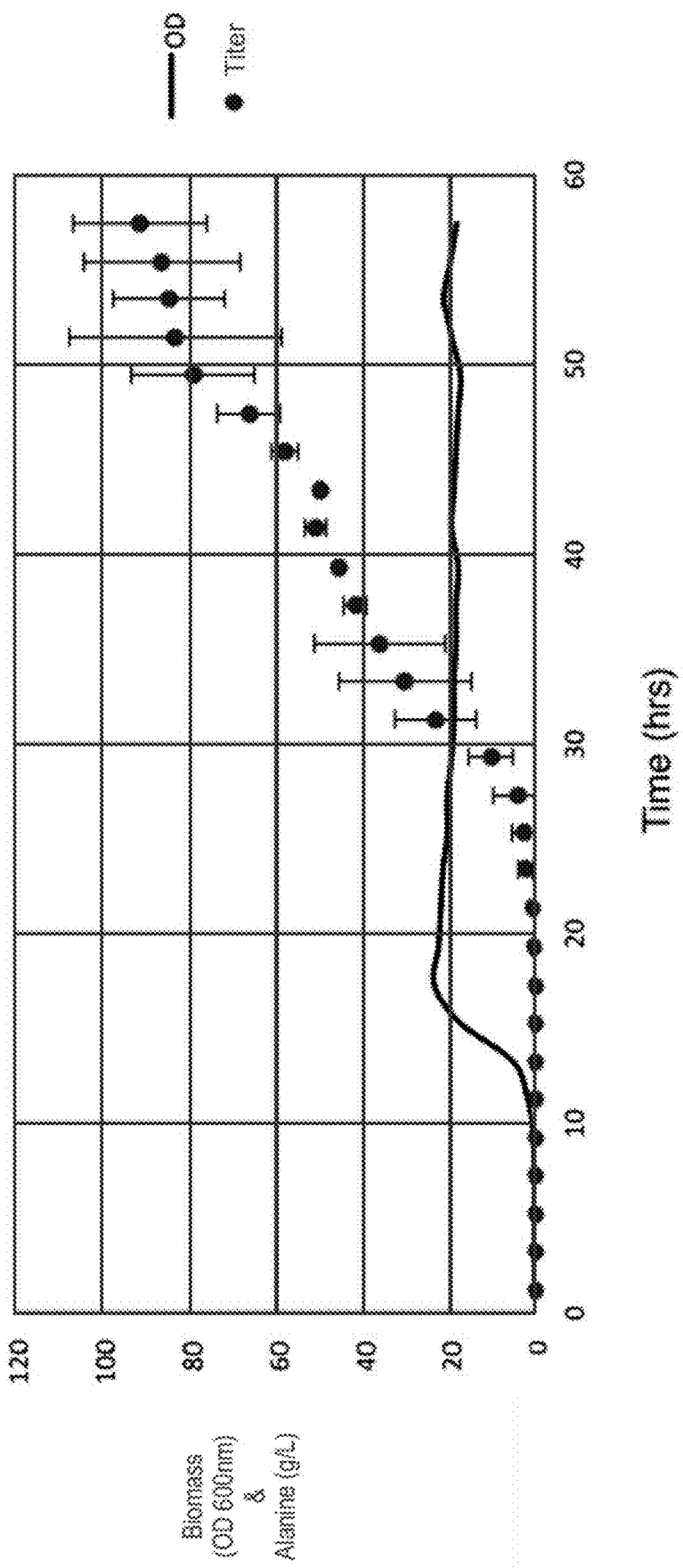
FIG. 11 depicts the production of alanine from pyruvate and NADPH at the L scale. Biomass and alanine titers are plotted as a function of time.

*E. coli* strain 60 from Example 13, was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 11.

Example 16

Production of 2,3-Butanediol in *E. coli*, From Pyruvate and NADH at mL Scale

Figure 12:
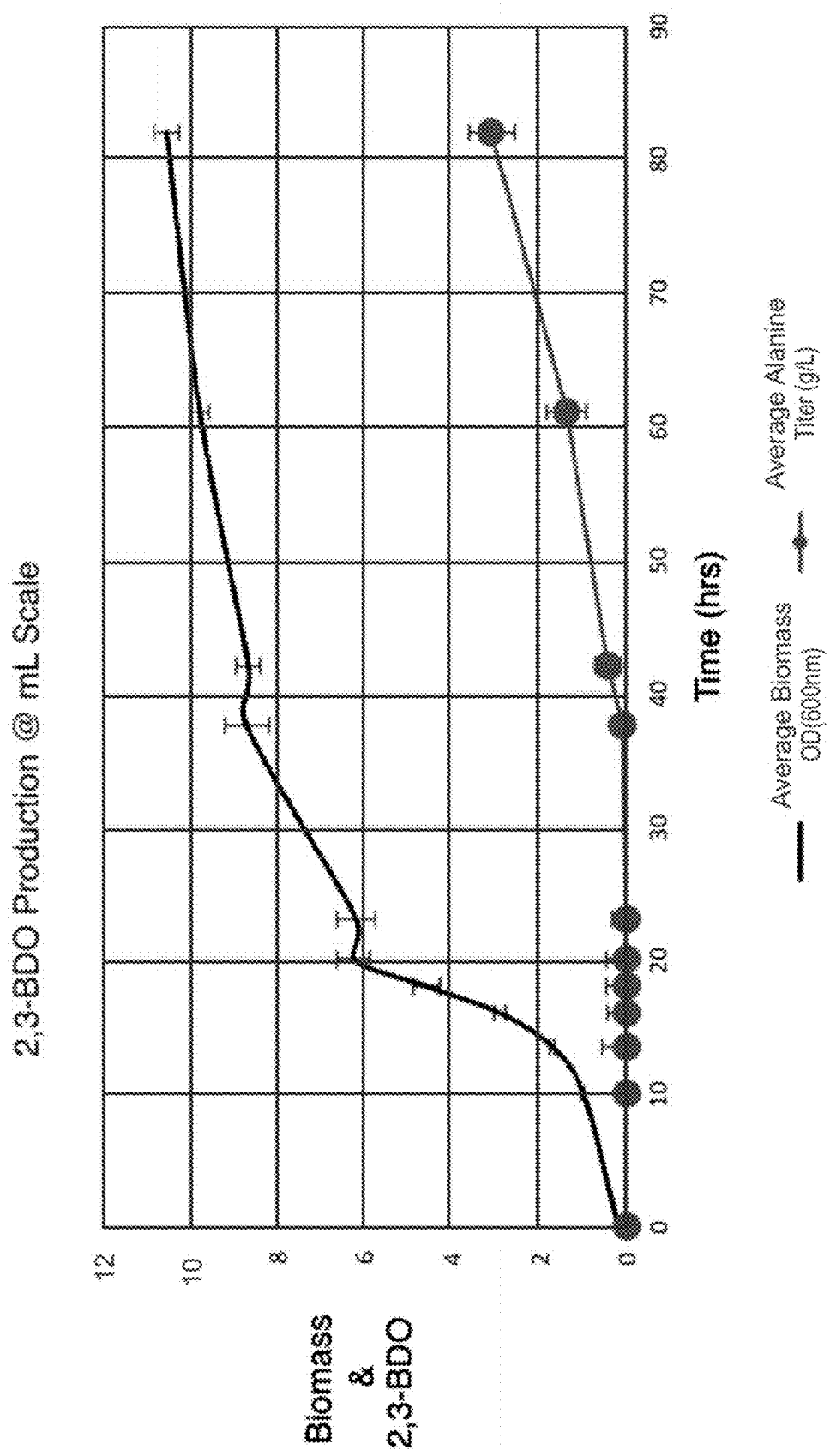
FIG. 12 depicts the production of 2,3-butanediol from pyruvate and NADH at mL scale. Biomass and 2,3-butanediol titers are plotted as a function of time.

An *E. coli* strain was made by transforming host strain DLF_00165 with both plasmid pSMART-2,3-BDO1 and pCASCADE-zwf (Refer to Examples 4, 6 and 8). This strain was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 12.

Example 17

Production of 2,3-Butanediol in *E. coli*, From Pyruvate and NADH at L Scale

Figure 13:
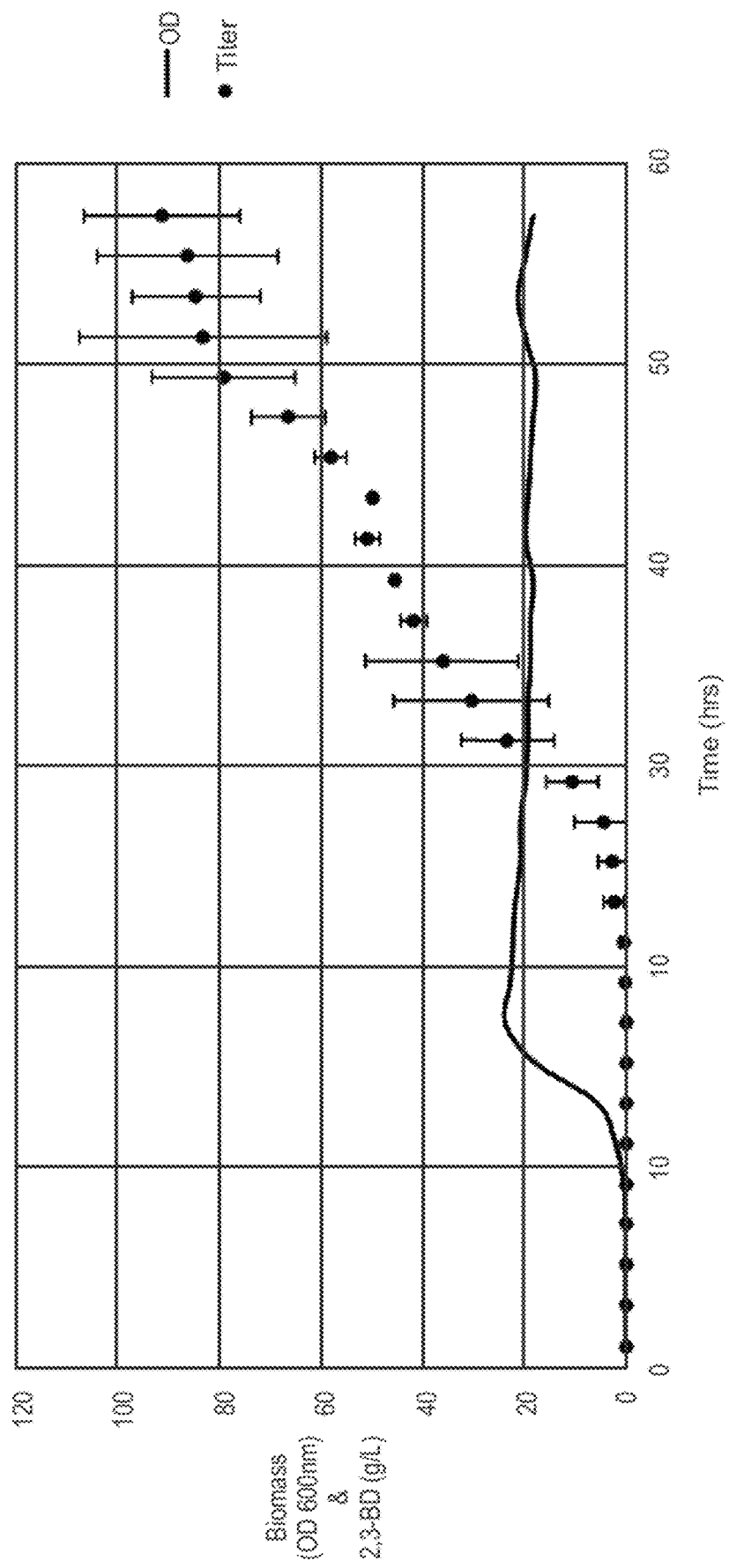
FIG. 13 depicts the production of 2,3-butanediol from pyruvate and NADH at L scale. Biomass and 2,3-butanediol titers are plotted as a function of time.

An *E. coli* strain was made by transforming host strain DLF_00165 with both plasmid pSMART-2,3-BDO1 and pCASCADE-zwf (Refer to Examples 4, 6 and 8). This strain was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 13.

Example 18

Production of 2,3-Butanediol in *E. coli*, From Pyruvate and NADPH at mL Scale

Figure 14:
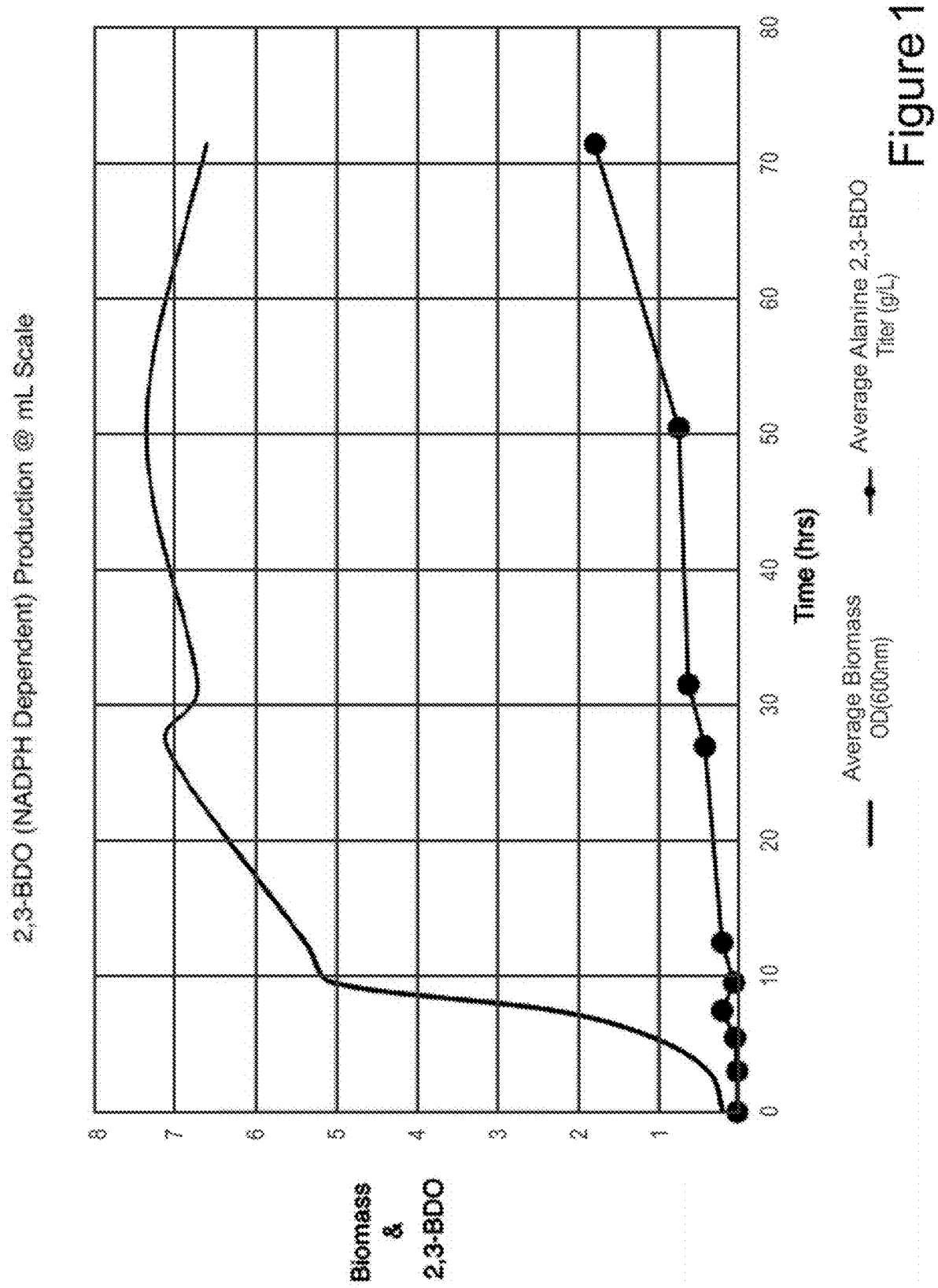
FIG. 14 depicts the production of 2,3-butanediol from pyruvate and NADPH at mL scale. Biomass and 2,3-butanediol titers are plotted as a function of time.

An *E. coli* strain was made by transforming host strain DLF_00049 with both plasmid pSMART-2,3-BDO2 and pCASCADE-udhA (Refer to Examples 4, 6 and 8). This strain was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 14.

Example 19

Production of Mevalonic Acid in *E. coli*, From Acetyl-CoA and NADPH at L Scale

Figure 15:
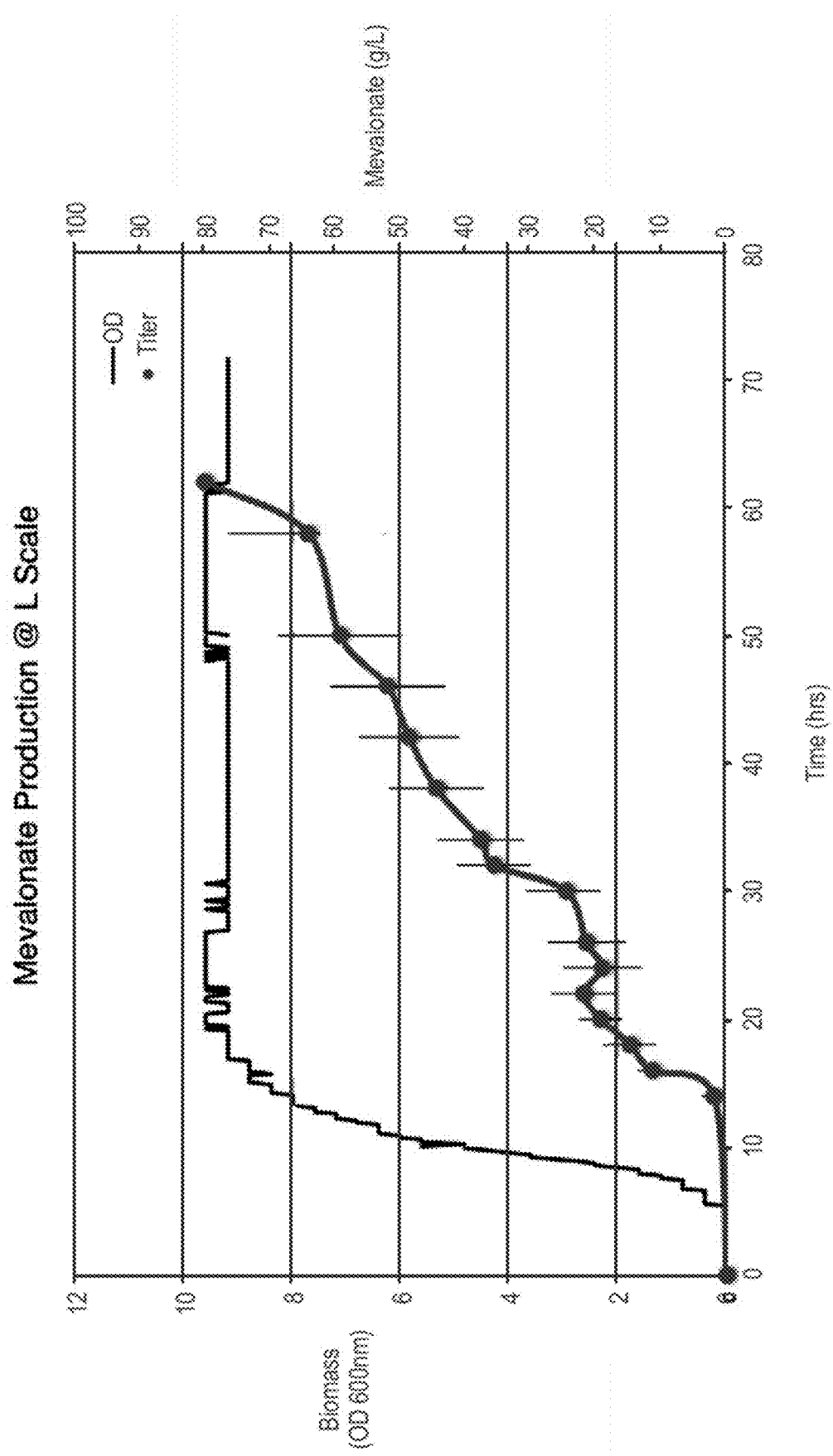
FIG. 15 depicts the production of mevalonic acid from acetyl-CoA and NADPH at L scale. Biomass and mevalonic acid titers are plotted as a function of time.

An *E. coli* strain was made by transforming host strain DLF_0004 with plasmid pSMART-Mev1 (Refer to Examples 4 and 8). This strain was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 15.

Common Methods Section

All methods in this Section are provided for incorporation into the Examples where so referenced.

Subsection I. Microorganism Species and Strains, Cultures, and Growth Media

Microbial species, that may be utilized as needed, are as follows:

*Acinetobacter calcoaceticus* (DSMZ #1139) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of theresuspended *A. calcoaceticus* culture are made into BHI and are allowed to grow for aerobically for 48 hours at 37° C. at 250 rpm until saturated.

*Bacillus subtilis* is a gift from the Gill lab (University of Colorado at Boulder) and is obtained as an actively growing culture. Serial dilutions of the actively growing *B. subtilis* culture are made into Luria Broth (RPI Corp, Mt. Prospect, Ill., USA) and are allowed to grow for aerobically for 24 hours at 37° C. at 250 rpm until saturated.

*Chlorobium limicola* (DSMZ #245) is obtained from the German Collection of Microorganisms and Cell Cultures (Braunschweig, Germany) as a vacuum dried culture. Cultures are then resuspended using Pfennig's Medium I and II (#28 and 29) as described per DSMZ instructions. *C. limicola* is grown at 25° C. under constant vortexing.

*Citrobacter braakii* (DSMZ #30040) is obtained from the German Collection of Microorganisms and Cell Cultures (Braunschweig, Germany) as a vacuum dried culture. Cultures are then resuspended in Brain Heart Infusion(BHI) Broth (RPI Corp, Mt. Prospect, Ill., USA). Serial dilutions of the resuspended *C. braakii* culture are made into BHI and are allowed to grow for aerobically for 48 hours at 30° C. at 250 rpm until saturated.

*Clostridium acetobutylicum* (DSMZ #792) is obtained from the German Collection of Microorganisms and Cell Cultures (Braunschweig, Germany) as a vacuum dried culture. Cultures are then resuspended in *Clostridium acetobutylicum* medium (#411) as described per DSMZ instructions. *C. acetobutylicum* is grown anaerobically at 37° C. at 250 rpm until saturated.

*Clostridium aminobutyricum* (DSMZ #2634) is obtained from the German Collection of Microorganisms and Cell Cultures (Braunschweig, Germany) as a vacuum dried culture. Cultures are then resuspended in *Clostridium aminobutyricum* medium (#286) as described per DSMZ instructions. *C. aminobutyricum* is grown anaerobically at 37° C. at 250 rpm until saturated.

*Clostridium kluyveri* (DSMZ #555) is obtained from the German Collection of Microorganisms and Cell Cultures (Braunschweig, Germany) as an actively growing culture. Serial dilutions of *C. kluyveri* culture are made into *Clostridium kluyveri* medium (#286) as described per DSMZ instructions. *C. kluyveri* is grown anaerobically at 37° C. at 250 rpm until saturated.

*Cornyebacterium glutamicum* (DSMZ #1412) is obtained from the German Collection of Microorganisms and Cell Cultures (Braunschweig, Germany) as an actively growing culture. Serial dilutions of *C. glutamicum* culture are made into *C. glutamicum* medium (#1) as described per DSMZ instructions. *C. glutamicum* is grown aerobically or anaerobically at 37° C. at 250 rpm until saturated.

*Cupriavidus metallidurans* (DMSZ #2839) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. metallidurans* culture are made into BHI and are allowed to grow for aerobically for 48 hours at 30° C. at 250 rpm until saturated.

*Cupriavidus necator* (DSMZ #428) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. necator* culture are made into BHI and are allowed to grow for aerobically for 48 hours at 30° C. at 250 rpm until saturated. As noted elsewhere, previous names for this species are *Alcaligenes eutrophus* and *Ralstonia eutrophus*.

*Desulfovibrio fructosovorans* (DSMZ #3604) is obtained from the German Collection of Microorganisms and Cell Cultures (Braunschweig, Germany) as a vacuum dried culture. Cultures are thenresuspended in *Desulfovibrio fruc-*

*tosovorans* medium (#63) as described per DSMZ instructions. *D. fructosovorans* is grown anaerobically at 37° C. at 250 rpm until saturated.

*Escherichia coli* strain BW25113 is obtained from the Yale Genetic Stock Center (New Haven, Conn. 06520) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Escherichia coli* strain BWapldf is a generous gift from George Chen from Tsinghua University in China. Serial dilutions of the actively growing *E. coli* BWapldf is culture are made into Luria Broth (RPI Corp, Mt. Prospect, Ill., USA) and are allowed to grow for aerobically for 24 hours at 37° C. at 250 rpm until saturated.

*Halobacterium salinarum* (DSMZ #1576) is obtained from the German Collection of Microorganisms and Cell Cultures (Braunschweig, Germany) as a vacuum dried culture. Cultures are then resuspended in *Halobacterium* medium (#97) as described per DSMZ instructions. *H. salinarum* is grown aerobically at 37° C. at 250 rpm until saturated.

*Lactobacillus delbrueckii* (#4335) is obtained from WYEAST USA (Odell, Oreg., USA) as an actively growing culture. Serial dilutions of the actively growing *L. delbrueckii* culture are made into Brain Heart Infusion (BHI) broth (RPI Corp, Mt. Prospect, Ill., USA) and are allowed to grow for aerobically for 24 hours at 30° C. at 250 rpm until saturated.

*Metallosphaera sedula* (DSMZ #5348) is obtained from the German Collection of Microorganisms and Cell Cultures (Braunschweig, Germany) as an actively growing culture. Serial dilutions of *M. sedula* culture are made into *Metallosphaera* medium (#485) as described per DSMZ instructions. *M. sedula* is grown aerobically at 65° C. at 250 rpm until saturated.

*Methylococcus capsulatus* Bath (ATCC #33009) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 45° C.

*Methylococcus thermophilus* IMV 2 Yu T is obtained. Cultures are then resuspended in ATCC® Medium 1306: Nitrate mineral salts medium (NMS) under a 50% air 50% methane atmosphere (ATCC, Manassas, Va. 20108 USA) and are allowed to grow at 50° C.

*Methylosinus tsporium* (ATCC #35069) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 30° C.

*Pichia pastoris* (*Komagataella pastoris*) (DSMZ #70382) is obtained from the German Collection of Microorganisms and Cell Cultures (Braunschweig, Germany) as a vacuum dried culture. Cultures are then resuspended in YPD-medium (#393) as described per DSMZ instructions. *Pichia pastoris* is grown aerobically at 30° C. at 250 rpm until saturated.

*Propionibacterium freudenreichii* subsp. *shermanii* (DSMZ #4902) is obtained from the German Collection of Microorganisms and Cell Cultures (Braunschweig, Germany) as a vacuum dried culture. Cultures are then resuspended in PYG-medium (#104) as described per DSMZ instructions. *P. freudenreichii* subsp. *shermanii* is grown anaerobically at 30° C. at 250 rpm until saturated.

*Pseudomonas putida* is a gift from the Gill lab (University of Colorado at Boulder) and is obtained as an actively growing culture. Serial dilutions of the actively growing *P. putida* culture are made into Luria Broth (RPI Corp, Mt. Prospect, Ill., USA) and are allowed to grow for aerobically for 24 hours at 37° C. at 250 rpm until saturated.

*Saccharomyces cerevisiae* strains can be obtained from the American Type Culture Collection (ATCC) (Manassas, Va. 20108 USA) as a vacuum dried culture. Cultures are then resuspended in YPD Media and allowed to grow at 30° C.

*Streptococcus mutans* (DSMZ #6178) is obtained from the German Collection of Microorganisms and Cell Cultures (Braunschweig, Germany) as a vacuum dried culture. Cultures are then resuspended in Luria Broth (RPI Corp, Mt. Prospect, Ill., USA). *S. mutans* is grown aerobically at 37° C. at 250 rpm until saturated.

*Yarrowia lipolytica* (DSMZ #1345) is obtained from the German Collection of Microorganisms and Cell Cultures (Braunschweig, Germany) as a vacuum dried culture. Cultures are then resuspended in YPD-medium (#393) as described per DSMZ instructions *Yarrowia lipolytica* is grown aerobically at 37° C. at 250 rpm until saturated.

Subsection II. Molecular Biology Techniques—DNA Cloning

In addition to the above or below specific examples, this example is meant to describe a non-limiting approach to genetic modification of a selected microorganism to introduce, remove or alter a nucleic acid sequence of interest. Alternatives and variations are provided within this general example. The methods of this example are conducted to achieve a combination of desired genetic modifications in a selected microorganism species, such as a combination of genetic modifications as described in sections herein, and their functional equivalents, such as in other bacterial and other microorganism species.

A gene or other nucleic acid sequence segment of interest is identified in a particular species (such as *E. coli* as described herein) and a nucleic acid sequence comprising that gene or segment is obtained.

Based on the nucleic acid sequences at the ends of or adjacent the ends of the segment of interest, 5' and 3' nucleic acid primers are prepared. Each primer is designed to have a sufficient overlap section that hybridizes with such ends or adjacent regions. Such primers may include enzyme recognition sites for restriction digest of transposase insertion that could be used for subsequent vector incorporation or genomic insertion. These sites are typically designed to be outward of the hybridizing overlap sections. Numerous contract services are known that prepare primer sequences to order (e.g., Integrated DNA Technologies, Coralville, Iowa USA).

Once primers are designed and prepared, polymerase chain reaction (PCR) is conducted to specifically amplify the desired segment of interest. This method results in multiple copies of the region of interest separated from the microorganism's genome. The microorganism's DNA, the primers, and a thermophilic polymerase are combined in a buffer solution with potassium and divalent cations (e.g., Mg or Mn) and with sufficient quantities of deoxynucleoside triphosphate molecules. This mixture is exposed to a standard regimen of temperature increases and decreases. However, temperatures, components, concentrations, and cycle times may vary according to the reaction according to length of the sequence to be copied, annealing temperature approximations and other factors known or readily learned through routine experimentation by one skilled in the art.

In an alternative embodiment the segment of interest may be synthesized, such as by a commercial vendor, and prepared via PCR, rather than obtaining from a microorganism or other natural source of DNA.

The nucleic acid sequences then are purified and separated, such as on an agarose gel via electrophoresis. Optionally, once the region is purified it can be validated by standard DNA sequencing methodology and may be introduced into a vector. Any of a number of vectors may be used, which generally comprise markers known to those skilled in the art, and standard methodologies are routinely employed for such introduction. Commonly used vector systems are well known in the art. Similarly, the vector then is introduced into any of a number of host cells. Commonly used host cells are *E. coli* strains. Some of these vectors possess promoters, such as inducible promoters, adjacent the region into which the sequence of interest is inserted (such as into a multiple cloning site). The culturing of such plasmid-laden cells permits plasmid replication and thus replication of the segment of interest, which often corresponds to expression of the segment of interest.

Various vector systems comprise a selectable marker, such as an expressible gene encoding a protein needed for growth or survival under defined conditions. Common selectable markers contained on backbone vector sequences include genes that encode for one or more proteins required for antibiotic resistance as well as genes required to complement auxotrophic deficiencies or supply critical nutrients not present or available in a particular culture media. Vectors also comprise a replication system suitable for a host cell of interest.

The plasmids containing the segment of interest can then be isolated by routine methods and are available for introduction into other microorganism host cells of interest. Various methods of introduction are known in the art and can include vector introduction or genomic integration. In various alternative embodiments the DNA segment of interest may be separated from other plasmid DNA if the former will be introduced into a host cell of interest by means other than such plasmid.

While steps of the general prophetic example involve use of plasmids, other vectors known in the art may be used instead. These include cosmids, viruses (e.g., bacteriophage, animal viruses, plant viruses), and artificial chromosomes (e.g., yeast artificial chromosomes (YAC) and bacteria artificial chromosomes (BAC)).

Host cells into which the segment of interest is introduced may be evaluated for performance as to a particular enzymatic step, and/or tolerance or bio-production of a chemical compound of interest. Selections of better performing genetically modified host cells may be made, selecting for overall performance, tolerance, or production or accumulation of the chemical of interest.

It is noted that this procedure may incorporate a nucleic acid sequence for a single gene (or other nucleic acid sequence segment of interest), or multiple genes (under control of separate promoters or a single promoter), and the procedure may be repeated to create the desired heterologous nucleic acid sequences in expression vectors, which are then supplied to a selected microorganism so as to have, for example, a desired complement of enzymatic conversion step functionality for any of the herein-disclosed metabolic pathways. However, it is noted that although many approaches rely on expression via transcription of all or part of the sequence of interest, and then translation of the transcribed mRNA to yield a polypeptide such as an enzyme, certain sequences of interest may exert an effect by means other than such expression.

The specific laboratory methods used for these approaches are well-known in the art and may be found in various references known to those skilled in the art, such as Sambrook and Russell, Molecular Cloning: A Laboratory Manual, Third Edition 2001 (volumes 1-3), Cold Spring Harbor Laboratory Press, Cold Spring Harbor, N.Y. (hereinafter, Sambrook and Russell, 2001).

As an alternative to the above, other genetic modifications may also be practiced, such as a deletion of a nucleic acid sequence of the host cell's genome. One non-limiting method to achieve this is by use of Red/ET recombination, known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany), and the method may proceed by following the manufacturer's instructions. Targeted deletion of genomic DNA may be practiced to alter a host cell's metabolism so as to reduce or eliminate production of undesired metabolic products. This may be used in combination with other genetic modifications such as described herein in this general example.

In addition to the above, longer purified double stranded DNA fragments can now be specified and ordered from a variety of vendors. These DNA pieces can easily be assembled together into plasmid vectors as well as longer synthetic DNA constructs using Gibson Assembly methodologies as taught by Gibson, D. G., et al. "Enzymatic assembly of DNA molecules up to several hundred kilobases" Nature Methods. May 2009. Vol(6) p. 343-345. doi:10.1038.

In addition to the above, once synthetic genetic parts such as open reading frames, promoters and terminators have been synthesized, it is well known in the art, that these parts can easily be shuffled into numerous different combinations using numerous variant assembly technologies, such as Golden Gate Assembly taught by Engler, C., Kandzia, R., and Marillonnet, S., "A one pot, one step, precision cloning method with high throughput capability". PLoS ONE 2008; 3(11):e3647. doi: 10.1371.

Subsection III. Molecular Biology Techniques—Chromosomal Modifications in *E. coli*

Chromosomal modifications can be made to *E. coli* using one of many methods including phage transduction and recombineering. It is appreciated that one skilled in the art is well versed in these methods. Of particular use are scarless recombineering methods, which allow for the precise deletion or addition of sequences to the chromosome without any unneeded sequences remaining such as that taught by Li, X., et al. "Positive and negative selection using the tetA-sacB cassette: recombineering and P1 transduction in *Escherichia coli*". Nucleic Acids Res. December 2013. 41(22) doi: 10.1093.

Subsection IV. Molecular Biology Techniques—Chromosomal Modifications in *Saccharomyces cerevisiae*.

Chromosomal modifications can be made to many yeast strains including *Saccharomyces cerevisiae*. using methods well known in the art for homologous recombination. It is appreciated that one skilled in the art is well versed in these methods.

Subsection V: Media For *E. coli*

GM25 media: GM25 minimal growth media for *E. coli* contained per liter: 736 mL sterile distilled, deionized water, 2.0 mL of 100× Trace Metals Stock, 100 mL of 10×GM phosphate salts, 2.0 mL of 2M $MgSO_4$, 50 mL of 500 g/L glucose, 100 mL of 1 M MOPS buffer, pH 7.4, and 10.0 mL of 100 g/L Yeast Extract. The 100× Trace Metal Stock was prepared in 1.0 L of distilled, deionized water with 10.0 mL of concentrated HCl with 5.0 g $CaCl_2*2H_2O$, 1.00 g $FeCl_3*6H_2O$, 0.05 g $CoCl_2*6H_2O$, 0.3 g $CuCl_2*2H_2O$, 0.02 g $ZnCl_2$, 0.02 g $Na_2MoO_4*2H_2O$, 0.01 g $H_3BO_3$, and 0.04 g $MnCl_2*4H_2O$ and 0.2 μm sterile-filtered. The 10×GM Phosphate Salts were prepared in 1.0 L of distilled, deionized water with 3 g $K_2HPO_4$, 2 g $KH_2PO_4$, 30 g $(NH_4)_2SO_4$, and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered.

PM25 media: PM25 minimal production media for *E. coli* contained per liter: 636 mL sterile distilled, deionized water, 2.0 mL of 100× Trace Metals Stock, 100 mL of 10×PM phosphate-free salts, 2.0 mL of 2M $MgSO_4$, 50 mL of 500 g/L glucose, 200 mL of 1 M MOPS buffer, pH 7.4, and 10 mL of 1 mg/mL Thiamine. The 100× Trace Metal Stock was prepared in 1.0 L of distilled, deionized water with 10.0 mL of concentrated HCl with 5.0 g $CaCl_2*2H_2O$, 1.00 g $FeCl_3*6H_2O$, 0.05 g $CoCl_2*6H_2O$, 0.3 g $CuCl_2*2H_2O$, 0.02 g $ZnCl_2$, 0.02 g $Na_2MoO_4*2H_2O$, 0.01 g $H_3BO_3$, and 0.04 g $MnCl_2*4H_2O$ and 0.2 μm sterile-filtered. The 10×PM Phosphate-Free Salts were prepared in 1.0 L of distilled, deionized water with 30 g $(NH_4)_2SO_4$ and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered.

SM3 Media: SM3 minimal media for *E. coli* contained per liter: 596.2 mL sterile distilled, deionized water, 2.0 mL of 100× Trace Metals Stock, 100 mL of 10× Ammonium Citrate 30 Salts, 3.6 mL of Phosphate Buffer, pH=6.8, 2 mL of 40 mM Fe(II) sulfate, 1.0 mL of 2M $MgSO_4$, 5.0 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare a 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10 Media: SM10 minimal media for *E. coli* contained per liter: 574.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Prepare a 1 M Potassium 3-(N-morpholino) propanesulfonic Acid (MOPS) and adjust to pH 7.4 with KOH (~40 mL). Filter sterilize (0.2 um) and store at room temperature in the dark. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10++ Media: SM10 minimal media for *E. coli* contained per liter: 549.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 25.0 mL of 100 g/L Yeast Extract and 25.0 mL of 100 g/L Casamino acids. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare a 1 M Potassium 3-(N-morpholino) propanesulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM3 Media: FGM3 media for *E. coli* contained per liter: 636.2 mL sterile distilled, deionized water, 2.0 mL of 100× Trace Metals Stock, 100 mL of 10× Ammonium Citrate 20 Salts, 3.6 mL of Phosphate Buffer, pH=6.8, 2 mL of 40 mM Fe(II) sulfate, 1.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine. Prepare 1 liter of 10× concentrated Ammonium-Citrate 20 salts by mixing 20 g of $(NH_4)_2SO_4$ and 1.5 g Citric Acid in water with stirring. Autoclave and store at room temperature. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM10 Media: FGM10 media for *E. coli* contained per liter: 824.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM 2M $CaSO_4$, 50 mL of 500 g/L glucose, and 0.2 mL of 1 mg/mL Thiamine. Prepare 1 liter of 10× concentrated Ammonium-Citrate 90 salts by mixing 90 g of $(NH_4)_2SO_4$ and 2.5 g Citric Acid Autoclave and store at room temperature. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

96WPM Media: 96WPM media for *E. coli* contained per liter: 638.8 mL sterile distilled, deionized water, 2.0 mL of 100× Trace Metals Stock, 100 mL of 10× Ammonium Citrate 30 Salts, 2 mL of 40 mM Fe(II) sulfate, 2.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

Antibiotic concentrations: Unless other wise stated standard final concentrations of antibiotic in media are kanamycin (35 ug/mL), ampicillin (100 ug/ml), spectinomycin (100 ug/ml), chloramphenicol (20 ug/ml), anhydrotetracycline (50 ng/ml), gentamicin (10 ug/ml), zeocin (50 ug/ml), blasticidin (50 ug/ml). Low salt medium such as low salt LB medium is used when using blasticidin or zeocin as selective antibiotics.

Subsection VI: Protocols for Production in *E. coli*

Shake Flask Protocol—1

Bioproduction is demonstrated at a 50-mL scale using GM25 minimal defined media without phosphate. Cultures are started from single colonies by standard practice into 50 mL of GM25 media containing 3.2 mM phosphate plus appropriate antibiotics and grown to stationary phase overnight at 30° C. with rotation at 200 rpm. The optical density ($OD_{600}$, 1 cm pathlength) of each stationary phase culture is measured and the entire culture is transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus appropriate antibiotic in triplicate 250-ml non-baffled flasks and incubated at 30° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by changing the temperature of the shaking incubator to 37° C. at 4 hours post-inoculation. A sample is collected at this time point as well as 6-, 8-, and 24-hours post-inoculation for optical density and product measurement.

Shake Flask Protocol—2

Bioproduction is demonstrated at a 50-mL scale in GM25 minimal defined media without phosphate. Cultures are started from single colonies by standard practice into 50 mL of GM25 media containing 3.2 mM phosphate plus appropriate antibiotic(s) and grown to stationary phase overnight at 37° C. with rotation at 200 rpm. The optical density ($OD_{600}$, 1 cm pathlength) of each stationary phase culture is measured and the entire culture was transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus antibiotics in triplicate 250-ml non-baffled flasks and incubated at 37° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by inducing the cultures using 50 ng/mL of anhydrotetracycline (aTc) at inoculation. A sample was collected at this time point as well as 4 and 20-hours post-inoculation for optical density and product measurement.

96 Well Plate Protocol—1

Bioproduction is demonstrated at µL in minimal medium. Colonies were used to inoculate individual wells in standard 96 well plates, filled with 150 µL of SM10++ medium with the appropriate antibiotics as needed. Plates were covered with sandwich covers (Model #CR1596 obtained from EnzyScreen, Haarlam, The Netherlands). These covers ensure minimal evaporative loss during incubation. To ensure adequate aeration, the inoculated 96 well plates and sandwich covers were clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model #CR1600, EnzyScreen, Haarlam, The Netherlands). Importantly, the shaker used had an orbit of 0.125 inches or 3 mm. This combination of orbit and minimal shaking speed is required to obtain needed mass transfer coefficient and enable adequate culture oxygenation. Cultures were grown for 16 hours.

After 16 hours of growth, 10 µL samples were taken to measure the optical density at 600 nm (OD(600 nm)). This was done using a plate spectrophotometer. Overnight cell densities at this point often range from 5-15 OD(600 nm). Cells from 100 µL of overnight growth in each well were pelleted by centrifugation, excess media was removed and cells were resuspended in 150 µL of 96WPM, which contains no phosphate. Subsequently cells were once again pelleted and again excess media was removed. Using the overnight measured optical densities, enough fresh 96WPM was added to each well, so upon re-suspension a final OD(600 nm) of 20 was obtained. 7.5 µL of the normalized and washed cultures of OD(600 nm)=20, was used to inoculate 150 µL of fresh 96WPM, plus appropriate antibiotics, in wells of a new standard 96 well plate. Plates were covered with sandwich covers (Model #CR1596 obtained from EnzyScreen, Haarlam, The Netherlands) and clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model #CR1600, EnzyScreen, Haarlam, The Netherlands). Cultures were incubated for 24 hours. After 16-24 hours of production, 100 µL samples from each well were pelleted by centrifugation and the supernatant collected for subsequent analytical analyes.

Micro24 Protocol—1

Bioproduction is demonstrated at mL scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 500 µL of washed and normalized cells was added to 500 µL of 30% sterile glycerol in water, mixed and frozen in cryovial (seed vials) at minus 80 degrees Celsius in a ultralow temperature freezer.

The Micro-24™ Microreactor system (Pall Corporation, Exton, Pa., USA) was used to evaluate strains at the mL scale. Pall 24-well PERC cassettes (Catalogue #MRT-PRC) were used for cell growth and production along with stainless steel check valve caps (Catalogue #MRT-CAP-E24). The experimental protocol was set up with an initial volume of 3 mL of FGM3 medium, with appropriate antibiotics as needed, and an agitation of 1000 rpm. pH control was initially turned off. The temperature was controlled at 37 degrees Celsius, with an environmental temperature of 35 degrees Celsius. Oxygen control was initially turned off with monitoring enabled. Frozen seed vials were thawed on ice and 150 µL was used to inoculate each 3 mL culture in each Micro24 cassette well. Samples were collected at inoculation and at regular intervals. Optical density of samples was measured at 600 nm, glucose using a YSI biochemistry analyzer was measured as described below. In addition, supernatants were collected for subsequent analytical analyses. pH control was turned on for each well at the point at which the culture's optical densities as measured at 600 nm was greater than 1.0. pH control was achieved with pressured ammonium hydroxide gas. In addition, oxygen control was turned on for each well when the dissolved oxygen reached below 60%. Glucose boluses of 10 g/L were added both 24 and 48 hours post inoculation using a sterile 500 g/L stock solution.

1 L Fermentation Protocol—1

Bioproduction is demonstrated at L scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 3.5 mL of washed and normalized cells was added to 3.5 mL of 30% sterile glycerol in water, mixed and frozen in cryovial (seed vials) at minus 80 degrees Celsius in a ultralow temperature freezer.

An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and $pO_2$ monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif. USA), including FISP cell free sampling probes, a Segmod 4800 and FlowFraction 96 well plate fraction collector.

Tanks were filled with 800 mL of FGM10 Medium, with enough phosphate to target a final *E. coli* biomass concentration close to 10 g dry cell weight per liter. Antibiotics were added as appropriate. Frozen seed vials were thawed on ice and 7 mL of seed culture was used to inoculate the tanks. After inoculation, tanks were controlled at 37 degrees Celsius and pH 6.8 using a 10M solution of sodium hydroxide solution as a titrant. The following oxygen control scheme was used to maintain a dissolved oxygen set point of 25%. First gas flow rate was increased from a minimum of 0.3 L/min of air to 0.8 L/min of air, subsequently, if more aeration was needed, agitation was increased from a minimum of 300 rpm to a maximum of 1000 rpm. Finally if more oxygen was required to achieve a 25% set point, oxygen supplementation was included using the integrated mass flow controllers. A constant concentrated sterile filtered glucose feed (500 g/L) was added to the tanks at a rate of 2 mL/hr, once agitation reached 800 rpm. Fermentation runs were extended for up to 70 hrs and samples automatically withdrawn every 2-4 hrs. Samples were saved for subsequent analytical analysis.

Subsection VII: Analytical Methods

Analytical Methods have been developed for all anticipated metabolites and products.

Quantification of Organic and Amino Acids

A reverse phase UPLC-MS/MS method was developed for the simultaneous quantification of organic and amino acids. Chromatographic separation was performed using an Acquity CSH $C_{18}$ column (100 mm×2.1 i.d., 1.7 µm; Waters Corp., Milford, Mass., USA) at 45 degrees C. The following eluents were used: solvent A: $H_2O$, 0.2% formic acid and 0.05% ammonium (v/v); solvent B: MeOH, 0.1% formic acid and 0.05% ammonium (v/v). The gradient elution was as follows: 0-0.2 min isocratic 5% B, 0.2-1.0 min linear from 5% to 90% B, 1.0-1.5 min isocratic 90% B, and 1.5-1.8 min linear from 90% to 5% B, with 1.8-3.0 min for initial conditions of 5% B for column equilibration. The flow rate remained constant at 0.4 ml/min. A 5 µl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). MS/MS parameters including MRM transitions were tuned for each analyte and are listed in Table 6 below. Adipic acid at a concentration of 36 mg/L was used as an internal standard for normalization in all samples. Peak integration and further analysis was performed using Mass Lynx v4.1 software. The linear range for all metabolites was 2-50 mg/L. Samples were diluted as needed to be within the accurate linear range.

TABLE 6

MS/MS parameters

| Analyte | Retention Time (min) | ESI Mode | MRM Transition(s) | Cone Voltage | Collision Energy |
| --- | --- | --- | --- | --- | --- |
| 3-hydroxypropionic Acid | 1.04 | − | 88.94→ 59.09 | 22 | 8 |
| Alanine | 0.63 | + | 89.95→ 44.08 | 15 | 9 |
| α-ketoglutaric Acid | 1.97 | − | 144.80→ 56.90 | 13 | 11 |
| Citric Acid | 1.76 | − | 190.87→ 110.92 | 25 | 11 |
| Fumaric Acid | 1.91 | − | 114.72→ 70.94 | 21 | 7 |
| Glutamic Acid | 0.67 | − | 145.89→ 102.02 | 29 | 11 |
| Glyoxylic Acid | 0.83 | − | 72.84→ 44.98 | 33 | 7 |
| Lactic Acid | 1.18 | − | 88.94→ 43.08 | 26 | 8 |
| Malic Acid | 1.06 | − | 132.80→ 70.98 | 27 | 13 |
| Malonic Acid | 1.45 | − | 102.85→ 59.09 | 15 | 9 |
| Mevalonic Acid | 1.85 | − | 146.91→ 59.03 | 23 | 11 |
| Pyruvic Acid | 1.81 | − | 87.00→ 43.05 | 20 | 7 |
| Succinic Acid | 1.72 | − | 116.74→ 72.96 | 25 | 11 |
| Itaconic Acid | 1.86 | + | 130.87→84.98 | 20 | 12 |
| Adipic Acid | 2.0 | + | 144.77→82.96 | 32 | 12 |

Quantification of 2,3 Butanediol Using Mass Spectrometry

A rapid UPLC-MS/MS method was developed for the quantification of 2,3 butanediol (2,3-BDO). Chromatographic separation was performed using an Acquity UPLC BEH $C_{18}$ column (50 mm×2.1 i.d., 1.7 µm; Waters Corp., Milford, Mass., USA) at 45 degrees C. Isopropanol with 0.1% formic acid and 0.05% ammonium (v/v) was used in an isocratic separation. A 5 µl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). An MRM transition for 2,3-BDO of 90.972→55.074 was used along with a cone voltage of 16V and Collision Energy of 10V, operating in ESI+ mode. Adipic acid at a concentration of 36 mg/L was used as an internal standard for normalization in all samples. The Adipic acid was measured in ESI−mode with an MRM transition of 144.77→82.96, a cone voltage of 32V and collision energy of 12 V. Both 2,3-BDO and adipic acid eluted at 0.38 minutes. Peak integration and further analysis was performed using Mass Lynx v4.1 software.

Quantification of Diols Using Refractive Index

A confirmatory HPLC method was developed for the quantification of 2,3 butanediol stereoisomers. Chromatographic separation was performed using a Biorad Aminex HPX-87H column (300×7.8 mm, 1.7 µm; Biorad, Hercules, Calif. USA). The isocratic separation was run at room temperature with 5 mM sulfuric acid as the mobile phase. The flow rate remained constant at 0.4 ml/min for 40 minutes after an injection. A 10 µl sample injection volume was used. Method development was carried out using standard aqueous stock solutions of analytes. Separations were performed using an Acquity H-Class UPLC integrated with an ESAT/IN refractive index (RI) detector. (Waters Corp., Milford, Mass. USA). Meso-2,3-butanediol eluted at 24.9 minutes, while (R,R)-2,3-butanediol eluted at 26.3 minutes. Peaks were integrated using Masslynx Software v4.1.

Quantification of Glucose

A YSI biochemistry analyzer, model 2950M (YSI Incorporated, Yellow Springs Ohio, USA) was used to routinely measure glucose concentrations as well as ethanol. The instrument was used according to manufacturer's instructions, using all reagents as supplied from YSI.

What is claimed:

1. A genetically modified microorganism comprising:
   a production pathway comprising at least one enzyme for producing of an isoprenoid product, and
   at least one synthetic metabolic valve characterized by both (i) silencing of gene expression of a gene encoding a first enzyme essential for growth of the genetically modified microorganism and (ii) proteolysis of a second enzyme essential for growth of the genetically modified microorganism,
   wherein under condition of depleting of a limiting nutrient from a growth media in which the genetically modified microorganism is growing will inducing a stationary or non-dividing cellular state; and
   wherein the synthetic metabolic valve of the microorganism is conditionally triggered;
   wherein the gene encoding the first enzyme essential for growth of the genetically modified microorganism is one of: enoyl-ACP reductase (fabI), citrate synthase (gltA), soluble transhydrogenase (udhA), glucose-6-phosphate-1-dehydrogenase (zwf), or lipoamide dehydrogenase (lpd), and combinations thereof; and
   wherein the second enzyme is one of: enoyl-ACP reductase (fabI), citrate synthase (gltA), soluble transhydrogenase (udhA), glucose-6-phosphate-1-dehydrogenase (zwf), or lipoamide dehydrogenase (lpd), and combinations thereof.

2. The genetically modified microorganism claim 1, further comprising expression a heterologous enzyme of a product production pathway and expression of the heterologous enzyme is conditional and/or coordinated with the conditional triggering of the synthetic metabolic valve.

3. The genetically modified microorganism claim 2, wherein the heterologous enzyme is one of: an acetoacetyl-CoA thiolase, hydroxymethylglutaryl-CoA synthase, hydroxymethylglutaryl-CoA reductase, mevalonate kinase, phosphomevalonate kinase, mevalonte diphosphate decarboxylase, isopentenyl-diphosphate isomerase, isoprene synthase and combinations thereof.

4. The genetically modified microorganism claim 2, wherein the heterologous enzymes are mvaE gene from *Enterococcus faecalis* and the mvaS gene, also from *E. faecalis*.

5. The genetically modified microorganism claim 1, wherein the production pathway comprises both increased expression of an acetyl-CoA carboxylase enzyme and increased expression of an enzyme of an isoprenoid production pathway.

6. The genetically modified microorganism of claim 1, further comprising a first or second enzyme essential for growth of the genetically modified microorganism that is one of: phosphoenolpyruvate carboxylase (ppc), succinyl- CoA synthetase (sucD), isocitrate lyase (aceA), ATP-dependent 6-phosphofructokinase (pfkA), ATP-dependent Lon proteinse (lon), sigma factor sigma-38 (rpoS), transketolase 1 (tktA), transketolast 2 (tktB), and combinations thereof.

7. The genetically modified microorganism of claim 1, wherein the synthetic metabolic valve comprises:
   (i) a gene encoding more than one small guide RNA specific for targeting more than one gene of an enzyme essential for growth of the genetically modified microorganism;
   (ii) a gene encoding a Cas9 or a gene encoding a dCAS9, and
   (iii) a gene encoding a proteolytic enzyme enhancing factor sspB.

8. The genetically modified microorganism claim 1, wherein the limiting nutrient of the growth media is a nutrient selected from the group: phosphate, nitrogen, sulfur, and magnesium, or any combinations thereof.

9. The genetically modified microorganism claim 1, wherein the genetically modified microorganism is additionally controlled by chemical inducer that is selected from a group: tetracycline, anhydrotetracycline, lactose, IPTG (isopropyl-beta-D-1-thiogalactopyranoside), arabinose, raffinose, and tryptophan, or combinations thereof.

10. The genetically modified microorganism of claim 1, wherein the genetically modified microorganism further comprises a disruption or deletion of a gene naturally occurring in the genetically modified microorganism and the gene is one of: a gene encoding lactate dehydrogenase (ldhA), phosphate acetyltransferase (pta), pyruvate oxidase (poxB), pyruvate-formate lyase (pflB), the methylglyoxal synthase (mgsA), acetate kinase (ackA), alcohol dehydrogenase (adhE), ATP-dependent Lon protease (lon), outer membrane protease (ompT), arcA transcriptional dual regulator (arcA), iclR transcriptional regulator (iclR), and any combinations thereof.

* * * * *

```
                        SEQUENCE LISTING

<160> NUMBER OF SEQ ID NOS: 54

<210> SEQ ID NO 1
<211> LENGTH: 3111
<212> TYPE: DNA
<213> ORGANISM: Artificial Sequence
<220> FEATURE:
<223> OTHER INFORMATION: Plasmid pSMART-HC-Kan-yibD-THNS

<400> SEQUENCE: 1
gtgcgtaatt gtgctgatct cttatatagc tgctctcatt atctctctac cctgaagtga      60
ctctctcacc tgtaaaaata atatctcaca ggcttaatag tttcttaata caaagcctgt     120
aaaacgtcag gataacttct gtgtaggagg ataatctatg gcaactctct gccgtccgtc     180
cgtgagtgtg ccggagcatg ttatcacgat ggaagaaacc cttgaactgg cccgtcgtcg     240
tcatacggat catccacagc tgcccctggc gctgcgctta attgaaaaca ccggtgttcg     300
cacgcgtcat attgttcaac cgatcgagga taccctggag catccagggt ttgaagatcg     360
caataaagta tacgagcgcg aggccaaatc gcgtgtgccg gcggtaatcc aacgcgccct     420
ggacgacgcg gagcttctgg cgacggacat tgacgttatt atctatgtct catgcacggg     480
ttttatgatg cctagtctta ctgcttggtt aatcaacgaa atgggcttcg acagcacgac     540
ccgccaaatt cctatcgcac agcttggctg tgcggccggt ggtgccgcga ttaaccgcgc     600
tcacgatttt tgcacggcat atcctgaagc aaatgcgctg atcgttgcct gcgaattctg     660
cagcctgtgt tatcagccca cagatctcgg tgtaggttct ctcctgtgca acggtctgtt     720
cggtgatgga attgctgcgg ctgtggtgcg cggacgtggt ggtacggggg ttcgcttgga     780
gcgtaacggc agctacttaa ttccaaaaac cgaagattgg atcatgtatg atgtgaaagc     840
aaccggtttc cacttcttac tggataagcg cgtcccggcc accatggaac ccttggcgcc     900
ggctctgaaa gaactcgcgg gcgagcatgg ttgggacgcc agtgatctgg atttttatat     960
tgttcacgcc ggtggtccgc gtattttaga cgacttgagt actttccttg aggtggatcc    1020
gcatgcgttt cgttttttccc gtgctaccct gaccgagtat ggtaacattg cgtcagcagt    1080
cgtgctggat gcgttacgcc gcttgttcga tgaaggcggt gtggaggaag gtgcgcgcgg    1140
tctgctggcg gggttcgggc aggtattac agccgaaatg tcactgggct gctggcaaac    1200
cgcgtagtaa ccggcttatc ggtcagtttc acctgattta cgtaaaaacc cgcttcggcg    1260 ggttttgct tttggagggg cagaaagatg aatgactgtc cacgacgcta tacccaaaag    1320
aaagacgaat tctctagata tcgctcaata ctgaccattt aaatcatacc tgacctccat    1380
agcagaaagt caaaagcctc cgaccggagg cttttgactt gatcggcacg taagaggttc    1440
caactttcac cataatgaaa taagatcact accgggcgta tttttttgagt tatcgagatt    1500 ttcaggagct aaggaagcta aaatgagcca tattcaacgg gaaacgtctt gctcgaggcc    1560
gcgattaaat tccaacatgg atgctgattt atatgggtat aaatgggctc gcgataatgt    1620
cgggcaatca ggtgcgacaa tctatcgatt gtatgggaag cccgatgcgc cagagttgtt    1680
tctgaaacat ggcaaaggta gcgttgccaa tgatgttaca gatgagatgg tcaggctaaa    1740
ctggctgacg gaatttatgc ctcttccgac catcaagcat tttatccgta ctcctgatga    1800
```

```
tgcatggtta ctcaccactg cgatcccagg aaaacagca ttccaggtat tagaagaata    1860
tcctgattca ggtgaaaata ttgttgatgc gctggcagtg ttcctgcgcc ggttgcattc    1920
gattcctgtt tgtaattgtc cttttaacgg cgatcgcgta tttcgtctcg ctcaggcgca    1980
atcacgaatg aataacggtt tggttggtgc gagtgatttt gatgacgagc gtaatggctg    2040
gcctgttgaa caagtctgga agaaatgca taagcttttg ccattctcac cggattcagt    2100
cgtcactcat ggtgatttct cacttgataa cctatttttt gacgagggga aattaatagg    2160
ttgtattgat gttggacgag tcggaatcgc agaccgatac caggatcttg ccatcctatg    2220
gaactgcctc ggtgagtttt ctccttcatt acagaaacgg cttttcaaa aatatggtat    2280 tgataatcct gatatgaata aattgcagtt tcacttgatg ctcgatgagt ttttctaatg    2340
agggcccaaa tgtaatcacc tggctcacct tcggtgggc cttctgcgt tgctggcgtt    2400 tttccatagg ctccgcccc ctgacgagca tcacaaaaat cgatgctcaa gtcagaggtg    2460
gcgaaacccg acaggactat aaagatacca ggcgtttccc cctggaagct ccctcgtgcg    2520
ctctcctgtt ccgaccctgc cgcttaccgg atacctgtcc gcctttctcc cttcgggaag    2580
cgtggcgctt tctcatagct cacgctgtag gtatctcagt tcggtgtagg tcgttcgctc    2640
caagctgggc tgtgtgcacg aaccccccgt tcagcccgac cgctgcgcct tatccggtaa    2700
ctatcgtctt gagtccaacc cggtaagaca cgacttatcg ccactggcag cagccactgg    2760
taacaggatt agcagagcga ggtatgtagg cggtgctaca gagttcttga agtggtggcc    2820
taactacggc tacactagaa gaacagtatt tggtatctgc gctctgctga agccagttac    2880
ctcggaaaaa gagttggtag ctcttgatcc ggcaaacaaa ccaccgctgg tagcggtggt    2940 tttttgttt gcaagcagca gattacgcgc agaaaaaaag gatctcaaga agatcctttg    3000
attttctacc gaagaaggc ccacccgtga aggtgagcca gtgagttgat tgcagtccag    3060
ttacgctgga gtctgaggct cgtcctgaat gatatcaagc ttgaattcgt t           3111
```

<210> SEQ ID NO 2
<211> LENGTH: 2386
<212> TYPE: DNA
<213> ORGANISM: Artificial Sequence
<220> FEATURE:
<223> OTHER INFORMATION: Plasmid pCDF-T2-fabIsgRNA

<400> SEQUENCE: 2

```
gcactgaaat ctagagcggt tcagtagaaa agatcaaagg atcttcttga gatcctttt     60 ttctgcgcgt aatcttttgc cctgtaaacg aaaaaaccac ctggggaggt ggtttgatcg    120
aaggttaagt cagttgggga actgcttaac cgtggtaact ggctttcgca gagcacagca    180
accaaatctg tccttccagt gtagccggac tttggcgcac acttcaagag caaccgcgtg    240
tttagctaaa caaatcctct gcgaactccc agttaccaat ggctgctgcc agtggcgttt    300
taccgtgctt ttccggggttg gactcaagtg aacagttacc ggataaggcg cagcagtcgg    360
gctgaacggg gagttcttgc ttacagccca gcttggagcg aacgacctac accgagccga    420
gataccagtg tgtgagctat gagaaagcgc cacacttccc gtaagggaga aaggcggaac    480
aggtatccgg taaacggcag ggtcggaaca ggagagcgca agaggggagcg accccgccgga    540 aacggtgggg atctttaagt cctgtcgggt ttcgcccgta ctgtcagatt catggttgag    600
cctcacggct cccacagatg caccggaaaa gcgtctgttt atgtgaactc tggcaggagg    660
gcggagccta tggaaaaacg ccaccggcgc ggccctgctg ttttgccttca catgttagtc    720 ccctgcttat ccacggaatc tgtgggtaac tttgtatgtg tccgcagcgc ccgccgcagt    780
```

```
ctcacgcccg gagcgtagcg accgagtgag ctagctattt gtttattttt ctaaatacat      840
tcaaatatgt atccgctcat gagacaataa ccctgataaa tgcttcaata atattgaaaa      900
aggaagagta tgagggaagc ggtgatcgcc aagtatcga ctcaactatc agaggtagtt       960
ggcgtcatcg agcgccatct cgaaccgacg ttgctggccg tacatttgta cggctccgca     1020
gtggatggcg gcctgaagcc acacagtgat attgatttgc tggttacggt gaccgtaagg     1080
cttgatgaaa caacgcggcg agctttgatc aacgaccttt tggaaacttc ggcttcccct     1140
ggagagagcg agattctccg cgctgtagaa gtcaccattg ttgtgcacga cgacatcatt     1200
ccgtggcgtt atccagctaa gcgcgaactg caatttggag aatggcagcg caatgacatt     1260
cttgcaggta tcttcgagcc agccacgatc gacattgatc tggctatctt gctgacaaaa     1320
gcaagagaac atagcgttgc cttggtaggt ccagcggcgg aggaactctt tgatccggtt     1380
cctgaacagg atctatttga ggcgctaaat gaaaccttaa cgctatggaa ctcgccgccc     1440
gactgggctg gcgatgagcg aaatgtagtg cttacgttgt cccgcatttg gtacagcgca     1500
gtaaccggca aaatcgcgcc aaggatgtc gctgccgact gggcaatgga gcgcctgccg     1560
gcccagtatc agcccgtcat acttgaagct agacaggctt atcttggaca agaagaagat     1620
cgcttggcct cgcgcgcaga tcagttggaa gaatttgtcc actacgtgaa aggcgagatc     1680
accaaggtag tcggcaaata atgtctaaca attcgttcaa cactataggg cgaattgaag     1740
gaaggccgtc aaggccgcat tgaggctcgt cctgaatgat atcaagcttg aattcgttga     1800
attctaaaga tctttgacag ctagctcagt cctaggtata atactagtca gcctgctccg     1860
gtcggaccgt tttagagcta gaaatagcaa gttaaaataa ggctagtccg ttatcaactt     1920
gaaaaagtgg caccgagtcg gtgcttttttt tgaagcttgg gcccgaacaa aaactcatct     1980
cagaagagga tctgaatagc gccgtcgacc atcatcatca tcatcattga gtttaaacgg     2040
tctccagctt ggctgttttg gcggatgaga agattttc agcctgatac agattaaatc      2100
agaacgcaga agcggtctga taaaacagaa tttgcctggc ggcagtagcg cggtggtccc     2160
acctgacccc atgccgaact cagaagtgaa acgccgtagc gccgatggta gtgtggggtc     2220
tccccatgcg agagtaggga actgccaggc atcaaataaa acgaaaggct cagtcgaaag     2280
actgggcctt tcgttttatc tgttgtttgt cggtgaactg gatccttact cgagtctaga     2340
ctgcagctgg gcctcatggg ccttcctttc actgcccgct ttccag                   2386
```

<210> SEQ ID NO 3
<211> LENGTH: 7413
<212> TYPE: DNA
<213> ORGANISM: Artificial Sequence
<220> FEATURE:
<223> OTHER INFORMATION: Plasmid pdCas9-ptet-sspB

<400> SEQUENCE: 3

```
gacgtcttaa gacccacttt cacatttaag ttgttttttct aatccgcata tgatcaattc      60
aaggccgaat aagaaggctg ctctgcacc ttggtgatca ataattcga tagcttgtcg       120 taataatggc ggcatactat cagtagtagg tgtttccctt tcttctttag cgacttgatg      180
ctcttgatct tccaatacgc aacctaaagt aaaatgcccc acagcgctga gtgcatataa      240
tgcattctct agtgaaaaac cttgttggca taaaaggct aattgatttt cgagagtttc       300
atactgtttt tctgtaggcc gtgtacctaa atgtactttt gctccatcgc gatgacttag      360
taaagcacat ctaaaacttt tagcgttatt acgtaaaaaa tcttgccagc tttccccttc      420
```

```
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat cattaattcc taatttttgt tgacactcta    660
tcgttgatag agttatttta ccactcccta tcagtgatag agaaaagaat tcaaaagatc    720
taaagaggag aaaggatcta tggataagaa atactcaata ggcttagcta tcggcacaaa    780
tagcgtcgga tgggcggtga tcactgatga atataaggtt ccgtctaaaa agttcaaggt    840
tctgggaaat acagaccgcc acagtatcaa aaaaatctt ataggggctc ttttatttga    900
cagtggagag acagcggaag cgactcgtct caaacggaca gctcgtagaa ggtatacacg    960
tcggaagaat cgtatttgtt atctacagga gattttttca aatgagatgg cgaaagtaga   1020
tgatagtttc tttcatcgac ttgaagagtc ttttttggtg gaagaagaca agaagcatga   1080
acgtcatcct atttttggaa atatagtaga tgaagttgct tatcatgaga aatatccaac   1140
tatctatcat ctgcgaaaaa aattggtaga ttctactgat aaagcggatt tgcgcttaat   1200
ctatttggcc ttagcgcata tgattaagtt tcgtggtcat ttttttgattg agggagattt   1260
aaatcctgat aatagtgatg tggacaaact atttatccag ttggtacaaa cctacaatca   1320
attatttgaa gaaaacccta ttaacgcaag tggagtagat gctaaagcga ttctttctgc   1380
acgattgagt aaatcaagac gattagaaaa tctcattgct cagctccccg gtgagaagaa   1440
aaatggctta tttgggaatc tcattgcttt gtcattgggt ttgaccccta attttaaatc   1500
aaattttgat ttggcagaag atgctaaatt acagctttca aaagatactt acgatgatga   1560
tttagataat ttattggcgc aaattggaga tcaatatgct gatttgtttt tggcagctaa   1620
gaatttatca gatgctattt tactttcaga tatcctaaga gtaaatactg aaataactaa   1680
ggctccccta tcagcttcaa tgattaaacg ctacgatgaa catcatcaag acttgactct   1740
tttaaaagct ttagttcgac aacaacttcc agaaaagtat aaagaaatct tttttgatca   1800
atcaaaaaac ggatatgcag gttatattga tgggggagct agccaagaag aattttataa   1860
atttatcaaa ccaattttag aaaaaatgga tggtactgag gaattattgg tgaaactaaa   1920
tcgtgaagat ttgctgcgca agcaacggac ctttgacaac ggctctattc cccatcaaat   1980
tcacttgggt gagctgcatg ctattttgag aagacaagaa gacttttatc catttttaaa   2040
agacaatcgt gagaagattg aaaaaatctt gacttttcga attccttatt atgttggtcc   2100
attggcgcgt ggcaatagtc gttttgcatg gatgactcgg aagtctgaag aaacaattac   2160
cccatggaat tttgaagaag ttgtcgataa aggtgcttca gctcaatcat ttattgaacg   2220
catgacaaac tttgataaaa atcttccaaa tgaaaaagta ctaccaaaac atagtttgct   2280
ttatgagtat tttacggttt ataacgaatt gacaaaggtc aaatatgtta ctgaaggaat   2340
gcgaaaacca gcatttcttt caggtgaaca gaagaaagcc attgttgatt tactcttcaa   2400
aacaaatcga aaagtaaccg ttaagcaatt aaaagagaat tatttcaaaa aaatagaatg   2460
ttttgatagt gttgaaattt caggagttga agatagattt aatgcttcat taggtaccta   2520
ccatgatttg ctaaaaatta ttaaagataa agattttttg gataatgaag aaaatgaaga   2580
tatcttagag gatattgttt taacattgac cttatttgaa gatagggaga tgattgagga   2640
aagacttaaa acatatgctc acctctttga tgataaggtg atgaaacagc ttaaacgtcg   2700
ccgttatact ggttggggac gtttgtctcg aaaattgatt aatggtatta gggataagca   2760
atctggcaaa acaatattag attttttgaa atcagatggt tttgccaatc gcaattttat   2820
```

```
gcagctgatc catgatgata gtttgacatt taaagaagac attcaaaaag cacaagtgtc    2880
tggacaaggc gatagtttac atgaacatat tgcaaattta gctggtagcc ctgctattaa    2940
aaaaggtatt ttacagactg taaaagttgt tgatgaattg gtcaaagtaa tggggcggca    3000
taagccagaa aatatcgtta ttgaaatggc acgtgaaaat cagacaactc aaaagggcca    3060
gaaaaattcg cgagagcgta tgaaacgaat cgaagaaggt atcaaagaat taggaagtca    3120
gattcttaaa gagcatcctg ttgaaaatac tcaattgcaa aatgaaaagc tctatctcta    3180
ttatctccaa aatggaagag acatgtatgt ggaccaagaa ttagatatta atcgtttaag    3240
tgattatgat gtcgatgcca ttgttccaca aagtttcctt aaagacgatt caatagacaa    3300
taaggtctta acgcgttctg ataaaaatcg tggtaaatcg ataacgttc caagtgaaga    3360 agtagtcaaa aagatgaaaa actattggag acaacttcta aacgccaagt taatcactca    3420
acgtaagttt gataatttaa cgaaagctga acgtggaggt ttgagtgaac ttgataaagc    3480
tggttttatc aaacgccaat tggttgaaac tcgccaaatc actaagcatg tggcacaaat    3540
tttggatagt cgcatgaata ctaaatacga tgaaaatgat aaacttattc gagaggttaa    3600
agtgattacc ttaaaatcta aattagtttc tgacttccga aaagatttcc aattctataa    3660
agtacgtgag attaacaatt accatcatgc ccatgatgcg tatctaaatg ccgtcgttgg    3720
aactgctttg attaagaaat atccaaaact tgaatcggag tttgtctatg gtgattataa    3780
agtttatgat gttcgtaaaa tgattgctaa gtctgagcaa gaaataggca aagcaaccgc    3840
aaaatatttc ttttactcta atatcatgaa cttcttcaaa acagaaatta cacttgcaaa    3900
tggagagatt cgcaaacgcc ctctaatcga aactaatggg gaaactggag aaattgtctg    3960
ggataaaggg cgagattttg ccacagtgcg caaagtattg tccatgcccc aagtcaatat    4020
tgtcaagaaa acagaagtac agacaggcgg attctccaag gagtcaattt taccaaaaag    4080
aaattcggac aagcttattg ctcgtaaaaa agactgggat ccaaaaaaat atggtggttt    4140
tgatagtcca acggtagctt attcagtcct agtggttgct aaggtggaaa agggaaatc    4200 gaagaagtta aaatccgtta aagagttact agggatcaca attatggaaa gaagttcctt    4260
tgaaaaaaat ccgattgact ttttagaagc taaaggatat aaggaagtta aaaaagactt    4320
aatcattaaa ctacctaaat atagtctttt tgagttagaa aacggtcgta acggatgct    4380 ggctagtgcc ggagaattac aaaaaggaaa tgagctggct ctgccaagca aatatgtgaa    4440
ttttttatat ttagctagtc attatgaaaa gttgaagggt agtccagaag ataacgaaca    4500
aaaacaattg tttgtggagc agcataagca ttatttagat gagattattg agcaaatcag    4560
tgaattttct aagcgtgtta ttttagcaga tgccaattta gataaagttc ttagtgcata    4620
taacaaacat agagacaaac caatacgtga acaagcagaa aatattattc atttatttac    4680
gttgacgaat cttggagctc ccgctgcttt taaatatttt gatacaacaa ttgatcgtaa    4740
acgatatacg tctacaaaag aagttttaga tgccactctt atccatcaat ccatcactgg    4800
tctttatgaa acacgcattg atttgagtca gctaggaggt gactaactcg agccggctta    4860
tcggtcagtt tcacctgatt tacgtaaaaa cccgcttcgg cgggttttg cttttggagg    4920 ggcagaaaga tgaatgactg tccacgacgc tatcccaaa agaaatccct atcagtgata    4980
gagattgaca tccctatcag tgatagagat actgagcaca tcagcaggac gcactgacca    5040
agaggagaaa ggatctatgg atttgtcaca gctaacacca cgtcgtccct atctgctgcg    5100
tgcattctat gagtggttgc tggataacca gctcacgccg cacctggtgg tggatgtgac    5160
```

```
gctccctggc gtgcaggttc ctatggaata tgcgcgtgac gggcaaatcg tactcaacat   5220
tgcgccgcgt gctgtcggca atctggaact ggcgaatgat gaggtgcgct ttaacgcgcg   5280
ctttggtggc attccgcgtc aggtttctgt gccgctggct gccgtgctgg ctatctacgc   5340
ccgtgaaaat ggcgcaggca cgatgtttga gcctgaagct gcctacgatg aagataccag   5400
catcatgaat gatgaagagg catcggcaga caacgaaacc gttatgtcgg ttattgatgg   5460
cgacaagcca gatcacgatg atgacactca tcctgacgat gaacctccgc agccaccacg   5520
cggtggtcga ccggcattac gcgttgtgaa gtaactcgag taaggatctc caggcatcaa   5580
ataaaacgaa aggctcagtc gaaagactgg gcctttcgtt ttatctgttg tttgtcggtg   5640
aacgctctct actagagtca cactggctca ccttcgggtg ggcctttctg cgtttatacc   5700
tagggatata ttccgcttcc tcgctcactg actcgctacg ctcggtcgtt cgactgcggc   5760
gagcggaaat ggcttacgaa cggggcggag atttcctgga agatgccagg aagatactta   5820
acagggaagt gagagggccg cggcaaagcc gttttttccat aggctccgcc ccctgacaa   5880
gcatcacgaa atctgacgct caaatcagtg gtggcgaaac ccgacaggac tataaagata   5940
ccaggcgttt ccccctggcg gctccctcgt gcgctctcct gttcctgcct ttcggtttac   6000
cggtgtcatt ccgctgttat ggccgcgttt gtctcattcc acgcctgaca ctcagttccg   6060
ggtaggcagt tcgctccaag ctggactgta tgcacgaacc ccccgttcag tccgaccgct   6120
gcgccttatc cggtaactat cgtcttgagt ccaacccgga agacatgca aaagcaccac   6180
tggcagcagc cactggtaat tgatttagag gagttagtct tgaagtcatg cgccggttaa   6240
ggctaaactg aaaggacaag ttttggtgac tgcgctcctc caagccagtt acctcggttc   6300
aaagagttgg tagctcagag aaccttcgaa aaaccgccct gcaaggcggt tttttcgttt   6360
tcagagcaag agattacgcg cagaccaaaa cgatctcaag aagatcatct tattaatcag   6420
ataaaatatt tctagatttc agtgcaattt atctcttcaa atgtagcacc tgaagtcagc   6480
cccatacgat ataagttgtt actagtgctt ggattctcac caataaaaaa cgcccggcgg   6540
caaccgagcg ttctgaacaa atccagatgg agttctgagg tcattactgg atctatcaac   6600
aggagtccaa gcgagctcga tatcaaatta cgccccgccc tgccactcat cgcagtactg   6660
ttgtaattca ttaagcattc tgccgacatg gaagccatca caaacggcat gatgaacctg   6720
aatcgccagc ggcatcagca ccttgtcgcc ttgcgtataa tatttgccca tggtgaaaac   6780
gggggcgaag aagttgtcca tattggccac gtttaaatca aaactggtga actcaccca   6840
gggattggct gagacgaaaa acatattctc aataaaccct ttagggaaat aggccaggtt   6900
ttcaccgtaa cacgccacat cttgcgaata tatgtgtaga actgccgga atcgtcgtg   6960
gtattcactc cagagcgatg aaaacgtttc agtttgctca tggaaaacgg tgtaacaagg   7020
gtgaacacta tcccatatca ccagctcacc gtctttcatt gccatacgaa attccggatg   7080
agcattcatc aggcgggcaa gaatgtgaat aaaggccgga taaaacttgt gcttattttt   7140
ctttacggtc tttaaaaagg ccgtaatatc cagctgaacg gtctggttat aggtacattg   7200
agcaactgac tgaaatgcct caaaatgttc tttacgatgc cattgggata tatcaacggt   7260
ggtatatcca gtgatttttt tctccatttt agcttcctta gctcctgaaa atctcgataa   7320
ctcaaaaat acgcccggta gtgatcttat ttcattatgg tgaaagttgg aacctcttac   7380
gtgccgatca acgtctcatt ttcgccagat atc                               7413
```

<210> SEQ ID NO 4
<211> LENGTH: 974

```
<212> TYPE: DNA
<213> ORGANISM: Artificial Sequence
<220> FEATURE:
<223> OTHER INFORMATION: Synthetic Construct Delta-cas3::ugpBp-sspB-proB

<400> SEQUENCE: 4
caagacatgt gtatatcact gtaattcgat atttatgagc agcatcgaaa aatagcccgc      60
tgatatcatc gataatacta aaaaaacagg gaggctatta ccaggcatca ataaaacga      120 aaggctcagt cgaaagactg ggcctttcgt tttatctgtt gtttgtcggt gaacgctctc    180
tactagagtc acactggctc accttcgggt gggcctttct gcgtttatat ctttctgaca    240
ccttactatc ttacaaatgt aacaaaaaag ttatttttct gtaattcgag catgtcatgt    300
taccccgcga gcataaaacg cgtgtgtagg aggataatct atggatttgt cacagctaac    360
accacgtcgt ccctatctgc tgcgtgcatt ctatgagtgg ttgctggata accagctcac    420
gccgcacctg gtggtggatg tgacgctccc tggcgtgcag gttcctatgg aatatgcgcg    480
tgacgggcaa atcgtactca acattgcgcc gcgtgctgtc ggcaatctgg aactggcgaa    540
tgatgaggtg cgctttaacg cgcgctttgg tggcattccg cgtcaggttt ctgtgccgct    600
ggctgccgtg ctggctatct acgcccgtga aatggcgca  gcacgatgt ttgagcctga    660 agctgcctac gatgaagata ccagcatcat gaatgatgaa gaggcatcgg cagacaacga    720
aaccgttatg tcggttattg atggcgacaa gccagatcac gatgatgaca ctcatcctga    780
cgatgaacct ccgcagccac cacgcggtgg tcgaccggca ttacgcgttg tgaagtaatt    840
gacggctagc tcagtcctag gtacagtgct agccatatga aggagaacaa atgaatttgc    900
ttattgataa ctggatccct gtacgcccgc gaaacggggg gaaagtccaa atcataaatc    960
tgcaatcgct atac                                                      974

<210> SEQ ID NO 5
<211> LENGTH: 1500
<212> TYPE: DNA
<213> ORGANISM: Artificial Sequence
<220> FEATURE:
<223> OTHER INFORMATION: Linear DNA Construct Delta-ptsG::proC-glk

<400> SEQUENCE: 5
ggctgtgttg aaaggtgttg ccgttgaaga actggcgcag gtaaccaccg ataacttcgc      60
ccgtctgttt cacatcgacg cttcccgcct tcaatccatc cgttgaatga gttttttaa      120 agctcgtaat taatacttcg ctcttcatgc cgccgcaaac cccgcccctg acagggcggg    180
gtttcgccgc acgtctccat cgcttgccca agttgtgaag cacagctaac accacgtcgt    240
ccctatctgc tgccctaggt ctatgagtgg ttgctggata actttacggg catgcataag    300
gctcgtatga tatattcagg gagaccacaa cggtttccct ctacaaataa ttttgtttaa    360
ctttcgtaga agagcacttc cacacttctg gaaaaaggag atataccatg accaagtatg    420
ccctggtcgg tgacgtaggt ggtaccaatg cacgtctcgc tctctgtgat atcgcaagcg    480
gggaaatttc tcaggccaaa acatattccg ggttggatta ccccagctta gaagccgtga    540
ttcgtgtcta tttagaagaa cataaagtag aagtcaaaga cggttgtatt gctattgcgt    600
gccccatcac tggggattgg gtagcaatga ccaaccatac ctgggcgttt tctattgccg    660
agatgaaaaa aaatctgggt ttctcacacc tggagatcat caacgatttt accgcggtga    720
gcatggcgat cccaatgtta aaaaaggaac acttaattca gttcggcggg gcagaacctg    780
tggagggcaa gccgatcgcg gtttatggtg caggcacagg cttaggtgtc gcgcacttgg    840
```

```
tacatgttga caagcgctgg gtgagtttgc cgggcgaagg cggccacgtg gattttgccc    900
ccaattctga agaggaggcg attattctgg aaatcttgcg tgcagaaatc ggtcatgtgt    960
ctgccgaacg tgtgctgagt ggtccaggtc tggtgaatct gtaccgcgct attgtcaaag   1020
cggataaccg cctgccagaa aaccttaaac cgaaagatat caccgaacgt gccttggccg   1080
actcctgtac cgattgccgc cgcgcactta gtctgttttg cgttatcatg ggtcgttttg   1140
gcggcaacct cgcgctgaac ctggggacct tggcggtgt tttatttgcg ggaggtattg    1200
ttccacgctt tttagaattt ttcaaagcca gtggctttcg cgcggccttc gaagacaagg   1260
gacgttttaa agaatacgta catgatatcc cagtctattt aattgttcac gataacccag   1320
gactgttagg ctctggtgcc catctgcgtc agacattggg ccatattctg taatccgtaa   1380
gacgttgggg agactaaggc agccagatgg ctgccttttt tacaggtgtt attcagaatt   1440
gatacgtgcc ggtaatgctg aaattacgcg gtgtgccgta gacgatagaa ccttccacgt   1500
```

<210> SEQ ID NO 6
<211> LENGTH: 1332
<212> TYPE: DNA
<213> ORGANISM: Artificial Sequence
<220> FEATURE:
<223> OTHER INFORMATION: Linear DNA Construct proC-galP

<400> SEQUENCE: 6

```
tatgtcgcga aaacatcgt tgctgctggc ctggccgatc gttgtgaaat tcaggtttcc      60
tacgcaatcg gcgtggctga accgacctcc atcatggtag aaactttcgg tactgagaaa    120
gtgccttctg aacaactgac cctgctggta cgtgagttct tcgacctgcg cccatacggt    180
ctgattcaga tgctggatct gctgcacccg atctacaaag aaaccgcagc atacggtcac    240
tttggtcgtg aacatttccc gtgggaaaaa accgacaaag cgcagctgct gcgcgatgct    300
gccggtctga gtaatctttt cttcacctgc gttcaaagga cttcgctctt catgccgccg    360
caaaccccgc ccctgacagg gcggggtttc gccgcacgtc tccatcgctt gcccaagttg    420
tgaagcacag ctaacaccac gtcgtcccta tctgctgccc taggtctatg agtggttgct    480
ggataacttt acgggcatgc ataaggctcg tatgatatat tcagggagac cacaacggtt    540
tccctctaca aataattttg tttaactttc gtagaagagc acttccacac ttctggaaaa    600
aggagatata ccatgccaga tgccaaaaag caaggccgtt ctaacaaggc aatgacattc    660
ttcgtgtgct tccttgcggc gcttgccggc ctcttgttcg gcttggacat cggcgtcatt    720
gccggtgctt taccattat cgctgacgaa ttccagatca cctcgcacac gcaagaatgg    780
gtcgtaagct ccatgatgtt cggtgcggca gtcggtgcgg tgggcagcgg ctggctctcc    840
tttaaactcg ggcgcaaaaa gagcctgatg atcggcgcaa ttttgtttgt tgccggttcg    900
ctgttctctg cggctgcgcc aaacgttgaa gtactgattc tttcccgcgt tctactgggg    960
ctggcggtgg gtgtggcctc ttataccgca ccgctgtacc tctctgaaat tgcgccggaa   1020
aaaattcgtg gcagtatgat ctcgatgtat cagttgatga tcactatcgg gatcctcggt   1080
gcttatcttt ctgataccgc cttcagctac accggtgcat ggcgctggat gctgggtgtg   1140
attatcatcc cggcaatttt gctgctgatt ggtgtcttct tcctgccaga cagcccacgt   1200
tggtttgccg ccaaacgccg ttttgttgat gccgaacgcg tgctgctacg cctgcgtgac   1260
accagcgcgg aagcgaaacg cgaactggat gaaatccgtg aaagtttgca ggttaaacag   1320
agtggctggg cg                                                       1332
```

<210> SEQ ID NO 7
<211> LENGTH: 970
<212> TYPE: DNA
<213> ORGANISM: Artificial Sequence
<220> FEATURE:
<223> OTHER INFORMATION: fabI-DAS+4:gentR

<400> SEQUENCE: 7

```
ctattgaaga tgtgggtaac tctgcggcat tcctgtgctc cgatctctct gccggtatct      60
ccggtgaagt ggtccacgtt gacggcggtt tcagcattgc tgcaatgaac gaactcgaac     120
tgaaagcggc caacgatgaa aactattctg aaaactatgc ggatgcgtct aataggaag      180
ttcctattct ctagaaagta taggaacttc cgaatccatg tgggagttta ttcttgacac     240
agatatttat gatataataa ctgagtaagc ttaacataag gaggaaaaac atatgttacg     300
cagcagcaac gatgttacgc agcagggcag tcgccctaaa acaaagttag gtggctcaag     360
tatgggcatc attcgcacat gtaggctcgg ccctgaccaa gtcaaatcca tgcgggctgc     420
tcttgatctt ttcggtcgtg agttcggaga cgtagccacc tactcccaac atcagccgga     480
ctccgattac ctcgggaact tgctccgtag taagacattc atcgcgcttg ctgccttcga     540
ccaagaagcg gttgttggcg ctctcgcggc ttacgttctg cccaagtttg agcagccgcg     600
tagtgagatc tatatctatg atctcgcagt ctccggcgag caccggaggc agggcattgc     660
caccgcgctc atcaatctcc tcaagcatga ggccaacgcg cttggtgctt atgtgatcta     720
cgtgcaagca gattacggtg acgatcccgc agtggctctc tatacaaagt gggcatacg     780
ggaagaagtg atgcactttg atatcgaccc aagtaccgcc acctaagaag ttcctattct     840
ctagaaagta taggaacttc cgttctgttg gtaaagatgg gcggcgttct gccgcccgtt     900
atctctgtta taccttctg atatttgtta tcgccgatcc gtctttctcc ccttcccgcc     960
ttgcgtcagg                                                            970
```

<210> SEQ ID NO 8
<211> LENGTH: 1026
<212> TYPE: DNA
<213> ORGANISM: Artificial Sequence
<220> FEATURE:
<223> OTHER INFORMATION: lpd-DAS+4:gentR

<400> SEQUENCE: 8

```
ggtactaacg gcggcgagct gctgggtgaa atcggcctgg caatcgaaat gggttgtgat      60
gctgaagaca tcgcactgac catccacgcg caccgactc tgcacgagtc tgtgggcctg      120
gcggcagaag tgttcgaagg tagcattacc gacctgccga acccgaaagc gaagaagaag     180
gcggccaacg atgaaaacta ttctgaaaac tatgcggatg cgtcttaata gcgaatccat     240
gtgggagttt attcttgaca cagatattta tgatataata actgagtaag cttaacataa     300
ggaggaaaaa catatgttac gcagcagcaa cgatgttacg cagcagggca gtcgccctaa     360
aacaaagtta ggtggctcaa gtatgggcat cattcgcaca tgtaggctcg gcctgacca    420
agtcaaatcc atgcgggctg ctcttgatct tttcggtcgt gagttcggag acgtagccac     480
ctactcccaa catcagccgg actccgatta cctcgggaac ttgctccgta gtaagacatt     540
catcgcgctt gctgccttcg accaagaagc ggttgttggc gctctcgcgg cttacgttct     600
gcccaagttt gagcagccgc gtagtgagat ctatatctat gatctcgcag tctccggcga     660
gcaccggagg cagggcattg ccaccgcgct catcaatctc ctcaagcatg aggccaacgc     720
gcttggtgct tatgtgatct acgtgcaagc agattacggt gacgatcccg cagtggctct     780
```

```
ctatacaaag ttgggcatac gggaagaagt gatgcacttt gatatcgacc caagtaccgc    840
cacctaattt ttcgtttgcc ggaacatccg gcaattaaaa aagcggctaa ccacgccgct    900
ttttttacgt ctgcaattta cctttccagt cttcttgctc cacgttcaga gagacgttcg    960
catactgctg accgttgctc gttattcagc ctgacagtat ggttactgtc gtttagacgt   1020
tgtggg                                                              1026
```

<210> SEQ ID NO 9
<211> LENGTH: 869
<212> TYPE: DNA
<213> ORGANISM: Artificial Sequence
<220> FEATURE:
<223> OTHER INFORMATION: gltA-DAS+4:zeoR

<400> SEQUENCE: 9

```
gtattccgtc ttccatgttc accgtcattt tcgcaatggc acgtaccgtt ggctggatcg     60
cccactggag cgaaatgcac agtgacggta tgaagattgc ccgtccgcgt cagctgtata    120
caggatatga aaacgcgac tttaaaagcg atatcaagcg tgcggccaac gatgaaaact    180
attctgaaaa ctatgcggat gcgtcttaat agttgacaat taatcatcgg catagtatat    240
cggcatagta taatacgact cactatagga gggccatcat ggccaagttg accagtgccg    300
ttccggtgct caccgcgcgc gacgtcgccg gagcggtcga gttctggacc gaccggctcg    360
ggttctcccg ggacttcgtg gaggacgact cgccggtgt ggtccgggac gacgtgaccc    420
tgttcatcag cgcggtccag gaccaggtgg tgccggacaa caccctggcc tgggtgtggg    480
tgcgcggcct ggacgagctg tacgccgagt ggtcggaggc cgtgtccacg aacttccggg    540
acgcctccgg gccggccatg accgagatcg cgagcagcc gtgggggcgg gagttcgccc    600
tgcgcgaccc ggccggcaac tgcgtgcact tgtggcaga ggagcaggac tgaggataag    660
taatggttga ttgctaagtt gtaaatattt taacccgccg ttcatatggc gggttgattt    720
ttatatgcct aaacacaaaa aattgtaaaa ataaaatcca ttaacagacc tatatagata    780
tttaaaaaga atagaacagc tcaaattatc agcaacccaa tactttcaat taaaaacttc    840
atggtagtcg catttataac cctatgaaa                                      869
```

<210> SEQ ID NO 10
<211> LENGTH: 852
<212> TYPE: DNA
<213> ORGANISM: Artificial Sequence
<220> FEATURE:
<223> OTHER INFORMATION: udhA-DAS+4:bsdR

<400> SEQUENCE: 10

```
tctgggtatt cactgctttg gcgagcgcgc tgccgaaatt attcatatcg gtcaggcgat     60
tatggaacag aaaggtggcg gcaacactat tgagtacttc gtcaacacca cctttaacta    120
cccgacgatg gcggaagcct atcgggtagc tgcgttaaac ggtttaaacc gcctgtttgc    180
ggccaacgat gaaaactatt ctgaaaacta tgcggatgcg tcttaatagt tgacaattaa    240
tcatcggcat agtatatcgg catagtataa tacgactcac tataggaggg ccatcatgaa    300
gaccttcaac atctctcagc aggatctgga gctggtggag tcgccactg agaagatcac    360 catgctctat gaggacaaca agcaccatgt cggggcggcc atcaggacca agactgggga    420
gatcatctct gctgtccaca ttgaggccta cattggcagg gtcactgtct gtgctgaagc    480
cattgccatt gggtctgctg tgagcaacgg gcagaaggac tttgacacca ttgtggctgt    540
caggcacccc tactctgatg aggtggacag atccatcagg gtggtcagcc cctgtggcat    600
```

```
gtgcagagag ctcatctctg actatgctcc tgactgcttt gtgctcattg agatgaatgg      660
caagctggtc aaaaccacca ttgaggaact catcccctc aagtacacca ggaactaaag       720
taaaacttta tcgaaatggc catccattct tgcgcggatg ccctctgcca gctgctcata     780 gcggctcgc agcggtgagc caggacgata aaccaggcca atagtgcggc gtggttccgg      840
cttaatgcac gg                                                         852
```

```
<210> SEQ ID NO 11
<211> LENGTH: 898
<212> TYPE: DNA
<213> ORGANISM: Artificial Sequence
<220> FEATURE:
<223> OTHER INFORMATION: zwf-DAS+4:bsdR

<400> SEQUENCE: 11
gaagtggaag aagcctggaa atgggtagac tccattactg aggcgtgggc gatggacaat      60
gatgcgccga aaccgtatca ggccggaacc tggggacccg ttgcctcggt ggcgatgatt     120
acccgtgatg gtcgttcctg aatgagtttt gaggcggcca acgatgaaaa ctattctgaa     180
aactatgcgg atgcgtctta atagttgaca attaatcatc ggcatagtat atcggcatag     240
tataatacga ctcactatag gagggccatc atgaagacct caacatctc tcagcaggat      300 ctggagctgg tggaggtcgc cactgagaag atcaccatgc tctatgagga caacaagcac     360
catgtcgggg cggccatcag gaccaagact ggggagatca tctctgctgt ccacattgag     420
gcctacattg cagggtcac tgtctgtgct gaagccattg ccattgggtc tgctgtgagc      480
aacgggcaga aggactttga caccattgtg gctgtcaggc accctactc tgatgaggtg      540 gacagatcca tcagggtggt cagccccctgt ggcatgtgca gagagctcat ctctgactat    600
gctcctgact gctttgtgct cattgagatg aatggcaagc tggtcaaaac caccattgag     660
gaactcatcc ccctcaagta caccaggaac taaagtaata tctgcgctta tcctttatgg     720 ttatttttacc ggtaacatga tcttgcgcag attgtagaac aattttttaca ctttcaggcc   780 tcgtgcggat tcacccacga ggcttttttt attacactga ctgaaacgtt tttgccctat     840
gagctccggt tacaggcgtt tcagtcataa atcctctgaa tgaaacgcgt tgtgaatc       898
```

```
<210> SEQ ID NO 12
<211> LENGTH: 3037
<212> TYPE: DNA
<213> ORGANISM: Artificial Sequence
<220> FEATURE:
<223> OTHER INFORMATION: Plasmid pSMART-waaHp-GFPuv

<400> SEQUENCE: 12
tgcccaggca tcaaataaaa cgaaaggctc agtcgaaaga ctgggccttt cgttttatct      60
gttgtttgtc ggtgaacgct ctctactaga gtcacactgg ctcaccttcg ggtgggcctt     120
tctgcgttta tacacagcta acaccacgtc gtccctatct gctgcctag gtctatgagt     180 ggttgctgga taacgtgcgt aattgtgctg atctcttata tagctgctct cattatctct     240
ctaccctgaa gtgactctct cacctgtaaa aataatatct cacaggctta atagtttctt     300
aatacaaagc ctgtaaaacg tcaggataac ttctatattc agggagacca caacggtttc     360
cctctacaaa taattttgtt taactttcgt gtgtaggagg ataatctatg gctagcaaag     420
gagaagaact tttcactgga gttgtcccaa ttcttgttga attagatggt gatgttaatg     480
ggcacaaatt ttctgtcagt ggagagggtg aaggtgatgc tacatacgga aagcttaccc     540
```

```
ttaaatttat ttgcactact ggaaaactac ctgttccatg gccaacactt gtcactactt        600
tctcttatgg tgttcaatgc ttttcccgtt atccggatca tatgaaacgg catgactttt        660
tcaagagtgc catgcccgaa ggttatgtac aggaacgcac tatatctttc aaagatgacg        720
ggaactacaa gacgcgtgct gaagtcaagt ttgaaggtga tacccttgtt aatcgtatcg        780
agttaaaagg tattgatttt aagaagatg gaaacattct cggacacaaa ctcgagtaca         840
actataactc acacaatgta tacatcacgg cagacaaaca aaagaatgga atcaaagcta        900
acttcaaaat tcgccacaac attgaagatg gatccgttca actagcagac cattatcaac        960
aaaatactcc aattggcgat ggccctgtcc ttttaccaga caaccattac ctgtcgacac       1020
aatctgccct ttcgaaagat cccaacgaaa agcgtgacca catggtcctt cttgagtttg       1080
taactgctgc tgggattaca catggcatgg atgagctcta caaataatga ggatccccgg       1140
cttatcggtc agtttcacct gatttacgta aaaacccgct tcggcgggtt tttgcttttg       1200
gaggggcaga aagatgaatg actgtccacg acgctatacc caaagaaag acgaattctc        1260 tagatatcgc tcaatactga ccatttaaat catacctgac ctccatagca gaaagtcaaa       1320
agcctccgac cggaggcttt tgacttgatc ggcacgtaag aggttccaac tttcaccata       1380
atgaaataag atcactaccg ggcgtatttt ttgagttatc gagattttca ggagctaagg       1440
aagctaaaat gagccatatt caacgggaaa cgtcttgctc gaggccgcga ttaaattcca       1500
acatggatgc tgatttatat gggtataaat gggctcgcga taatgtcggg caatcaggtg       1560
cgacaatcta tcgattgtat gggaagcccg atgcgccaga gttgtttctg aaacatggca       1620
aaggtagcgt tgccaatgat gttacagatg agatggtcag gctaaactgg ctgacggaat       1680
ttatgcctct tccgaccatc aagcatttta tccgtactcc tgatgatgca tggttactca       1740
ccactgcgat cccagggaaa acagcattcc aggtattaga agaatatcct gattcaggtg       1800
aaaatattgt tgatgcgctg gcagtgttcc tgcgccggtt gcattcgatt cctgtttgta       1860
attgtccttt taacggcgat cgcgtatttc gtctcgctca ggcgcaatca cgaatgaata       1920
acggtttggt tggtgcgagt gattttgatg acgagcgtaa tggctggcct gttgaacaag       1980
tctggaaaga aatgcataag cttttgccat tctcaccgga ttcagtcgtc actcatggtg       2040
atttctcact tgataacctt attttttgacg aggggaaatt aataggttgt attgatgttg       2100
gacgagtcgg aatcgcagac cgataccagg atcttgccat cctatggaac tgcctcggtg       2160
agttttctcc ttcattacag aaacggcttt ttcaaaaata tggtattgat aatcctgata       2220
tgaataaatt gcagtttcac ttgatgctcg atgagttttt ctaatgaggg cccaaatgta       2280
atcacctggc tcaccttcgg gtgggccttt ctgcgttgct ggcgtttttc cataggctcc       2340 gccccctga cgagcatcac aaaaatcgat gctcaagtca gaggtggcga acccgacag         2400 gactataaag ataccaggcg tttccccctg gaagctccct cgtgcgctct cctgttccga       2460
ccctgccgct taccggatac ctgtccgcct ttctcccttc gggaagcgtg gcgctttctc       2520
atagctcacg ctgtaggtat ctcagttcgg tgtaggtcgt tcgctccaag ctgggctgtg       2580
tgcacgaacc ccccgttcag cccgaccgct gcgccttatc cggtaactat cgtcttgagt       2640
ccaacccggt aagacacgac ttatcgccac tggcagcagc cactggtaac aggattagca       2700
gagcgaggta tgtaggcggt gctacagagt tcttgaagtg gtggcctaac tacggctaca       2760
ctagaagaac agtatttggt atctgcgctc tgctgaagcc agttaccctg gaaaagagt        2820 tggtagctct tgatccggca aacaaaccac cgctggtagc ggtggttttt tgtttgcaa        2880 gcagcagatt acgcgcagaa aaaaaggatc tcaagaagat cctttgattt tctaccgaag       2940
```

```
aaaggcccac ccgtgaaggt gagccagtga gttgattgca gtccagttac gctggagtct   3000
gaggctcgtc ctgaatgata tcaagcttga attcgtt                             3037

<210> SEQ ID NO 13
<211> LENGTH: 2780
<212> TYPE: DNA
<213> ORGANISM: Artificial Sequence
<220> FEATURE:
<223> OTHER INFORMATION: pCASCADE-Control Plasmid

<400> SEQUENCE: 13
gacgtcttaa gacccacttt cacatttaag ttgttttttct aatccgcata tgatcaattc     60
aaggccgaat aagaaggctg gctctgcacc ttggtgatca ataattcga tagcttgtcg      120 taataatggc ggcatactat cagtagtagg tgtttcccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accaacacgg tttccctcta caaataattt    960
tgtttaactt tgaattcaaa agatctggta ccacctcgag ttccccgcgc cagcggggat   1020
aaaccgaaaa aaaacccccg cccctgacag ggcggggttt ttttcctag ggatatattc    1080 cgcttcctcg ctcactgact cgctacgctc ggtcgttcga ctgcggcgag cggaaatggc   1140
ttacgaacgg ggcggagatt tcctggaaga tgccaggaag atacttaaca gggaagtgag   1200
agggccgcgg caaagccgtt tttccatagg ctccgccccc ctgacaagca tcacgaaatc   1260
tgacgctcaa atcagtggtg gcgaaacccg acaggactat aaagatacca ggcgtttccc   1320
cctggcggct ccctcgtgcg ctctcctgtt cctgcctttc ggtttaccgg tgtcattccg   1380
ctgttatggc cgcgtttgtc tcattccacg cctgacactc agttccgggt aggcagttcg   1440
ctccaagctg gactgtatgc acgaaccccc cgttcagtcc gaccgctgcg ccttatccgg   1500
taactatcgt cttgagtcca acccggaaag acatgcaaaa gcaccactgg cagcagccac   1560
tggtaattga tttagaggag ttagtcttga agtcatgcgc cggttaaggc taaactgaaa   1620
ggacaagttt tggtgactgc gctcctccaa gccagttacc tcggttcaaa gagttggtag   1680
ctcagagaac cttcgaaaaa ccgccctgca aggcggtttt ttcgttttca gagcaagaga   1740
ttacgcgcag accaaaacga tctcaagaag atcatcttat taatcagata aaatatttct   1800
agatttcagt gcaatttatc tcttcaaatg tagcacctga agtcagcccc atacgatata   1860
agttgttact agtgcttgga ttctcaccaa taaaaaacgc ccggcggcaa ccgagcgttc   1920
```

```
tgaacaaatc cagatggagt tctgaggtca ttactggatc tatcaacagg agtccaagcg    1980
agctcgatat caaattacgc cccgccctgc cactcatcgc agtactgttg taattcatta    2040
agcattctgc cgacatggaa gccatcacaa acggcatgat gaacctgaat cgccagcggc    2100
atcagcacct tgtcgccttg cgtataatat ttgcccatgg tgaaaacggg ggcgaagaag    2160
ttgtccatat tggccacgtt taaatcaaaa ctggtgaaac tcacccaggg attggctgag    2220
acgaaaaaca tattctcaat aaacccttta gggaaatagg ccaggttttc accgtaacac    2280
gccacatctt gcgaatatat gtgtagaaac tgccggaaat cgtcgtggta ttcactccag    2340
agcgatgaaa acgtttcagt ttgctcatgg aaaacggtgt aacaagggtg aacactatcc    2400
catatcacca gctcaccgtc tttcattgcc atacgaaatt ccggatgagc attcatcagg    2460
cgggcaagaa tgtgaataaa ggccggataa aacttgtgct tattttttct tacggtcttt    2520
aaaaaggccg taatatccag ctgaacggtc tggttatagg tacattgagc aactgactga    2580
aatgcctcaa aatgttcttt acgatgccat gggatatat caacggtggt atatccagtg    2640
atttttttct ccatttagc ttccttagct cctgaaaatc tcgataactc aaaaaatacg    2700
cccggtagtg atcttatttc attatggtga agttggaac tcttacgtg ccgatcaacg    2760 tctcattttc gccagatatc                                                2780

<210> SEQ ID NO 14
<211> LENGTH: 2843
<212> TYPE: DNA
<213> ORGANISM: Artificial Sequence
<220> FEATURE:
<223> OTHER INFORMATION: pCASCADE-gltA2 Plasmid

<400> SEQUENCE: 14
gacgtcttaa gacccacttt cacatttaag ttgttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta tttttacat gccaatacaa tgtaggctgc tctacaccta gcttctgggc     540
gagtttacgg gttgttaaac cttcgattcc gacctcatta agcagctcta atgcgctgtt    600 aatcactttta ctttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caataatttt    960
tgtttaactt tgaattcaaa agatctggta ccacctcgag ttccccgcgc cagcggggat   1020
aaaccgtatt gaccaattca ttcgggacag ttattagttc gagttccccg cgccagcggg   1080
gataaaccga aaaaaaaacc ccgccctga caggggcgggg ttttttttcc tagggatata   1140
ttccgcttcc tcgctcactg actcgctacg ctcggtcgtt cgactgcggc gagcggaaat   1200
```

```
ggcttacgaa cggggcggag atttcctgga agatgccagg aagatactta acagggaagt    1260
gagagggccg cggcaaagcc gttttttccat aggctccgcc ccctgacaa gcatcacgaa    1320 atctgacgct caaatcagtg gtggcgaaac ccgacaggac tataaagata ccaggcgttt    1380
ccccctggcg gctccctcgt gcgctctcct gttcctgcct ttcggtttac cggtgtcatt    1440
ccgctgttat ggccgcgttt gtctcattcc acgcctgaca ctcagttccg ggtaggcagt    1500
tcgctccaag ctggactgta tgcacgaacc ccccgttcag tccgaccgct gcgccttatc    1560
cggtaactat cgtcttgagt ccaacccgga agacatgca aaagcaccac tggcagcagc    1620
cactggtaat tgatttagag gagttagtct tgaagtcatg cgccggttaa ggctaaactg    1680
aaaggacaag ttttggtgac tgcgctcctc caagccagtt acctcggttc aaagagttgg    1740
tagctcagag aaccttcgaa aaaccgcccc gcaaggcggt ttttttcgttt tcagagcaag    1800 agattacgcg cagaccaaaa cgatctcaag aagatcatct tattaatcag ataaaatatt    1860
tctagatttc agtgcaattt atctcttcaa atgtagcacc tgaagtcagc cccatacgat    1920
ataagttgtt actagtgctt ggattctcac caataaaaaa cgcccggcgg caaccgagcg    1980
ttctgaacaa atccagatgg agttctgagg tcattactgg atctatcaac aggagtccaa    2040
gcgagctcga tatcaaatta cgccccgccc tgccactcat cgcagtactg ttgtaattca    2100
ttaagcattc tgccgacatg gaagccatca caaacggcat gatgaacctg aatcgccagc    2160
ggcatcagca ccttgtcgcc ttgcgtataa tatttgccca tggtgaaaac gggggcgaag    2220
aagttgtcca tattggccac gtttaaatca aaactggtga aactcaccca gggattggct    2280
gagacgaaaa acatattctc aataaaccct ttagggaaat aggccaggtt ttcaccgtaa    2340
cacgccacat cttgcgaata tatgtgtaga actgccgga atcgtcgtg gtattcactc    2400 cagagcgatg aaaacgtttc agtttgctca tggaaaacgg tgtaacaagg gtgaacacta    2460
tcccatatca ccagctcacc gtctttcatt gccatacgaa attccggatg agcattcatc    2520
aggcgggcaa gaatgtgaat aaaggccgga taaaacttgt gcttattttt ctttacggtc    2580
tttaaaaagg ccgtaatatc cagctgaacg gtctggttat aggtacattg agcaactgac    2640
tgaaatgcct caaaatgttc tttacgatgc cattgggata tatcaacggt ggtatatcca    2700
gtgatttttt tctccatttt agcttcctta gctcctgaaa atctcgataa ctcaaaaaat    2760
acgcccggta gtgatcttat ttcattatgg tgaaagttgg aacctcttac gtgccgatca    2820
acgtctcatt ttcgccagat atc                                            2843
```

<210> SEQ ID NO 15
<211> LENGTH: 2841
<212> TYPE: DNA
<213> ORGANISM: Artificial Sequence
<220> FEATURE:
<223> OTHER INFORMATION: pCASCADE-fabI Plasmid

<400> SEQUENCE: 15

```
gacgtcttaa gacccacttt cacatttaag ttgttttttct aatccgcata tgatcaattc     60
aaggccgaat aagaaggctg gctctgcacc ttggtgatca aataattcga tagcttgtcg    120
taataatggc ggcatactat cagtagtagg tgtttcccct tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
```

-continued

```
taaagcacat ctaaaacttt tagcgttatt acgtaaaaaa tcttgccagc tttcccttc      420 taaagggcaa aagtgagtat ggtgcctatc taacatctca atggctaagg cgtcgagcaa     480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgcctag gtctatgagt ggttgctgga taactctttc tgacaccttag   840 ctatcttaca aatgtaacaa aaaagttatt tttctgtaat tcgagcatgt catgttaccc    900
cgcgagcata aaacgcgtat attcagggag accacaacgg tttccctcta caataattt     960 tgtttaactt tgaattcaaa agatctggta ccacctcgag ttccccgcgc cagcggggat   1020
aaaccgttga ttataataac cgtttatctg ttcgtatcga gttccccgcg ccagcgggga    1080
taaaccgaaa aaaaaacccc gcccctgaca gggcggggtt ttttttccta gggatatatt    1140
ccgcttcctc gctcactgac tcgctacgct cggtcgttcg actgcggcga gcggaaatgg    1200
cttacgaacg gggcggagat ttcctggaag atgccaggaa gatacttaac agggaagtga    1260
gagggccgcg gcaaagccgt ttttccatag gctccgcccc cctgacaagc atcacgaaat   1320
ctgacgctca aatcagtggt ggcgaaaccc gacaggacta taaagatacc aggcgtttcc    1380
ccctggcggc tccctcgtgc gctctcctgt tcctgccttt cggtttaccg gtgtcattcc    1440
gctgttatgg ccgcgtttgt ctcattccac gcctgacact cagttccggg taggcagttc    1500
gctccaagct ggactgtatg cacgaacccc ccgttcagtc cgaccgctgc gccttatccg    1560
gtaactatcg tcttgagtcc aacccggaaa gacatgcaaa agcaccactg gcagcagcca   1620
ctggtaattg atttagagga gttagtcttg aagtcatgcg ccggttaagg ctaaactgaa    1680
aggacaagtt ttggtgactg cgctcctcca agccagttac ctcggttcaa agagttggta    1740
gctcagagaa ccttcgaaaa accgccctgc aaggcggttt tttcgttttc agagcaagag    1800
attacgcgca gaccaaaacg atctcaagaa gatcatctta ttaatcagat aaaatatttc    1860
tagatttcag tgcaatttat ctcttcaaat gtagcacctg aagtcagccc catacgatat    1920
aagttgttac tagtgcttgg attctcacca ataaaaaacg cccggcggca accgagcgtt    1980
ctgaacaaat ccagatggag ttctgaggtc attactggat ctatcaacag gagtccaagc    2040
gagctcgata tcaaattacg ccccgccctg ccactcatcg cagtactgtt gtaattcatt    2100
aagcattctg ccgacatgga agccatcaca aacggcatga tgaacctgaa tcgccagcgg    2160
catcagcacc ttgtcgcctt gcgtataata tttgcccatg gtgaaaacgg ggcgaagaa     2220 gttgtccata ttggccacgt ttaaatcaaa actggtgaaa ctcacccagg gattggctga    2280
gacgaaaaac atattctcaa taaacccttt agggaaatag gccaggtttt caccgtaaca    2340
cgccacatct tgcgaatata tgtgtagaaa ctgccgaaaa tcgtcgtggt attcactcca    2400
gagcgatgaa aacgtttcag tttgctcatg gaaaacggtg taacaagggt gaacactatc    2460
ccatatcacc agctcaccgt cttcattgc catacgaaat tccggatgag cattcatcag    2520
gcgggcaaga atgtgaataa aggccggata aaacttgtgc ttattttct ttacggtctt     2580 taaaaaggcc gtaatatcca gctgaacggt ctggttatag gtacattgag caactgactg    2640
aaatgcctca aaatgttctt tacgatgcca ttgggatata tcaacggtgg tatatccagt    2700
gatttttttc tccattttag cttccttagc tcctgaaaat ctcgataact caaaaaatac    2760
```

```
gcccggtagt gatcttattt cattatggtg aaagttggaa cctcttacgt gccgatcaac    2820
gtctcatttt cgccagatat c                                             2841

<210> SEQ ID NO 16
<211> LENGTH: 2841
<212> TYPE: DNA
<213> ORGANISM: Artificial Sequence
<220> FEATURE:
<223> OTHER INFORMATION: pCASCADE-udhA Plasmid

<400> SEQUENCE: 16
gacgtcttaa gacccacttt cacatttaag ttgttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtacttt gctccatcgc gatgacttag     360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgttac cattctgttg cttttatgta taagaatcga gttcccgcg ccagcgggga    1080 taaaccgaaa aaaaacccc gcccctgaca gggcggggtt ttttttccta gggatatatt    1140
ccgcttcctc gctcactgac tcgctacgct cggtcgttcg actgcggcga gcggaaatgg    1200
cttacgaacg gggcggagat ttcctggaag atgccaggaa gatacttaac agggaagtga    1260
gagggccgcg gcaaagccgt ttttccatag gctccgcccc cctgacaagc atcacgaaat    1320
ctgacgctca aatcagtggt ggcgaaaccc gacaggacta taaagatacc aggcgtttcc    1380
ccctggcggc tccctcgtgc gctctcctgt tcctgccttt cggtttaccg gtgtcattcc    1440
gctgttatgg ccgcgtttgt ctcattccac gcctgacact cagttccggg taggcagttc    1500
gctccaagct ggactgtatg cacgaacccc ccgttcagtc cgaccgctgc gccttatccg    1560
gtaactatcg tcttgagtcc aacccggaaa gacatgcaaa agcaccactg gcagcagcca    1620
ctggtaattg atttagagga gttagtcttg aagtcatgcg ccggttaagg ctaaactgaa    1680
aggacaagtt ttggtgactg cgctcctcca agccagttac ctcggttcaa agagttggta    1740
gctcagagaa ccttcgaaaa accgccctgc aaggcggttt tttcgttttc agagcaagag    1800
attacgcgca gaccaaaacg atctcaagaa gatcatctta ttaatcagat aaaatatttc    1860
tagatttcag tgcaatttat ctcttcaaat gtagcacctg aagtcagccc catacgatat    1920
```

```
aagttgttac tagtgcttgg attctcacca ataaaaaacg cccggcggca accgagcgtt    1980
ctgaacaaat ccagatggag ttctgaggtc attactggat ctatcaacag gagtccaagc    2040
gagctcgata tcaaattacg ccccgccctg ccactcatcg cagtactgtt gtaattcatt    2100
aagcattctg ccgacatgga agccatcaca aacggcatga tgaacctgaa tcgccagcgg    2160
catcagcacc ttgtcgcctt gcgtataata tttgcccatg gtgaaaacgg gggcgaagaa    2220
gttgtccata ttggccacgt ttaaatcaaa actggtgaaa ctcacccagg gattggctga    2280
gacgaaaaac atattctcaa taaacccttt agggaaatag gccaggtttt caccgtaaca    2340
cgccacatct tgcgaatata tgtgtagaaa ctgccgaaaa tcgtcgtggt attcactcca    2400
gagcgatgaa aacgtttcag tttgctcatg gaaaacggtg taacaagggt gaacactatc    2460
ccatatcacc agctcaccgt ctttcattgc catacgaaat tccggatgag cattcatcag    2520
gcgggcaaga atgtgaataa aggccggata aaacttgtgc ttattttttct ttacggtctt    2580 taaaaaggcc gtaatatcca gctgaacggt ctggttatag gtacattgag caactgactg    2640 aaaatgcctca aaatgttctt tacgatgcca ttgggatata tcaacggtgg tatatccagt    2700 gattttttttc tccattttag cttccttagc tcctgaaaat ctcgataact caaaaaatac    2760
gcccggtagt gatcttattt cattatggtg aaagttggaa cctcttacgt gccgatcaac    2820
gtctcatttt cgccagatat c                                              2841

<210> SEQ ID NO 17
<211> LENGTH: 2841
<212> TYPE: DNA
<213> ORGANISM: Artificial Sequence
<220> FEATURE:
<223> OTHER INFORMATION: pCASCADE-zwf Plasmid

<400> SEQUENCE: 17
gacgtcttaa gacccacttt cacatttaag ttgttttttct aatccgcata tgatcaattc      60
aaggccgaat aagaaggctg gctctgcacc ttggtgatca ataattcga tagcttgtcg       120 taataatggc ggcatactat cagtagtagg tgtttccctt tcttctttag cgacttgatg      180
ctcttgatct tccaatacgc aacctaaagt aaaatgcccc acagcgctga gtgcatataa      240
tgcattctct agtgaaaaac cttgttggca taaaaaggct aattgatttt cgagagtttc      300
atactgtttt tctgtaggcc gtgtacctaa atgtacttttt gctccatcgc gatgacttag    360
taaagcacat ctaaaacttt tagcgttatt acgtaaaaaa tcttgccagc tttccccttc     420
taaagggcaa aagtgagtat ggtgcctatc taacatctca atggctaagg cgtcgagcaa     480
agcccgctta ttttttacat gccaatacaa tgtaggctgc tctacaccta gcttctgggc    540
gagtttacgg gttgttaaac cttcgattcc gacctcatta agcagctcta atgcgctgtt     600
aatcacttta cttttatcta atctagacat catccaggca tcaaataaaa cgaaaggctc     660
agtcgaaaga ctgggccttt cgttttatct gttgtttgtc ggtgaacgct ctctactaga     720
gtcacactgg ctcaccttcg ggtgggcctt tctgcgttta tacacagcta acaccacgtc     780
gtccctatct gctgccctag gtctatgagt ggttgctgga taactctttc tgacaccta      840 ctatcttaca aatgtaacaa aaagttatt tttctgtaat tcgagcatgt catgttaccc       900
cgcgagcata aaacgcgtat attcagggag accacaacgg tttccctcta caaataattt     960
tgtttaactt tgaattcaaa agatctggta ccacctcgag ttccccgcgc cagcggggat    1020
aaaccgctcg taaagcagt acagtgcacc gtaagatcga gttccccgcg ccagcgggga    1080
taaaccgaaa aaaaaacccc gcccctgaca gggcggggtt ttttttccta gggatatatt    1140
```

```
ccgcttcctc gctcactgac tcgctacgct cggtcgttcg actgcggcga gcggaaatgg    1200
cttacgaacg gggcggagat ttcctggaag atgccaggaa gatacttaac agggaagtga    1260
gagggccgcg gcaaagccgt ttttccatag gctccgcccc cctgacaagc atcacgaaat    1320
ctgacgctca aatcagtggt ggcgaaaccc gacaggacta taaagatacc aggcgttttc    1380
ccctggcggc tccctcgtgc gctctcctgt tcctgccttt cggtttaccg gtgtcattcc    1440
gctgttatgg ccgcgtttgt ctcattccac gcctgacact cagttccggg taggcagttc    1500
gctccaagct ggactgtatg cacgaacccc cgttcagtc cgaccgctgc gccttatccg    1560
gtaactatcg tcttgagtcc aacccggaaa gacatgcaaa agcaccactg gcagcagcca    1620
ctggtaattg atttagagga gttagtcttg aagtcatgcg ccggttaagg ctaaactgaa    1680
aggacaagtt ttggtgactg cgctcctcca agccagttac ctcggttcaa agagttggta    1740
gctcagagaa ccttcgaaaa accgccctgc aaggcggttt tttcgttttc agagcaagag    1800
attacgcgca gaccaaaacg atctcaagaa gatcatctta ttaatcagat aaaatatttc    1860
tagatttcag tgcaatttat ctcttcaaat gtagcacctg aagtcagccc catacgatat    1920
aagttgttac tagtgcttgg attctcacca ataaaaaacg cccggcggca accgagcgtt    1980
ctgaacaaat ccagatggag ttctgaggtc attactggat ctatcaacag gagtccaagc    2040
gagctcgata tcaaattacg ccccgccctg ccactcatcg cagtactgtt gtaattcatt    2100
aagcattctg ccgacatgga agccatcaca aacggcatga tgaacctgaa tcgccagcgg    2160
catcagcacc ttgtcgcctt gcgtataata tttgcccatg gtgaaaacgg gggcgaagaa    2220
gttgtccata ttggccacgt ttaaatcaaa actggtgaaa ctcacccagg gattggctga    2280
gacgaaaaac atattctcaa taaacccttt agggaaatag gccaggtttt caccgtaaca    2340
cgccacatct tgcgaatata tgtgtagaaa ctgccggaaa tcgtcgtggt attcactcca    2400
gagcgatgaa aacgtttcag tttgctcatg gaaaacggtg taacaagggt gaacactatc    2460
ccatatcacc agctcaccgt ctttcattgc catacgaaat tccggatgag cattcatcag    2520 gcggcaaga atgtgaataa aggccggata aaacttgtgc ttattttctt ttacggtctt    2580
taaaaaggcc gtaatatcca gctgaacggt ctggttatag gtacattgag caactgactg    2640
aaatgcctca aatgttctt tacgatgcca ttgggatata tcaacggtgg tatatccagt    2700 gattttttc tccattttag cttccttagc tcctgaaaat ctcgataact caaaaaatac    2760
gcccggtagt gatcttattt cattatggtg aaagttggaa cctcttacgt gccgatcaac    2820
gtctcatttt cgccagatat c                                              2841
```

<210> SEQ ID NO 18
<211> LENGTH: 2842
<212> TYPE: DNA
<213> ORGANISM: Artificial Sequence
<220> FEATURE:
<223> OTHER INFORMATION: pCASCADE-gltA1 Plasmid

<400> SEQUENCE: 18

```
gacgtcttaa gacccacttt cacatttaag ttgttttct aatccgcata tgatcaattc      60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
```

```
atactgtttt tctgtaggcc gtgtacctaa atgtactttt gctccatcgc gatgacttag    360
taaagcacat ctaaaacttt tagcgttatt acgtaaaaaa tcttgccagc tttcccttc    420 taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacaccttg    840
ctatcttaca aatgtaacaa aaagttatt tttctgtaat tcgagcatgt catgttccc    900 cgcgagcata aaacgcgtat attcagggag accacaacgg tttccctcta caaataattt    960
tgtttaactt tgaattcaaa agatctggta ccacctcgag ttccccgcgc cagcggggat    1020
aaaccgaaaa gcatataatg cgtaaaagtt atgaagttcg agttcccgc gccagcgggg    1080 ataaaccgaa aaaaaaccc cgcccctgac agggcggggt ttttttcct agggatatat    1140 tccgcttcct cgctcactga ctcgctacgc tcggtcgttc gactgcggcg agcggaaatg    1200
gcttacgaac ggggcggaga tttcctggaa gatgccagga agatacttaa cagggaagtg    1260
agagggccgc ggcaaagccg ttttttccata ggctccgccc ccctgacaag catcacgaaa    1320
tctgacgctc aaatcagtgg tggcgaaacc cgacaggact ataaagatac caggcgtttc    1380
cccctggcgg ctccctcgtg cgctctcctg ttcctgcctt tcggtttacc ggtgtcattc    1440
cgctgttatg gccgcgtttg tctcattcca cgcctgacac tcagttccgg gtaggcagtt    1500
cgctccaagc tggactgtat gcacgaaccc ccgttcagt ccgaccgctg cgccttatcc    1560
ggtaactatc gtcttgagtc caacccggaa agacatgcaa aagcaccact ggcagcagcc    1620
actggtaatt gatttagagg agttagtctt gaagtcatgc gccggttaag gctaaactga    1680
aaggacaagt tttggtgact gcgctcctcc aagccagtta cctcggttca agagttggt    1740 agctcagaga accttcgaaa aaccgccctg caaggcggtt ttttcgtttt cagagcaaga    1800
gattacgcgc agaccaaaac gatctcaaga agatcatctt attaatcaga taaaatattt    1860
ctagatttca gtgcaattta tctcttcaaa tgtagcacct gaagtcagcc ccatacgata    1920
taagttgtta ctagtgcttg gattctcacc aataaaaaac gcccggcggc aaccgagcgt    1980
tctgaacaaa tccagatgga gttctgaggt cattactgga tctatcaaca ggagtccaag    2040
cgagctcgat atcaaattac gccccgccct gccactcatc gcagtactgt tgtaattcat    2100
taagcattct gccgacatgg aagccatcac aaacggcatg atgaacctga atcgccagcg    2160
gcatcagcac cttgtcgcct tgcgtataat atttgcccat ggtgaaaacg ggggcgaaga    2220
agttgtccat attggccacg tttaaatcaa aactggtgaa actcacccag ggattggctg    2280
agacgaaaaa catattctca ataaacccctt tagggaaata ggccaggttt tcaccgtaac    2340
acgccacatc ttgcgaatat atgtgtagaa actgccggaa atcgtcgtgg tattcactcc    2400
agagcgatga aaacgtttca gtttgctcat ggaaaacggt gtaacaaggg tgaacactat    2460
cccatatcac cagctcaccg tctttcattg ccatacgaaa ttccggatga gcattcatca    2520
ggcgggcaag aatgtgaata aaggccggat aaaacttgtg cttatttttc tttacggtct    2580
ttaaaaaggc cgtaatatcc agctgaacgg tctggttata ggtacattga gcaactgact    2640
gaaatgcctc aaaatgttct ttacgatgcc attgggatat atcaacggtg gtatatccag    2700
```

```
tgattttttt ctccatttta gcttccttag ctcctgaaaa tctcgataac tcaaaaaata    2760
cgcccggtag tgatcttatt tcattatggt gaaagttgga acctcttacg tgccgatcaa    2820
cgtctcattt tcgccagata tc                                             2842
```

<210> SEQ ID NO 19
<211> LENGTH: 2903
<212> TYPE: DNA
<213> ORGANISM: Artificial Sequence
<220> FEATURE:
<223> OTHER INFORMATION: pCASCADE-gltA2-udhA Plasmid

<400> SEQUENCE: 19

```
gacgtcttaa gacccacttt cacatttaag ttgttttttct aatccgcata tgatcaattc    60
aaggccgaat aagaaggctg gctctgcacc ttggtgatca ataattcga tagcttgtcg     120 taataatggc ggcatactat cagtagtagg tgtttcccctt tcttctttag cgacttgatg   180
ctcttgatct tccaatacgc aacctaaagt aaaatgcccc acagcgctga gtgcatataa   240
tgcattctct agtgaaaaac cttgttggca taaaaggct aattgatttt cgagagtttc     300
atactgtttt tctgtaggcc gtgtacctaa atgtactttt gctccatcgc gatgacttag   360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa   480
agcccgctta ttttttacat gccaataaat gtaggctgct ctacacctag cttctgggcg   540
agtttacggg ttgttaaacc ttcgattccg acctcattaa gcagctctaa tgcgctgtta   600
atcactttac ttttatctaa tctagacatc atccaggcat caaataaaac gaaaggctca   660
gtcgaaagac tgggcctttc gttttatctg ttgtttgtcg gtgaacgctc tctactagag   720
tcacactggc tcaccttcgg gtgggccttt ctgcgtttat acacagctaa caccacgtcg   780
tccctatctg ctgccctagg tctatgagtg gttgctggat aactcttctct gacaccttac   840 tatcttacaa atgtaacaaa aaagttatt ttctgtaatt cgagcatgtc atgttaccc     900 gcgagcataa aacgcgtata ttcagggaga ccacaacggt ttccctctac aaataattt     960 gtttaacttt gaattcaaaaa gatctggtac cacctcgagt tccccgcgcc agcggggata   1020
aaccgtattg accaattcat cgggacagt tattagttcg agttcccgc gccagcgggg      1080 ataaaccgtt accattctgt tgcttttatg tataagaatc gagttcccg cgccagcggg     1140 gataaaccga aaaaaaaacc cgcccctga cagggcgggg tttttttttcc tagggatata    1200 ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gttttttccat aggctccgcc cccctgacaa gcatcacgaa   1380
atctgacgct caaatcagtg gtggcgaaac ccgacaggac tataaagata ccaggcgttt   1440
ccccctggcg ctccctcgt gcgctctcct gttcctgcct ttcggtttac cggtgtcatt    1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga agacatgca aaagcaccac tggcagcagc    1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgccct gcaaggcggt ttttcgtttt tcagagcaag   1860
```

| | | |
|---|---|---|
| agattacgcg cagaccaaaa cgatctcaag aagatcatct tattaatcag ataaaatatt | 1920 | |
| tctagatttc agtgcaattt atctcttcaa atgtagcacc tgaagtcagc cccatacgat | 1980 | |
| ataagttgtt actagtgctt ggattctcac caataaaaaa cgcccggcgg caaccgagcg | 2040 | |
| ttctgaacaa atccgatgg agttctgagg tcattactgg atctatcaac aggagtccaa | 2100 | |
| gcgagctcga tatcaaatta cgccccgccc tgccactcat cgcagtactg ttgtaattca | 2160 | |
| ttaagcattc tgccgacatg gaagccatca caaacggcat gatgaacctg aatcgccagc | 2220 | |
| ggcatcagca ccttgtcgcc ttgcgtataa tatttgccca tggtgaaaac ggggggcgaag | 2280 | |
| aagttgtcca tattgccac gtttaaatca aaactggtga aactcaccca gggattggct | 2340 | |
| gagacgaaaa acatattctc aataaaccct ttagggaaat aggccaggtt ttcaccgtaa | 2400 | |
| cacgccacat cttgcgaata tatgtgtaga actgccgga aatcgtcgtg gtattcactc | 2460 | |
| cagagcgatg aaaacgtttc agtttgctca tggaaaacgg tgtaacaagg gtgaacacta | 2520 | |
| tcccatatca ccagctcacc gtctttcatt gccatacgaa attccggatg agcattcatc | 2580 | |
| aggcgggcaa gaatgtgaat aaaggccgga taaaacttgt gcttattttt ctttacggtc | 2640 | |
| tttaaaaagg ccgtaatatc cagctgaacg gtctggttat aggtacattg agcaactgac | 2700 | |
| tgaaatgcct caaaatgttc tttacgatgc cattgggata tatcaacggt ggtatatcca | 2760 | |
| gtgatttttt tctccatttt agcttcctta gctcctgaaa atctcgataa ctcaaaaaat | 2820 | |
| acgcccggta gtgatcttat ttcattatgg tgaaagttgg aacctcttac gtgccgatca | 2880 | |
| acgtctcatt ttcgccagat atc | 2903 | |

<210> SEQ ID NO 20  
<211> LENGTH: 2902  
<212> TYPE: DNA  
<213> ORGANISM: Artificial Sequence  
<220> FEATURE:  
<223> OTHER INFORMATION: pCASCADE-fabI-udhA Plasmid

<400> SEQUENCE: 20

| | | |
|---|---|---|
| gacgtcttaa gacccacttt cacatttaag ttgttttttct aatccgcata tgatcaattc | 60 | |
| aaggccgaat aagaaggctg gctctgcacc ttggtgatca ataattcga tagcttgtcg | 120 | |
| taataatggc ggcatactat cagtagtagg tgtttccctt tcttctttag cgacttgatg | 180 | |
| ctcttgatct tccaatacgc aacctaaagt aaaatgcccc acagcgctga gtgcatataa | 240 | |
| tgcattctct agtgaaaaac cttgttggca taaaaaggct aattgatttt cgagagtttc | 300 | |
| atactgtttt tctgtaggcc gtgtacctaa atgtactttt gctccatcgc gatgacttag | 360 | |
| taaagcacat ctaaaacttt tagcgttatt acgtaaaaaa tcttgccagc tttcccttc | 420 | |
| taaagggcaa aagtgagtat ggtgcctatc taacatctca atggctaagg cgtcgagcaa | 480 | |
| agcccgctta ttttttacat gccaatacaa tgtaggctgc tctacaccta gcttctgggc | 540 | |
| gagtttacgg gttgttaaac cttcgattcc gacctcatta agcagctcta atgcgctgtt | 600 | |
| aatcacttta cttttatcta atctagacat catccaggca tcaaataaaa cgaaaggctc | 660 | |
| agtcgaaaga ctgggccttt cgttttatct gttgtttgtc ggtgaacgct ctctactaga | 720 | |
| gtcacactgg ctcaccttcg ggtgggcctt tctgcgttta tacacagcta acaccacgtc | 780 | |
| gtccctatct gctgccctag gtctatgagt ggttgctgga taactctttc tgacacctta | 840 | |
| ctatcttaca aatgtaacaa aaagttatt tttctgtaat tcgagcatgt catgttaccc | 900 | |
| cgcgagcata aaacgcgtat attcagggag accacaacgg tttccctcta caataaattt | 960 | |
| tgtttaactt tgaattcaaa agatctggta ccacctcgag ttccccgcgc cagcggggat | 1020 | |

```
aaaccgttga ttataataac cgtttatctg ttcgtatcga gttccccgcg ccagcgggga      1080
taaaccgtta ccattctgtt gcttttatgt ataagaatcg agttccccgc ccagcgggg      1140 ataaaccgaa aaaaaaaccc cgcccctgac agggcggggt ttttttttcct agggatatat    1200 tccgcttcct cgctcactga ctcgctacgc tcggtcgttc gactgcgcg agcggaaatg      1260 gcttacgaac ggggcggaga tttcctggaa gatgccagga agatacttaa cagggaagtg    1320
agagggccgc ggcaaagccg ttttccata ggctccgccc ccctgacaag catcacgaaa      1380
tctgacgctc aaatcagtgg tggcgaaacc cgacaggact ataaagatac caggcgtttc    1440
cccctggcgg ctccctcgtg cgctctcctg ttcctgcctt tcggtttacc ggtgtcattc    1500
cgctgttatg gccgcgtttg tctcattcca cgcctgacac tcagttccgg gtaggcagtt    1560
cgctccaagc tggactgtat gcacgaaccc ccgttcagt ccgaccgctg cgccttatcc      1620
ggtaactatc gtcttgagtc caacccggaa agacatgcaa agcaccact ggcagcagcc      1680 actggtaatt gatttagagg agttagtctt gaagtcatgc gccggttaag gctaaactga    1740
aaggacaagt tttggtgact gcgctcctcc aagccagtta cctcggttca aagagttggt    1800
agctcagaga accttcgaaa aaccgccctg caaggcggtt ttttcgtttt cagagcaaga    1860
gattacgcgc agaccaaaac gatctcaaga agatcatctc attaatcaga taaaatattt    1920
ctagatttca gtgcaattta tctcttcaaa tgtagcacct gaagtcagcc ccatacgata    1980
taagttgtta ctagtgcttg gattctcacc aataaaaaac gcccggcggc aaccgagcgt    2040
tctgaacaaa tccagatgga gttctgaggt cattactgga tctatcaaca ggagtccaag    2100
cgagctcgat atcaaattac gccccgccct gccactcatc gcagtactgt tgtaattcat    2160
taagcattct gccgacatgg aagccatcac aaacggcatg atgaacctga atcgccagcg    2220
gcatcagcac cttgtcgcct tgcgtataat atttgcccat ggtgaaaacg ggggcgaaga    2280
agttgtccat attggccacg tttaaatcaa aactggtgaa actcacccag ggattggctg    2340
agacgaaaaa catattctca ataaaccctt tagggaaata ggccaggttt tcaccgtaac    2400
acgccacatc ttgcgaatat atgtgtagaa actgccggaa atcgtcgtgg tattcactcc    2460
agagcgatga aaacgtttca gtttgctcat ggaaaacggt gtaacaaggg tgaacactat    2520
cccatatcac cagctcaccg tctttcattg ccatacgaaa ttccggatga gcattcatca    2580
ggcgggcaag aatgtgaata aaggccggat aaaacttgtg cttatttttc tttacggtct    2640
ttaaaaaggc cgtaatatcc agctgaacgg tctggttata ggtacattga gcaactgact    2700
gaaatgcctc aaaatgttct ttacgatgcc attgggatat atcaacggtg gtatatccag    2760 tgatttttt ctccatttta gcttccttag ctcctgaaaa tctcgataac tcaaaaaata    2820
cgcccggtag tgatcttatt tcattatggt gaaagttgga acctcttacg tgccgatcaa    2880
cgtctcattt tcgccagata tc                                              2902

<210> SEQ ID NO 21
<211> LENGTH: 2903
<212> TYPE: DNA
<213> ORGANISM: Artificial Sequence
<220> FEATURE:
<223> OTHER INFORMATION: pCASCADE-fabI-gltA1 Plasmid

<400> SEQUENCE: 21
gacgtcttaa gacccacttt cacatttaag ttgttttttct aatccgcata tgatcaattc      60
aaggccgaat aagaaggctg gctctgcacc ttggtgatca aataattcga tagcttgtcg     120
```

```
taataatggc ggcatactat cagtagtagg tgtttcccct tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttcccctc     420 taaagggcaa aagtgagtat ggtgcctatc taacatctca atggctaagg cgtcgagcaa    480
agcccgctta tttttacat gccaatacaa tgtaggctgc tctacaccta gcttctgggc     540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgcctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat    1020
aaaccgttga ttataataac cgtttatctg ttcgtatcga gttccccgcg ccagcgggga    1080
taaaccgaaa agcatataat gcgtaaaagt tatgaagttc gagttcccg cgccagcggg     1140 gataaaccga aaaaaaaacc ccgccctga cagggcgggg ttttttttcc tagggatata    1200
ttccgcttcc tcgctcactg actcgctacg ctcggtcgtt cgactgcggc gagcggaaat    1260
ggcttacgaa cggggcggag atttcctgga agatgccagg aagatactta acagggaagt    1320
gagagggccg cggcaaagcc gttttttccat aggctccgcc ccctgacaa gcatcacgaa    1380 atctgacgct caaatcagtg gtggcgaaac ccgacaggac tataaagata ccaggcgttt    1440
ccccctggcg ctccctcgt gcgctctcct gttcctgcct ttcggtttac cggtgtcatt     1500
ccgctgttat ggccgcgttt gtctcattcc acgcctgaca ctcagttccg ggtaggcagt    1560
tcgctccaag ctggactgta tgcacgaacc ccccgttcag tccgaccgct gcgccttatc    1620
cggtaactat cgtcttgagt ccaacccgga agacatgca aaagcaccac tggcagcagc     1680
cactggtaat tgatttagag gagttagtct tgaagtcatg cgccggttaa ggctaaactg    1740
aaaggacaag ttttggtgac tgcgctcctc caagccagtt acctcggttc aaagagttgg    1800
tagctcagaa aaccttcgaa aaaccgcccct gcaaggcggt tttttcgttt tcagagcaag    1860
agattacgcg cagaccaaaa cgatctcaag aagatcatct tattaatcag ataaaatatt    1920
tctagatttc agtgcaattt atctcttcaa atgtagcacc tgaagtcagc cccatacgat    1980
ataagttgtt actagtgctt ggattctcac caataaaaaa cgcccggcgg caaccgagcg    2040
ttctgaacaa atccagatgg agttctgagg tcattactgg atctatcaac aggagtccaa    2100
gcgagctcga tatcaaatta cgccccgccc tgccactcat cgcagtactg ttgtaattca    2160
ttaagcattc tgccgacatg gaagccatca caaacggcat gatgaacctg aatcgccagc    2220
ggcatcagca ccttgtcgcc ttgcgtataa tatttgccca tggtgaaaac ggggcgaag    2280 aagttgtcca tattggccac gtttaaatca aaactggtga actcaccca gggattggct    2340 gagacgaaaa acatattctc aataaaccct ttagggaaat aggccaggtt ttcaccgtaa    2400
cacgccacat cttgcgaata tatgtgtaga aactgccgga atcgtcgtg gtattcactc     2460 cagagcgatg aaaacgtttc agtttgctca tggaaaacgg tgtaacaagg gtgaacacta    2520
```

```
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
tgaaatgcct caaaatgttc tttacgatgc cattgggata tatcaacggt ggtatatcca   2760 gtgattttt tctccatttt agcttcctta gctcctgaaa atctcgataa ctcaaaaaat   2820
acgcccggta gtgatcttat tcattatgg tgaaagttgg aacctcttac gtgccgatca   2880
acgtctcatt ttcgccagat atc                                          2903
```

<210> SEQ ID NO 22
<211> LENGTH: 2904
<212> TYPE: DNA
<213> ORGANISM: Artificial Sequence
<220> FEATURE:
<223> OTHER INFORMATION: pCASCADE-fabI-gltA2 Plasmid

<400> SEQUENCE: 22

```
gacgtcttaa gacccacttt cacatttaag ttgttttttct aatccgcata tgatcaattc     60
aaggccgaat aagaaggctg gctctgcacc ttggtgatca ataattcga tagcttgtcg      120 taataatggc ggcatactat cagtagtagg tgtttcccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagttc     300 atactgtttt tctgtaggcc gtgtacctaa atgtacttt gctccatcgc gatgacttag    360
taaagcacat ctaaaacttt tagcgttatt acgtaaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600 aatcactta cttttatcta atctagacat catccaggca tcaaataaaa cgaaaggctc     660
agtcgaaaga ctgggccttt cgttttatct gttgtttgtc ggtgaacgct ctctactaga   720
gtcacactgg ctcaccttcg ggtgggcctt tctgcgttta tacacagcta acaccacgtc    780
gtccctatct gctgccctag gtctatgagt ggttgctgga taactctttc tgacaccttta  840 ctatcttaca aatgtaacaa aaaagttatt tttctgtaat tcgagcatgt catgttaccc    900
cgcgagcata aaacgcgtat attcagggag accacaacgg tttccctcta caaataattt   960
tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgtat tgaccaattc attcgggaca gttattagtt cgagttcccc gcgccagcgg  1140
ggataaaccg aaaaaaaaac cccgccctg acagggcggg gtttttttc ctagggatat    1200 attccgcttc ctcgctcact gactcgctac gctcggtcgt tcgactgcgg cgagcggaaa  1260
tggcttacga acggggcgga gatttcctgg aagatgccag gaagatactt aacagggaag   1320
tgagagggcc gcggcaaagc cgttttttcca taggctccgc ccccctgaca agcatcacga   1380
aatctgacgc tcaaatcagt ggtggcgaaa cccgacagga ctataaagat accaggcgtt   1440
tccccctggc ggctccctcg tgcgctctcc tgttcctgcc tttcggttta ccggtgtcat  1500
tccgctgtta tggccgcgtt tgtctcattc cacgcctgac actcagttcc gggtaggcag  1560
ttcgctccaa gctggactgt atgcacgaac ccccgttca gtccgaccgc tgcgccttat    1620
```

```
ccggtaacta tcgtcttgag tccaacccgg aaagacatgc aaaagcacca ctggcagcag    1680
ccactggtaa ttgatttaga ggagttagtc ttgaagtcat gcgccggtta aggctaaact    1740
gaaaggacaa gttttggtga ctgcgctcct ccaagccagt tacctcggtt caaagagttg    1800
gtagctcaga gaaccttcga aaaccgccc tgcaaggcgg tttttcgtt ttcagagcaa     1860 gagattacgc gcagaccaaa acgatctcaa gaagatcatc ttattaatca gataaaatat    1920
ttctagattt cagtgcaatt tatctcttca aatgtagcac ctgaagtcag ccccatacga    1980
tataagttgt tactagtgct tggattctca ccaataaaaa acgcccggcg caaccgagc     2040 gttctgaaca atccagatg gagttctgag gtcattactg gatctatcaa caggagtcca     2100
agcgagctcg atatcaaatt acgccccgcc ctgccactca tcgcagtact gttgtaattc    2160
attaagcatt ctgccgacat ggaagccatc acaaacggca tgatgaacct gaatcgccag    2220
cggcatcagc accttgtcgc cttgcgtata atatttgccc atggtgaaaa cggggcgaa     2280 gaagttgtcc atattggcca cgtttaaatc aaaactggtg aaactcaccc agggattggc    2340
tgagacgaaa aacatattct caataaaccc tttagggaaa taggccaggt tttcaccgta    2400
acacgccaca tcttgcgaat atatgtgtag aaactgccgg aaatcgtcgt ggtattcact    2460
ccagagcgat gaaaacgttt cagtttgctc atggaaaacg gtgtaacaag ggtgaacact    2520
atcccatatc accagctcac cgtctttcat tgccatacga aattccggat gagcattcat    2580
caggcgggca agaatgtgaa taaaggccgg ataaaacttg tgcttatttt tctttacggt    2640 cttttaaaaag gccgtaatat ccagctgaac ggtctggtta taggtacatt gagcaactga    2700
ctgaaatgcc tcaaaatgtt ctttacgatg ccattgggat atatcaacgg tggtatatcc    2760
agtgattttt ttctccattt tagcttcctt agctcctgaa atctcgata actcaaaaaa     2820 tacgcccggt agtgatctta tttcattatg gtgaaagttg gaacctctta cgtgccgatc    2880
aacgtctcat tttcgccaga tatc                                           2904
```

<210> SEQ ID NO 23
<211> LENGTH: 2902
<212> TYPE: DNA
<213> ORGANISM: Artificial Sequence
<220> FEATURE:
<223> OTHER INFORMATION: pCASCADE-fabI-zwf Plasmid

<400> SEQUENCE: 23

```
gacgtcttaa gacccacttt cacatttaag ttgttttct aatccgcata tgatcaattc      60
aaggccgaat aagaaggctg gctctgcacc ttggtgatca aataattcga tagcttgtcg    120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtacttt gctccatcgc gatgacttag    360
taaagcacat ctaaaacttt tagcgttatt acgtaaaaaa tcttgccagc tttcccttc    420 taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
```

```
gtccctatct gctgccctag gtctatgagt ggttgctgga taactctttc tgacacctta      840
ctatcttaca aatgtaacaa aaaagttatt tttctgtaat tcgagcatgt catgttaccc      900
cgcgagcata aaacgcgtat attcagggag accacaacgg tttccctcta caaataattt      960
tgtttaactt tgaattcaaa agatctggta ccacctcgag ttccccgcgc cagcggggat     1020
aaaccgttga ttataataac cgtttatctg ttcgtatcga gttccccgcg ccagcgggga     1080
taaaccgctc gtaaaagcag tacagtgcac cgtaagatcg agttccccgc ccagcggggg     1140
ataaaccgaa aaaaaaaccc cgccctgac  agggcgggt  tttttttcct agggatatat     1200
tccgcttcct cgctcactga ctcgctacgc tcggtcgttc gactgcggcg agcggaaatg     1260
gcttacgaac ggggcggaga tttcctggaa gatgccagga agatacttaa cagggaagtg     1320
agagggccgc ggcaaagccg ttttttccata ggctccgccc ccctgacaag catcacgaaa     1380
tctgacgctc aaatcagtgg tggcgaaacc cgacaggact ataaagatac caggcgtttc     1440
cccctggcgg ctccctcgtg cgctctcctg ttcctgcctt tcggtttacc ggtgtcattc     1500
cgctgttatg gccgcgtttg tctcattcca cgcctgacac tcagttccgg gtaggcagtt     1560
cgctccaagc tggactgtat gcacgaaccc ccgttcagt  ccgaccgctg cgccttatcc     1620
ggtaactatc gtcttgagtc aacccggaa  agacatgcaa aagcaccact ggcagcagcc     1680
actggtaatt gatttagagg agttagtctt gaagtcatgc gccggttaag gctaaactga     1740
aaggacaagt tttggtgact gcgctcctcc aagccagtta cctcggttca agagttggt      1800 agctcagaga accttcgaaa aaccgccctg caaggcggtt ttttcgtttt cagagcaaga     1860
gattacgcgc agaccaaaac gatctcaaga agatcatctt attaatcaga taaaatattt     1920
ctagatttca gtgcaattta tctcttcaaa tgtagcacct gaagtcagcc ccatacgata     1980
taagttgtta ctagtgcttg gattctcacc aataaaaaac gcccggcggc aaccgagcgt     2040
tctgaacaaa tccagatgga gttctgaggt cattactgga tctatcaaca ggagtccaag     2100
cgagctcgat atcaaattac gccccgccct gccactcatc gcagtactgt tgtaattcat     2160
taagcattct gccgacatgg aagccatcac aaacggcatg atgaacctga atcgccagcg     2220
gcatcagcac cttgtcgcct tgcgtataat atttgcccat ggtgaaaacg ggggcgaaga     2280
agttgtccat attggccacg tttaaatcaa aactggtgaa actcacccag ggattggctg     2340
agacgaaaaa catattctca ataaaccctt tagggaaata ggccaggttt tcaccgtaac     2400
acgccacatc ttgcgaatat atgtgtagaa actgccggaa atcgtcgtgg tattcactcc     2460
agagcgatga aaacgtttca gtttgctcat ggaaaacggt gtaacaaggg tgaacactat     2520
cccatatcac cagctcaccg tctttcattg ccatacgaaa ttccggatga gcattcatca     2580
ggcgggcaag aatgtgaata aaggccggat aaaacttgtg cttatttttc tttacggtct     2640
ttaaaaaggc cgtaatatcc agctgaacgg tctggttata ggtacattga gcaactgact     2700
gaaatgcctc aaaatgttct ttacgatgcc attgggatat atcaacggtg gtatatccag     2760 tgatttttt  ctccatttta gcttccttag ctcctgaaaa tctcgataac tcaaaaaata     2820
cgcccggtag tgatcttatt tcattatggt gaaagttgga acctcttacg tgccgatcaa     2880
cgtctcattt tcgccagata tc                                               2902
```

<210> SEQ ID NO 24
<211> LENGTH: 2903
<212> TYPE: DNA
<213> ORGANISM: Artificial Sequence
<220> FEATURE:

<223> OTHER INFORMATION: pCASCADE-gltA1-udhA Plasmid

<400> SEQUENCE: 24

```
gacgtcttaa gacccacttt cacatttaag ttgttttct aatccgcata tgatcaattc      60
aaggccgaat aagaaggctg gctctgcacc ttggtgatca aataattcga tagcttgtcg     120
taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaggct aattgatttt cgagagtttc      300
atactgtttt tctgtaggcc gtgtacctaa atgtacttt gctccatcgc gatgacttag      360
taaagcacat ctaaaacttt tagcgttatt acgtaaaaaa tcttgccagc tttccccttc     420
taaagggcaa aagtgagtat ggtgcctatc taacatctca atggctaagg cgtcgagcaa     480
agcccgctta ttttttacat gccaatacaa tgtaggctgc tctacaccta gcttctgggc     540
gagtttacgg gttgttaaac cttcgattcc gacctcatta agcagctcta atgcgctgtt     600
aatcacttta cttttatcta atctagacat catccaggca tcaaataaaa cgaaaggctc     660
agtcgaaaga ctgggccttt cgttttatct gttgtttgtc ggtgaacgct ctctactaga     720
gtcacactgg ctcaccttcg gtgggccctt tctgcgttta tacacagcta acaccacgtc     780
gtccctatct gctgccctag gtctatgagt ggttgctgga taactctttc tgacaccta     840
ctatcttaca aatgtaacaa aaagttatt tttctgtaat tcgagcatgt catgttaccc     900
cgcgagcata aaacgcgtat attcagggag accacaacgg tttccctcta caaataattt     960
tgtttaactt tgaattcaaa agatctggta ccacctcgag ttccccgcgc cagcggggat    1020
aaaccgaaaa gcatataatg cgtaaaagtt atgaagttcg agttccccgc gccagcgggg    1080
ataaaccgtt accattctgt tgcttttatg tataagaatc gagttccccg cgccagcggg    1140
gataaaccga aaaaaaaacc ccgcccctga cagggcgggg ttttttttcc tagggatata    1200
ttccgcttcc tcgctcactg actcgctacg ctcggtcgtt cgactgcggc gagcggaaat    1260
ggcttacgaa cggggcggag atttcctgga agatgccagg aagatactta acagggaagt    1320
gagagggccg cggcaaagcc gttttttccat aggctccgcc cccctgacaa gcatcacgaa    1380
atctgacgct caaatcagtg gtggcgaaac ccgacaggac tataaagata ccaggcgttt    1440
ccccctggcg gctccctcgt gcgctctcct gttcctgcct ttcggtttac cggtgtcatt    1500
ccgctgttat ggccgcgttt gtctcattcc acgcctgaca ctcagttccg ggtaggcagt    1560
tcgctccaag ctggactgta tgcacgaacc ccccgttcag tccgaccgct gcgccttatc    1620
cggtaactat cgtcttgagt ccaacccgga aagacatgca aaagcaccac tggcagcagc    1680
cactggtaat tgatttagag gagttagtct tgaagtcatg cgccggttaa ggctaaactg    1740
aaaggacaag ttttggtgac tgcgctcctc caagccagtt acctcggttc aaagagttgg    1800
tagctcagag aaccttcgaa aaaccgcccct gcaaggcggt ttttttcgttt tcagagcaag    1860
agattacgcg cagaccaaaa cgatctcaag aagatcatct tattaatcag ataaaatatt    1920
tctagatttc agtgcaattt atctcttcaa atgtagcacc tgaagtcagc cccatacgat    1980
ataagttgtt actagtgctt ggattctcac caataaaaaa cgcccggcgg caaccgagcg    2040
ttctgaacaa atccagatgg agttctgagg tcattactgg atctatcaac aggagtccaa    2100
gcgagctcga tatcaaatta cgccccgccc tgccactcat cgcagtactg ttgtaattca    2160
ttaagcattc tgccgacatg gaagccatca caaacgcgat gatgaacctg aatcgccagc    2220
ggcatcagca ccttgtcgcc ttgcgtataa tatttgccca tggtgaaaac ggggggcgaag    2280
```

| | |
|---|---:|
| aagttgtcca tattggccac gtttaaatca aaactggtga aactcaccca gggattggct | 2340 |
| gagacgaaaa acatattctc aataaaccct ttagggaaat aggccaggtt ttcaccgtaa | 2400 |
| cacgccacat cttgcgaata tatgtgtaga aactgccgga aatcgtcgtg gtattcactc | 2460 |
| cagagcgatg aaaacgtttc agtttgctca tggaaaacgg tgtaacaagg gtgaacacta | 2520 |
| tcccatatca ccagctcacc gtctttcatt gccatacgaa attccggatg agcattcatc | 2580 |
| aggcgggcaa gaatgtgaat aaaggccgga taaaacttgt gcttattttt ctttacggtc | 2640 |
| tttaaaaagg ccgtaatatc cagctgaacg gtctggttat aggtacattg agcaactgac | 2700 |
| tgaaatgcct caaaatgttc tttacgatgc cattgggata tatcaacggt ggtatatcca | 2760 |
| gtgattttt tctccatttt agcttcctta gctcctgaaa atctcgataa ctcaaaaaat | 2820 |
| acgcccggta gtgatcttat ttcattatgg tgaaagttgg aacctcttac gtgccgatca | 2880 |
| acgtctcatt ttcgccagat atc | 2903 |

<210> SEQ ID NO 25
<211> LENGTH: 2904
<212> TYPE: DNA
<213> ORGANISM: Artificial Sequence
<220> FEATURE:
<223> OTHER INFORMATION: pCASCADE-gltA2-udhA Plasmid

<400> SEQUENCE: 25

| | |
|---|---:|
| gacgtcttaa gacccacttt cacatttaag ttgttttct aatccgcata tgatcaattc | 60 |
| aaggccgaat aagaaggctg gctctgcacc ttggtgatca aataattcga tagcttgtcg | 120 |
| taataatggc ggcatactat cagtagtagg tgtttcccct tcttctttag cgacttgatg | 180 |
| ctcttgatct tccaatacgc aacctaaagt aaaatgcccc acagcgctga gtgcatataa | 240 |
| tgcattctct agtgaaaaac cttgttggca taaaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttcccttc | 420 |
| taaagggcaa aagtgagtat ggtgcctatc taacatctca atggctaagg cgtcgagcaa | 480 |
| agcccgctta tttttacat gccaatacaa tgtaggctgc tctacaccta gcttctgggc | 540 |
| gagtttacgg gttgttaaac cttcgattcc gacctcatta agcagctcta atgcgctgtt | 600 |
| aatcacttta ctttatcta atctagacat catccaggca tcaaataaaa cgaaaggctc | 660 |
| agtcgaaaga ctgggccttt cgttttatct gttgtttgtc ggtgaacgct ctctactaga | 720 |
| gtcacactgg ctcaccttcg ggtgggcctt tctgcgttta tacacagcta acaccacgtc | 780 |
| gtccctatct gctgccctag gtctatgagt ggttgctgga taactctttc tgacaccta | 840 |
| ctatcttaca aatgtaacaa aaaagttatt tttctgtaat tcgagcatgt catgttaccc | 900 |
| cgcgagcata aaacgcgtat attcagggag accacaacgg tttccctcta caaataattt | 960 |
| tgtttaactt tgaattcaaa agatctggta ccacctcgag ttccccgcgc cagcgggat | 1020 |
| aaaccgtatt gaccaattca ttcgggacag ttattagttc gagttccccg cgccagcggg | 1080 |
| gataaaccgt taccattctg ttgcttttat gtataagaat cgagttcccc gcgccagcgg | 1140 |
| ggataaaccg aaaaaaaaac cccgccctg acagggcggg gttttttttc ctaggatat | 1200 |
| attccgcttc ctcgctcact gactcgctac gctcggtcgt tcgactgcgg cgagcggaaa | 1260 |
| tggcttacga acgggcgga gatttcctgg aagatgccag gaagatactt aacagggaag | 1320 |
| tgagagggcc gcggcaaagc cgttttttcca taggctccgc cccctgaca agcatcacga | 1380 |

| | |
|---|---|
| aatctgacgc tcaaatcagt ggtggcgaaa cccgacagga ctataaagat accaggcgtt | 1440 |
| tccccctggc ggctccctcg tgcgctctcc tgttcctgcc tttcggttta ccggtgtcat | 1500 |
| tccgctgtta tggccgcgtt tgtctcattc cacgcctgac actcagttcc gggtaggcag | 1560 |
| ttcgctccaa gctggactgt atgcacgaac ccccgttca gtccgaccgc tgcgccttat | 1620 |
| ccggtaacta tcgtcttgag tccaacccgg aaagacatgc aaaagcacca ctggcagcag | 1680 |
| ccactggtaa ttgatttaga ggagttagtc ttgaagtcat gcgccggtta aggctaaact | 1740 |
| gaaaggacaa gttttggtga ctgcgctcct ccaagccagt tacctcggtt caaagagttg | 1800 |
| gtagctcaga gaaccttcga aaaccgccc tgcaaggcgg ttttttcgtt ttcagagcaa | 1860 |
| gagattacgc gcagaccaaa acgatctcaa gaagatcatc ttattaatca gataaaatat | 1920 |
| ttctagattt cagtgcaatt tatctcttca aatgtagcac ctgaagtcag ccccatacga | 1980 |
| tataagttgt tactagtgct tggattctca ccaataaaaa acgcccggcg caaccgagc | 2040 |
| gttctgaaca atccagatg gagttctgag gtcattactg gatctatcaa caggagtcca | 2100 |
| agcgagctcg atatcaaatt acgccccgcc ctgccactca tcgcagtact gttgtaattc | 2160 |
| attaagcatt ctgccgacat ggaagccatc acaaacggca tgatgaacct gaatcgccag | 2220 |
| cggcatcagc accttgtcgc cttgcgtata atatttgccc atggtgaaaa cggggggcgaa | 2280 |
| gaagttgtcc atattggcca cgtttaaatc aaaactggtg aaactcaccc agggattggc | 2340 |
| tgagacgaaa aacatattct caataaaccc tttaggaaa taggccaggt ttcaccgta | 2400 |
| acacgccaca tcttgcgaat atatgtgtag aaactgccgg aaatcgtcgt ggtattcact | 2460 |
| ccagagcgat gaaaacgttt cagtttgctc atggaaaacg gtgtaacaag ggtgaacact | 2520 |
| atcccatatc accagctcac cgtctttcat tgccatacga aattccggat gagcattcat | 2580 |
| caggcgggca agaatgtgaa taaaggccgg ataaaacttg tgcttatttt tctttacggt | 2640 |
| ctttaaaaag gccgtaatat ccagctgaac ggtctggtta taggtacatt gagcaactga | 2700 |
| ctgaaatgcc tcaaaatgtt ctttacgatg ccattgggat atatcaacgg tggtatatcc | 2760 |
| agtgattttt ttctccattt tagcttcctt agctcctgaa aatctcgata actcaaaaaa | 2820 |
| tacgcccggt agtgatctta tttcattatg gtgaaagttg gaacctctta cgtgccgatc | 2880 |
| aacgtctcat tttcgccaga tatc | 2904 |

<210> SEQ ID NO 26
<211> LENGTH: 2903
<212> TYPE: DNA
<213> ORGANISM: Artificial Sequence
<220> FEATURE:
<223> OTHER INFORMATION: pCASCADE-gltA1-zwf Plasmid

<400> SEQUENCE: 26

| | |
|---|---|
| gacgtcttaa gacccacttt cacatttaag ttgttttttct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttcccctt tcttctttag cgacttgatg | 180 |
| ctccttgatct tccaatacgc aacctaaagt aaaatgcccc acagcgctga gtgcatataa | 240 |
| tgcattctct agtgaaaaac cttgttggca taaaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttcccttc | 420 |
| taaagggcaa aagtgagtat ggtgcctatc taacatctca atggctaagg cgtcgagcaa | 480 |
| agcccgctta ttttttacat gccaatacaa tgtaggctgc tctacaccta gcttctgggc | 540 |

```
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta cacagctaa acaccacgtc    780 gtccctatct gctgcctag gtctatgagt ggttgctgga taactctttc tgacacctta    840
ctatcttaca aatgtaacaa aaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgaaaa gcatataatg cgtaaaagtt atgaagttcg agttccccgc gccagcgggg   1080
ataaaccgct cgtaaaagca gtacagtgca ccgtaagatc gagttccccg cgccagcggg   1140
gataaaccga aaaaaaacc ccgcccctga cagggcgggg ttttttttcc tagggatata   1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gttttttccat aggctccgcc ccctgacaa gcatcacgaa   1380 atctgacgct caaatcagtg gtggcgaaac ccgacaggac tataaagata ccaggcgttt   1440 cccctggcg ctccctcgt gcgctctcct gttcctgcct ttcggtttac cggtgtcatt   1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga agacatgca aaagcaccac tggcagcagc   1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgcccct gcaaggcggt tttttcgttt tcagagcaag   1860
agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac ggggcgaag   2280 aagttgtcca tattggccac gtttaaatca aaactggtga actcaccca gggattggct   2340 gagacgaaaa acatattctc aataaaccct taggggaaat aggccaggtt ttcaccgtaa   2400
cacgccacat cttgcgaata tatgtgtaga aactgccgga atcgtcgtg gtattcactc   2460 cagagcgatg aaaacgtttc agtttgctca tggaaaacgg tgtaacaagg gtgaacacta   2520
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
tgaaatgcct caaaatgttc tttacgatgc cattgggata tatcaacggt ggtatatcca   2760
gtgatttttt tctccatttt agcttcctta gctcctgaaa atctcgataa ctcaaaaaat   2820
acgcccggta gtgatcttat ttcattatgg tgaaagttgg aacctcttac gtgccgatca   2880
```

-continued

| acgtctcatt ttcgccagat atc | 2903 |

<210> SEQ ID NO 27
<211> LENGTH: 2904
<212> TYPE: DNA
<213> ORGANISM: Artificial Sequence
<220> FEATURE:
<223> OTHER INFORMATION: pCASCADE-gltA2-zwf Plasmid

<400> SEQUENCE: 27

| gacgtcttaa gacccacttt cacatttaag ttgttttcct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttccctt tcttctttag cgacttgatg | 180 |
| ctcttgatct tccaatacgc aacctaaagt aaaatgcccc acagcgctga gtgcatataa | 240 |
| tgcattctct agtgaaaaac cttgttggca taaaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttccccttc | 420 |
| taaagggcaa aagtgagtat ggtgcctatc taacatctca atggctaagg cgtcgagcaa | 480 |
| agcccgctta ttttttacat gccaatacaa tgtaggctgc tctacaccta gcttctgggc | 540 |
| gagtttacgg gttgttaaac cttcgattcc gacctcatta agcagctcta atgcgctgtt | 600 |
| aatcactttta cttttatcta atctagacat catccaggca tcaaataaaa cgaaaggctc | 660 |
| agtcgaaaga ctgggccttt cgttttatct gttgtttgtc ggtgaacgct ctctactaga | 720 |
| gtcacactgg ctcaccttcg ggtgggcctt tctgcgttta tacacagcta acaccacgtc | 780 |
| gtccctatct gctgccctag gtctatgagt ggttgctgga taactctttc tgacacctta | 840 |
| ctatcttaca aatgtaacaa aaagttatt tttctgtaat tcgagcatgt catgttaccc | 900 |
| cgcgagcata aaacgcgtat attcagggag accacaacgg tttccctcta caaataattt | 960 |
| tgtttaactt tgaattcaaa agatctggta ccacctcgag ttccccgcgc cagcggggat | 1020 |
| aaaccgtatt gaccaattca ttcgggacag ttattagttc gagttccccg cgccagcggg | 1080 |
| gataaaccgc tcgtaaaagc agtacagtgc accgtaagat cgagttcccc gcgccagcgg | 1140 |
| ggataaaccg aaaaaaaaac cccgcccctg acagggcggg gtttttttc ctagggatat | 1200 |
| attccgcttc ctcgctcact gactcgctac gctcggtcgt tcgactgcgg cgagcggaaa | 1260 |
| tggcttacga acggggcgga gatttcctgg aagatgccag gaagatactt aacagggaag | 1320 |
| tgagagggcc gcggcaaagc cgttttccca taggctccgc cccctgaca agcatcacga | 1380 |
| aatctgacgc tcaaatcagt ggtggcgaaa cccgacagga ctataaagat accaggcgtt | 1440 |
| tccccctggc ggctccctcg tgcgctctcc tgttcctgcc tttcggttta ccggtgtcat | 1500 |
| tccgctgtta tggccgcgtt tgtctcattc cacgcctgac actcagttcc gggtaggcag | 1560 |
| ttcgctccaa gctggactgt atgcacgaac ccccgttca gtccgaccgc tgcgccttat | 1620 |
| ccggtaacta tcgtcttgag tccaacccgg aaagacatgc aaaagcacca ctggcagcag | 1680 |
| ccactggtaa ttgatttaga ggagttagtc ttgaagtcat gcgccggtta aggctaaact | 1740 |
| gaaaggacaa gttttggtga ctgcgctcct ccaagccagt tacctcggtt caaagagttg | 1800 |
| gtagctcaga gaaccttcga aaaaccgccc tgcaaggcgg ttttttcgtt ttcagagcaa | 1860 |
| gagattacgc gcagaccaaa acgatctcaa gaagatcatc ttattaatca gataaaatat | 1920 |
| ttctagattt cagtgcaatt tatctcttca aatgtagcac ctgaagtcag ccccatacga | 1980 |
| tataagttgt tactagtgct tggattctca ccaataaaaa acgcccggcg gcaaccgagc | 2040 |

```
gttctgaaca atcccagatg gagttctgag gtcattactg gatctatcaa caggagtcca    2100
agcgagctcg atatcaaatt acgccccgcc ctgccactca tcgcagtact gttgtaattc    2160
attaagcatt ctgccgacat ggaagccatc acaaacggca tgatgaacct gaatcgccag    2220
cggcatcagc accttgtcgc cttgcgtata atatttgccc atggtgaaaa cggggggcgaa   2280 gaagttgtcc atattggcca cgtttaaatc aaaactggtg aaactcaccc agggattggc    2340
tgagacgaaa aacatattct caataaaccc tttaggggaaa taggccaggt tttcaccgta   2400
acacgccaca tcttgcgaat atatgtgtag aaactgccgg aaatcgtcgt ggtattcact    2460
ccagagcgat gaaaacgttt cagtttgctc atggaaaacg gtgtaacaag ggtgaacact    2520
atcccatatc accagctcac cgtctttcat tgccatacga aattccggat gagcattcat    2580
caggcgggca agaatgtgaa taaaggccgg ataaaacttg tgcttatttt tctttacggt    2640
ctttaaaaag gccgtaatat ccagctgaac ggtctggtta taggtacatt gagcaactga    2700
ctgaaatgcc tcaaaatgtt ctttacgatg ccattgggat atatcaacgg tggtatatcc    2760
agtgattttt ttctccattt tagcttcctt agctcctgaa aatctcgata actcaaaaaa    2820
tacgcccggt agtgatctta tttcattatg gtgaaagttg gaacctctta cgtgccgatc    2880
aacgtctcat tttcgccaga tatc                                          2904

<210> SEQ ID NO 28
<211> LENGTH: 3505
<212> TYPE: DNA
<213> ORGANISM: Artificial Sequence
<220> FEATURE:
<223> OTHER INFORMATION: pBT1-mCherry-DAS+4 Vector

<400> SEQUENCE: 28
cgcaaaaaac cccgcttcgg cggggttttt tcgcacgtct ccatcgcttg cccaagttgt      60
gaagcacagc taacaccacg tcgtccctat ctgctgccct aggtctatga gtggttgctg    120
gataacttta cgggcatgca taaggctcgt ataatatatt cagggagacc acaacggttt    180
ccctctacaa ataattttgt ttaactttga tcgcatggtt gctactagag aaagaggaga    240
aatactagat ggtgagcaag ggcgaggagg ataacatggc catcatcaag gagttcatgc    300
gcttcaaggt gcacatggag ggctccgtga acggccacga gttcgagatc gagggcgagg    360
gcgagggccg cccctacgag ggcacccaga ccgccaagct gaaggtgacc aagggtggcc    420
ccctgccctt cgcctgggac atcctgtccc ctcagttcat gtacggctcc aaggcctacg    480
tgaagcaccc cgccgacatc cccgactact tgaagctgtc cttccccgag ggcttcaagt    540
gggagcgcgt gatgaacttc gaggacggcg gcgtggtgac cgtgacccag gactcctccc    600
tgcaggacgg cgagttcatc tacaaggtga agctgcgcgg caccaacttc ccctccgacg    660
gccccgtaat gcagaagaag accatgggct gggaggcctc ctccgagcgg atgtaccccg    720
aggacggcgc cctgaagggc gagatcaagc agaggctgaa gctgaaggac ggcggccact    780
acgacgctga ggtcaagacc acctacaagg ccaagaagcc cgtgcagctg cccggcgcct    840
acaacgtcaa catcaagttg gacatcacct cccacaacga ggactacacc atcgtggaac    900
agtacgaacg cgccgagggc cgccactcca ccggcggcat ggacgaactg tacaaggcgg    960
ccaacgatga aaactattct gaaaactatg cggatgcgtc ttaataagga cgagcctcag   1020
actccagcgt aactggactg aaaacaaact aaagcgccct tgtggcgctt tagttttgtt   1080
ccgcggccac cggctggctc gcttcgctcg gcccgtggac aaccctgctg acaagctga    1140
```

-continued

```
tggacaggct gcgcctgccc acgagcttga ccacagggat tgcccaccgg ctacccagcc    1200
ttcgaccaca tacccaccgg ctccaactgc gcggcctgcg gccttgcccc atcaattttt    1260
ttaattttct ctggggaaaa gcctccggcc tgcggcctgc gcgcttcgct tgccggttgg    1320
acaccaagtg gaaggcgggt caaggctcgc gcagcgaccg cgcagcggct tggccttgac    1380
gcgcctggaa cgacccaagc ctatgcgagt gggggcagtc gaaggcgaag cccgcccgcc    1440 tgcccccga gcctcacggc ggcgagtgcg ggggttccaa gggggcagcg ccaccttggg    1500
caaggccgaa ggccgcgcag tcgatcaaca agccccggag gggccacttt tgccggagg    1560 gggagccgcg ccgaaggcgt gggggaaccc cgcaggggtg cccttctttg gcaccaaag    1620 aactagatat agggcgaaat gcgaaagact taaaaatcaa caacttaaaa aagggggta    1680 cgcaacagct cattgcggca ccccccgcaa tagctcattg cgtaggttaa agaaaatctg    1740
taattgactg ccacttttac gcaacgcata attgttgtcg cgctgccgaa aagttgcagc    1800
tgattgcgca tggtgccgca accgtgcggc accctaccgc atggagataa gcatggccac    1860
gcagtccaga gaaatcggca ttcaagccaa gaacaagccc ggtcactggg tgcaaacgga    1920
acgcaaagcg catgaggcgt gggccgggct tattgcgagg aaacccacgg cggcaatgct    1980
gctgcatcac ctcgtggcgc agatgggcca ccagaacgcc gtggtggtca gccagaagac    2040
actttccaag ctcatcggac gttctttgcg gacggtccaa tacgcagtca aggacttggt    2100
ggccgagcgc tggatctccg tcgtgaagct caacggcccc ggcaccgtgt cggcctacgt    2160
ggtcaatgac cgcgtggcgt ggggccagcc ccgcgaccag ttgcgcctgt cggtgttcag    2220
tgccgccgtg gtggttgatc acgacgacca ggacgaatcg ctgttggggc atggcgacct    2280
gcgccgcatc ccgaccctgt atccgggcga gcagcaacta ccgaccggcc ccggcgagga    2340
gccgcccagc cagcccggca ttccgggcat ggaaccagac ctgccagcct tgaccgaaac    2400
ggaggaatgg gaacggcgcg ggcagcagcg cctgccgatg cccgatgagc cgtgttttct    2460
ggacgatggc gagccgttgg agccgccgac acgggtcacg ctgccgcgcc ggtagtacgt    2520
aagaggttcc aacttccacc ataatgaaat aagatcacta ccgggcgtat ttttttgagtt    2580 atcgagattt tcaggagcta aggaagctaa aatgagtatt caacatttcc gtgtcgccct    2640
tattcccttt tttgcggcat tttgccttcc tgttttgct cacccagaaa cgctggtgaa    2700
agtaaaagat gctgaagatc agttgggtgc acgagtgggt tacatcgaac tggatctcaa    2760
cagcggtaag atccttgaga gttttacgccc cgaagaacgt tttccaatga tgagcacttt    2820
taaagttctg ctatgtggcg cggtattatc ccgtattgac gccgggcaag agcaactcgg    2880
tcgccgcata cactattctc agaatgactt ggttgagtac tcaccagtca cagaaaagca    2940
tctcacggat ggcatgacag taagagaatt atgcagtgct gccataacca tgagtgataa    3000
cactgcggcc aacttacttc tgcaacgat cggaggaccg aaggagctaa ccgcttttt    3060 gcacaacatg ggggatcatg taactcgcct tgatcgttgg gaaccggagc tgaatgaagc    3120
cataccaaac gacgagcgtg acaccacgat gcctgtagca atggcaacaa cgttgcgcaa    3180
actattaact ggcgaactac ttactctagc ttcccggcaa caattaatag actggatgga    3240
ggcggataaa gttgcaggat cacttctgcg ctcggccctc ccggctggct ggtttattgc    3300
tgataaatct ggagccggtg agcgtgggtc tcgcggtatc attgcagcac tggggccaga    3360
tggtaagccc tcccgcatcg tagttatcta cacgacgggg agtcaggcaa ctatggatga    3420
acgaaataga cagatcgctg agataggtgc ctcactgatt aagcattggt aatgaggatc    3480
cccctcaagt caaaagcctc cggtc                                          3505
```

<210> SEQ ID NO 29
<211> LENGTH: 2841
<212> TYPE: DNA
<213> ORGANISM: Artificial Sequence
<220> FEATURE:
<223> OTHER INFORMATION: pCASCADE-proD Plasmid

<400> SEQUENCE: 29

| | | | | | |
|---|---|---|---|---|---|
| gacgtcttaa | gacccacttt | cacatttaag | ttgtttttct | aatccgcata | tgatcaattc | 60 |
| aaggccgaat | aagaaggctg | gctctgcacc | ttggtgatca | aataattcga | tagcttgtcg | 120 |
| taataatggc | ggcatactat | cagtagtagg | tgtttccctt | tcttctttag | cgacttgatg | 180 |
| ctcttgatct | tccaatacgc | aacctaaagt | aaaatgcccc | acagcgctga | gtgcatataa | 240 |
| tgcattctct | agtgaaaaac | cttgttggca | taaaaaggct | aattgatttt | cgagagtttc | 300 |
| atactgtttt | tctgtaggcc | gtgtacctaa | atgtactttt | gctccatcgc | gatgacttag | 360 |
| taaagcacat | ctaaaacttt | tagcgttatt | acgtaaaaaa | tcttgccagc | tttcccctc | 420 |
| taaagggcaa | aagtgagtat | ggtgcctatc | taacatctca | atggctaagg | cgtcgagcaa | 480 |
| agcccgctta | ttttttacat | gccaatacaa | tgtaggctgc | tctacaccta | gcttctgggc | 540 |
| gagtttacgg | gttgttaaac | cttcgattcc | gacctcatta | agcagctcta | atgcgctgtt | 600 |
| aatcacttta | cttttatcta | atctagacat | catccaggca | tcaaataaaa | cgaaaggctc | 660 |
| agtcgaaaga | ctgggccttt | cgttttatct | gttgtttgtc | ggtgaacgct | ctctactaga | 720 |
| gtcacactgg | ctcaccttcg | ggtgggcctt | tctgcgttta | tacacagcta | acaccacgtc | 780 |
| gtccctatct | gctgccctag | gtctatgagt | ggttgctgga | taactctttc | tgacacctta | 840 |
| ctatcttaca | aatgtaacaa | aaaagttatt | tttctgtaat | tcgagcatgt | catgttaccc | 900 |
| cgcgagcata | aaacgcgtat | attcagggag | accacaacgg | tttccctcta | caaataattt | 960 |
| tgtttaactt | tgaattcaaa | agatctggta | ccacctcgag | ttccccgcgc | cagcggggat | 1020 |
| aaaccgagtg | gttgctggat | aactttacgg | gcatgctcga | gttccccgcg | ccagcgggga | 1080 |
| taaaccgaaa | aaaaaacccc | gcccctgaca | gggcggggtt | ttttttccta | gggatatatt | 1140 |
| ccgcttcctc | gctcactgac | tcgctacgct | cggtcgttcg | actgcggcga | gcggaaatgg | 1200 |
| cttacgaacg | gggcggagat | ttcctggaag | atgccaggaa | gatacttaac | agggaagtga | 1260 |
| gagggccgcg | gcaaagccgt | ttttccatag | gctccgcccc | cctgacaagc | atcacgaaat | 1320 |
| ctgacgctca | aatcagtggt | ggcgaaaccc | gacaggacta | taaagatacc | aggcgtttcc | 1380 |
| ccctggcggc | tccctcgtgc | gctctcctgt | tcctgccttt | cggtttaccg | gtgtcattcc | 1440 |
| gctgttatgg | ccgcgtttgt | ctcattccac | gcctgacact | cagttccggg | taggcagttc | 1500 |
| gctccaagct | ggactgtatg | cacgaacccc | ccgttcagtc | cgaccgctgc | gccttatccg | 1560 |
| gtaactatcg | tcttgagtcc | aacccggaaa | gacatgcaaa | agcaccactg | gcagcagcca | 1620 |
| ctggtaattg | atttagagga | gttagtcttg | aagtcatgcg | ccggttaagg | ctaaactgaa | 1680 |
| aggacaagtt | ttggtgactg | cgctcctcca | agccagttac | ctcggttcaa | agagttggta | 1740 |
| gctcagagaa | ccttcgaaaa | accgccctgc | aaggcggttt | tttcgttttc | agagcaagag | 1800 |
| attacgcgca | gaccaaaacg | atctcaagaa | gatcatctta | ttaatcagat | aaaatatttc | 1860 |
| tagatttcag | tgcaatttat | ctcttcaaat | gtagcacctg | aagtcagccc | catacgatat | 1920 |
| aagttgttac | tagtgcttgg | attctcacca | ataaaaaacg | cccggcggca | accgagcgtt | 1980 |
| ctgaacaaat | ccagatggag | ttctgaggtc | attactggat | ctatcaacag | gagtccaagc | 2040 |

| | |
|---|---:|
| gagctcgata tcaaattacg ccccgccctg ccactcatcg cagtactgtt gtaattcatt | 2100 |
| aagcattctg ccgacatgga agccatcaca aacggcatga tgaacctgaa tcgccagcgg | 2160 |
| catcagcacc ttgtcgcctt gcgtataata tttgcccatg gtgaaaacgg gggcgaagaa | 2220 |
| gttgtccata ttggccacgt ttaaatcaaa actggtgaaa ctcacccagg gattggctga | 2280 |
| gacgaaaaac atattctcaa taaacccttt agggaaatag gccaggtttt caccgtaaca | 2340 |
| cgccacatct tgcgaatata tgtgtagaaa ctgccggaaa tcgtcgtggt attcactcca | 2400 |
| gagcgatgaa aacgtttcag tttgctcatg gaaaacggtg taacaagggt gaacactatc | 2460 |
| ccatatcacc agctcaccgt ctttcattgc catacgaaat tccggatgag cattcatcag | 2520 |
| gcgggcaaga atgtgaataa aggccggata aaacttgtgc ttattttttct ttacggtctt | 2580 |
| taaaaaggcc gtaatatcca gctgaacggt ctggttatag gtacattgag caactgactg | 2640 |
| aaatgcctca aaatgttctt tacgatgcca ttgggatata tcaacggtgg tatatccagt | 2700 |
| gatttttttc tccatttag cttccttagc tcctgaaaat ctcgataact caaaaaatac | 2760 |
| gcccggtagt gatcttattt cattatggtg aaagttggaa cctcttacgt gccgatcaac | 2820 |
| gtctcatttt cgccagatat c | 2841 |

<210> SEQ ID NO 30
<211> LENGTH: 4866
<212> TYPE: DNA
<213> ORGANISM: Artificial Sequence
<220> FEATURE:
<223> OTHER INFORMATION: pSMART-3HP1 Plasmid

<400> SEQUENCE: 30

| | |
|---|---:|
| gtgcgtaatt gtgctgatct cttatatagc tgctctcatt atctctctac cctgaagtga | 60 |
| ctctctcacc tgtaaaaata atatctcaca ggcttaatag tttcttaata caaagcctgt | 120 |
| aaaacgtcag gataacttct tttctggaaa aaggagatat accatggcga cgacggggc | 180 |
| acgtagcgct agtgttggtt gggccgagag cctgatcggt ctgcatttgg gaaaagtggc | 240 |
| cttaatcacc ggaggctcag ccggcatcgg cgggcagatc ggccgccttt tagcgctgtc | 300 |
| tggcgcgcgt gttatgctgg ccgctcgcga ccgtcacaaa ctcgaacaaa tgcaggccat | 360 |
| gattcaatcc gaactggcgg aagttggtta taccgatgtc gaagaccgcg tgcacatcgc | 420 |
| gccggggtgt gacgtttcct ctgaagcgca gctggcagat ctggttgaac gcactctgtc | 480 |
| agcattcggt accgtggatt atctgatcaa taacgcgggt attgcgggtg tcgaagagat | 540 |
| ggttatcgac atgccggtgg aaggctggcg tcatacgtta tttgccaacc ttatctcaaa | 600 |
| ttatagcctg atgcgcaaac tggcccctct gatgaagaaa caggggagtg gctatatctt | 660 |
| gaacgtctcg tcgtactttg gtggcgaaaa agatgcggct atcccatacc caaatcgtgc | 720 |
| cgattatgcg gtttcaaaag ccggtcaacg tgcaatggct gaagtgttcg cccgttttcct | 780 |
| cggcccggag atccagatta acgctatcgc cccaggcccg gtggaaggtg accgcctccg | 840 |
| cggcacgggc gaacgtcccg gcttgtttgc gcgccgcgcg cgtttgattt tagaaaataa | 900 |
| gcgtttaaac gagctgcatg ctgcccttat tgcggctgcg cgtacagatg agcgctccat | 960 |
| gcacgaactg gtggaattac tgctgccgaa tgatgtagcg gcactcgagc agaatcccgc | 1020 |
| agccccaacg gcgttgcgcg aactcgcgcg ccgttttcgc agcgaaggcg accggccgc | 1080 |
| gtcaagctcc agtgctctgc tcaaccgcag cattgcggcg aagttactgg cccgcctgca | 1140 |
| caacggcggc tatgttctgc cggcggatat cttcgccaac ctgccgaacc ctccagaccc | 1200 |
| gttcttcacg cgcgcgcaga ttgatcgcga agcccgtaaa gtgcgcgacg ggattatggg | 1260 |

```
aatgctgtat ctgcagcgca tgcctaccga gtttgacgta gcaatggcta ccgtttacta    1320
tctggcggat cgcaatgtga gtggagagac cttccatccg agtgggggc tgcgttacga     1380 gcgcacacct accggcggtg agttatttgg cctgccgtct cccgagcgcc tggcggagtt    1440
agttggaagc accgtatatt tgatcggtga acacttaacc gaacatctga acttgctcgc    1500
acgtgcgtat cttgaacgtt acggtgcgcg tcaggttgtt atgatcgtgg aaacggagac    1560
aggcgcggaa accatgcgcc gcttacttca cgaccatgtc gaagcaggtc gccttatgac    1620
cattgtggcg ggtgaccaaa tcgaagccgc catcgaccag gcgattacgc gctacggccg    1680
tcctggtccg gttgtgtgca ccccttccg ccccttccg accgtcccgt tagttggccg      1740
caaggactcc gattggagca ccgtactgag tgaagccgaa tttgccgaac tgtgtgaaca    1800
tcaactgaca catcatttc gcgtagcgcg caaaatcgca ctttcggatg gtgcctcact     1860
ggctctggtt accccgaaa ccacagcgac aagtaccact gaacagttcg ccctggccaa     1920
ctttattaag acaaccctgc acgcttttac ggccactatc ggagttgaaa gtgagcgcac    1980
ggcgcagcgt atcctgatta atcaggtaga cctcacccgt cgtgctcgtg cggaagaacc    2040
acgcgatccg catgaacgtc agcaggaact ggaacgtttc atcgaggcgg tactgctggt    2100
tacggcccca ttaccgccgg aagcagatac ccgctacgct ggccgcatcc accgtgggcg    2160
tgccattact gtctagtaag ctcttcttct ggaaaaagga gatataccat gatcgtttta    2220
gtaactggag caacggcagg ttttggtgaa tgcattactc gtcgttttat tcaacaaggg    2280
cataaagtta tcgccactgg ccgtcgccag gaacggttgc aggagttaaa agacgaactg    2340
ggagataatc tgtatatcgc ccaactggac gttcgcaacc gcgccgctat tgaagagatg    2400
ctggcatcgc ttcctgccga gtggtgcaat attgatatcc tggtaaataa tgccggcctg    2460
gcgttgggca tggagcctgc gcataaagcc agcgttgaag actgggaaac gatgattgat    2520
accaacaaca aaggcctggt atatatgacg cgcgccgtct tacccgggtat ggttgaacgt    2580 aatcatggtc atattattaa cattggctca acggcaggta gctggccgta tgccggtggt    2640
aacgtttacg gtgcgacgaa agcgtttgtt cgtcagttta gcctgaatct gcgtacggat    2700
ctgcatggta cggcggtgcg cgtcaccgac atcgaaccgg gtctggtggg tggtaccgag    2760
ttttccaatg tccgctttaa aggcgatgac ggtaaagcag aaaaaaccta tcaaaatacc    2820
gttgcattga cgccagaaga tgtcagcgaa gccgtctggt gggtgtcaac gctgcctgct    2880
cacgtcaata tcaataccct ggaaatgatg ccggttaccc aaagctatgc cggactgaat    2940
gtccaccgtc agtaatagga tcgtcccggc ttatcggtca gtttcacctg atttacgtaa    3000
aaacccgctt cggcgggttt ttgcttttgg aggggcagaa agatgaatga ctgtccacga    3060
cgctataccc aaaagaaaga cgaattctct agatatcgct caatactgac catttaaatc    3120
atacctgacc tccatagcag aaagtcaaaa gcctccgacc ggaggctttt gacttgatcg    3180
gcacgtaaga ggttccaact ttcaccataa tgaaataaga tcactaccgg gcgtatttt    3240 tgagttatcg agattttcag gagctaagga agctaaaatg agccatattc aacgggaaac    3300
gtcttgctcg aggccgcgat taaattccaa catggatgct gatttatatg gtataaatg    3360 ggctcgcgat aatgtcgggc aatcaggtgc gacaatctat cgattgtatg ggaagcccga    3420
tgcgccagag ttgtttctga acatggcaa aggtagcgtt gccaatgatg ttacagatga    3480
gatggtcagg ctaaactggc tgacggaatt tatgcctctt ccgaccatca agcattttat    3540
ccgtactcct gatgatgcat ggttactcac cactgcgatc ccagggaaaa cagcattcca    3600
```

```
ggtattagaa gaatatcctg attcaggtga aatattgtt gatgcgctgg cagtgttcct    3660
gcgccggttg cattcgattc ctgtttgtaa ttgtccttt aacggcgatc gcgtatttcg    3720
tctcgctcag gcgcaatcac gaatgaataa cggtttggtt ggtgcgagtg attttgatga    3780
cgagcgtaat ggctggcctg ttgaacaagt ctggaaagaa atgcataagc ttttgccatt    3840
ctcaccggat tcagtcgtca ctcatggtga tttctcactt gataaccta ttttgacga    3900 ggggaaatta ataggttgta ttgatgttgg acgagtcgga atcgcagacc gataccagga    3960
tcttgccatc ctatggaact gcctcggtga gttttctcct tcattacaga aacggcttt    4020 tcaaaaatat ggtattgata atcctgatat gaataaattg cagtttcact tgatgctcga    4080 tgagttttc taatgagggc ccaaatgtaa tcacctggct caccttcggg tgggcctttc    4140
tgcgttgctg gcgtttttcc ataggctccg ccccctgac gagcatcaca aaatcgatg    4200 ctcaagtcag aggtggcgaa acccgacagg actataaaga taccaggcgt tccccctgg    4260 aagctccctc gtgcgctctc ctgttccgac cctgccgctt accggatacc tgtccgcctt    4320
tctcccttcg ggaagcgtgg cgctttctca tagctcacgc tgtaggtatc tcagttcggt    4380
gtaggtcgtt cgctccaagc tgggctgtgt gcacgaaccc cccgttcagc ccgaccgctg    4440
cgccttatcc ggtaactatc gtcttgagtc aaccccggta agacacgact tatcgccact    4500
ggcagcagcc actggtaaca ggattagcag agcgaggtat gtaggcggtg ctacagagtt    4560
cttgaagtgg tggcctaact acggctacac tagaagaaca gtatttggta tctgcgctct    4620
gctgaagcca gttaccttcgg aaaaagagtt ggtagctctt gatccggcaa acaaaccacc    4680
gctggtagcg gtggtttttt tgtttgcaag cagcagatta cgcgcagaaa aaaggatct    4740 caagaagatc ctttgatttt ctaccgaaga aaggcccacc cgtgaaggtg agccagtgag    4800
ttgattgcag tccagttacg ctggagtctg aggctcgtcc tgaatgatat caagcttgaa    4860
ttcgtt                                                              4866
```

<210> SEQ ID NO 31
<211> LENGTH: 3353
<212> TYPE: DNA
<213> ORGANISM: Artificial Sequence
<220> FEATURE:
<223> OTHER INFORMATION: Plasmid pSMART-F6AA82M

<400> SEQUENCE: 31

```
ccatggttga atgactccta taacgaagtt cacagctaac accacgtcgt ccctatctgc      60
tgccctaggt ctatgagtgg ttgctggata acgtgcgtaa ttgtgctgat ctcttatata     120
gctgctctca ttatctctct accctgaagt gactctctca cctgtaaaaa taatatctca     180
caggcttaat agtttcttaa tacaaagcct gtaaaacgtc aggataactt ctatattcag     240
ggagaccaca acggtttccc tctacaaata attttgttta actttcgaca tggcaaaatc     300
cccccctcgc gacttgctct tcagctttct ggaaaagga gatataccat gaatgttacg     360
tttgaagaac gtgcgagtct gcacggttac cgtatcggca ttgcaagctt ggatgccccg     420
gcttccttaa acgccttgag cctgcctatg atcgatgcgc tccaagatcg tttgcgcgct     480
tgggcggaag atgccgatat cgcttgcgtt ctgttacgtg gtaatggcag caaggcgttt     540
tgcgctggtg gcgatgtagt tcaattggcc aaaaaatgct tagcaagccc aggtgaagcc     600
ccggaactgg ccgagcgttt tttgccccgt agctatcgct tggatcatta tttgcacacc     660
taccccaaac cgttgatctg ttgggcccat ggtcacgtgc tgggtggtgg aatgggactt     720
ttacagggcg ccggcatccg tattgtgaca ccatcgtctc gcttagctat gccggaaatt     780
```

-continued

| | | | | |
|---|---|---|---|---|
| tctatcgggc | tgttccctga | cgtgggtggc | tcccatttcc | tgagtcgcct cccgggaaaa | 840 |
| ctggggttgt | ttttcggtct | taccgcgtct | cccettaacg | cacgcgacgc gctggactta | 900 |
| aatctggctg | accgtttcct | gcttgacacg | cagcaggatg | cgctgatcga tggtctgatt | 960 |
| cagttaaatt | ggcgcgagca | acctgatctg | cagctgcact | ctcttctgaa agctctggaa | 1020 |
| cagcaggctc | gtagtgagct | gccggccgct | cagtggttgc | ctcgtcgtga acgccttgat | 1080 |
| gccctcctgg | accaagccac | gttaccattg | tcctggcagg | cgctggcgtc gctcgaaaat | 1140 |
| gatgaggatg | ctctgttagc | taaggcagct | aaaacgatgc | tgggcggtag cccgctcacc | 1200 |
| ggccatctcg | tgtggggtca | aattcgtcgt | gcacgccacc | tgtccttggc gcaggtgttt | 1260 |
| cagatggaat | acggtatgtc | attgaactgc | tgccgccatc | cggagttcgc ggaaggcgtc | 1320 |
| cgcgcccgtt | tgattgacaa | ggatcacgcc | cccattggc | actggccgga cgttaaccag | 1380 |
| gttccggaac | aggtaattgc | agcgcatttc | gcgccattgg | atgatcaccc tttagccgat | 1440 |
| ctggcatagt | aaccggctta | tcggtcagtt | tcacctgatt | tacgtaaaaa cccgcttcgg | 1500 |
| cgggttttg | cttttggagg | ggcagaaaga | tgaatgactg | tccacgacgc tatcccaaa | 1560 |
| agaaagacga | attctctaga | tatcgctcaa | tactgaccat | ttaaatcata cctgacctcc | 1620 |
| atagcagaaa | gtcaaaagcc | tccgaccgga | ggcttttgac | ttgatcggca cgtaagaggt | 1680 |
| tccaactttc | accataatga | aataagatca | ctaccgggcg | tatttttga gttatcgaga | 1740 |
| ttttcaggag | ctaaggaagc | taaaatgagc | catattcaac | gggaaacgtc ttgctcgagg | 1800 |
| ccgcgattaa | attccaacat | ggatgctgat | ttatatgggt | ataaatgggc tcgcgataat | 1860 |
| gtcgggcaat | caggtgcgac | aatctatcga | ttgtatggga | agcccgatgc gccagagttg | 1920 |
| tttctgaaac | atggcaaagg | tagcgttgcc | aatgatgtta | cagatgagat ggtcaggcta | 1980 |
| aactggctga | cggaatttat | gcctcttccg | accatcaagc | attttatccg tactcctgat | 2040 |
| gatgcatggt | tactcaccac | tgcgatccca | gggaaaacag | cattccaggt attagaagaa | 2100 |
| tatcctgatt | caggtgaaaa | tattgttgat | gcgctggcag | tgttcctgcg ccggttgcat | 2160 |
| tcgattcctg | tttgtaattg | tccttttaac | ggcgatcgcg | tatttcgtct cgctcaggcg | 2220 |
| caatcacgaa | tgaataacgg | tttggttggt | gcgagtgatt | ttgatgacga gcgtaatggc | 2280 |
| tggcctgttg | aacaagtctg | gaaagaaatg | cataagcttt | tgccattctc accggattca | 2340 |
| gtcgtcactc | atggtgattt | ctcacttgat | aaccttattt | ttgacgaggg gaaattaata | 2400 |
| ggttgtattg | atgttggacg | agtcggaatc | gcagaccgat | accaggatct tgccatccta | 2460 |
| tggaactgcc | tcggtgagtt | ttctccttca | ttacagaaac | ggctttttca aaaatatggt | 2520 |
| attgataatc | ctgatatgaa | taaattgcag | tttcacttga | tgctcgatga gttttttctaa | 2580 |
| tgagggccca | aatgtaatca | cctggctcac | cttcgggtgg | gcctttctgc gttgctggcg | 2640 |
| tttttccata | ggctccgccc | cctgacgag | catcacaaaa | atcgatgctc aagtcagagg | 2700 |
| tggcgaaacc | cgacaggact | ataaagatac | caggcgtttc | ccctggaag ctccctcgtg | 2760 |
| cgctctcctg | ttccgaccct | gccgcttacc | ggatacctgt | ccgcctttct cccttcggga | 2820 |
| agcgtggcgc | tttctcatag | ctcacgctgt | aggtatctca | gttcggtgta ggtcgttcgc | 2880 |
| tccaagctgg | gctgtgtgca | cgaaccccc | gttcagcccg | accgctgcgc cttatccggt | 2940 |
| aactatcgtc | ttgagtccaa | cccggtaaga | cacgacttat | cgccactggc agcagccact | 3000 |
| ggtaacagga | ttagcagagc | gaggtatgta | ggcggtgcta | cagagttctt gaagtggtgg | 3060 |
| cctaactacg | gctacactag | aagaacagta | tttggtatct | gcgctctgct gaagccagtt | 3120 |

-continued

```
acctcggaaa aagagttggt agctcttgat ccggcaaaca aaccaccgct ggtagcggtg    3180 gttttttgt ttgcaagcag cagattacgc gcagaaaaaa aggatctcaa gaagatcctt    3240 tgatttcta ccgaagaaag gcccaccgt gaaggtgagc cagtgagttg attgcagtcc     3300
agttacgctg gagtctgagg ctcgtcctga atgatatcaa gcttgaattc gtt          3353
```

<210> SEQ ID NO 32
<211> LENGTH: 3424
<212> TYPE: DNA
<213> ORGANISM: Artificial Sequence
<220> FEATURE:
<223> OTHER INFORMATION: Plasmid pSMART-Ala1

<400> SEQUENCE: 32

```
ccaggcatca ataaaacga aaggctcagt cgaaagactg ggcctttcgt tttatctgtt     60
gtttgtcggt gaacgctctc tactagagtc acactggctc accttcgggt gggcctttct   120
gcgtttatac acagctaaca ccacgtcgtc cctatctgct gccctaggtc tatgagtggt   180
tgctggataa ctctttctga caccttacta tcttacaaat gtaacaaaaa agttattttt   240
ctgtaattcg agcatgtcat gttaccccgc gagcataaaa cgcgtatatt cagggagacc   300
acaacggttt ccctctacaa ataatttgt ttaactttgg aaaaaggaga tataccatga    360
tcattggggt gccgaaggag atcaaaaata tgagaaccg cgtcgcgttg accccgggag    420
gtgtcagcca gctgatctct aatggccatc gtgtcttagt tgaaacaggc gctggcctgg   480
gttctggctt cgaaaacgag gcctacgaat ctgcaggtgc ggaaattatt gctgatccaa   540
aacaggtctg ggatgcagag atggtcatga aagtgaaaga accgctcccg gaagaatatg   600 tctatttcg taaggtctg gtgctgttta catatctgca tctggcagct gaaccggagc    660
tcgcacaagc ccttaaagat aaaggtgtca cggccatcgc atacgaaact gtcagcgaag   720 gcgcacgct gccattactg accccgatgt cagaagtggc aggccgtatg gctgcgcaga   780
tcggcgcaca gttccttgaa aaaccaaagg gcggaagg tattctctta gcaggagtgc    840
cgggcgtcag tcgtgggaaa gtaactatta ttggtggcgg cgtggtagga acaaatgctg   900
ccaaaatggc cgtcggtttg ggggccgacg taacaatcat tgcgcgtaat gccgatcgcc   960
ttcgtcaatt agacgatatc tttggccacc aaatcaaaac cctgatttcg aacccagtca  1020
atatcgcgga tgcggtggcg gaagctgatt tgttgatctg cgccgtgtta attccgggag  1080
cgaaagcacc tacattggtg acggaagaaa tggtgaaaca aatgaaaccg ggttcagtca  1140
ttgttgatgt ggctattgat cagggtggca ctcgtggaaac ggtggaccat attaccactc  1200
acgaccagcc gacgtatgaa aaacatggtg tcgtacacta tgcggtggcg aatatgcctg  1260
gtgcggtccc acgtacgagt acaatcgcac tgacaaatgt caccgtgccg tatgcgttgc  1320
aaatcgcgaa caaaggtgcc gtgaaagcgc tggccgacaa tacggcgtta cgtgccggtc  1380
tgaacaccgc taacggtcac gtgacatatg aagcggtcgc gcgtgatttg ggtacgaat   1440 atgtaccggc ggaaaaagcc ttacaagacg aatcgagtgt cgctggtgca tagtaagctc  1500
ttctaatacg actcactata gggccggctt atcggtcagt ttcacctgat ttacgtaaaa  1560
acccgcttcg gcgggttttt gcttttggag gggcagaaag atgaatgact gtccacgacg  1620
ctatacccaa aagaaagacg aattctctag atatcgctca atactgacca tttaaatcat  1680
acctgacctc catagcagaa agtcaaaagc ctccgaccgg aggcttttga cttgatcggc  1740
acgtaagagg ttccaacttt caccataatg aaataagatc actaccgggc gtattttttg  1800
agttatcgag attttcagga gctaaggaag ctaaaatgag ccatattcaa cgggaaacgt  1860
```

| | |
|---|---|
| cttgctcgag gccgcgatta aattccaaca tggatgctga tttatatggg tataaatggg | 1920 |
| ctcgcgataa tgtcgggcaa tcaggtgcga caatctatcg attgtatggg aagcccgatg | 1980 |
| cgccagagtt gtttctgaaa catggcaaag gtagcgttgc caatgatgtt acagatgaga | 2040 |
| tggtcaggct aaactggctg acggaattta tgcctcttcc gaccatcaag cattttatcc | 2100 |
| gtactcctga tgatgcatgg ttactcacca ctgcgatccc agggaaaaca gcattccagg | 2160 |
| tattagaaga atatcctgat tcaggtgaaa atattgttga tgcgctggca gtgttcctgc | 2220 |
| gccggttgca ttcgattcct gtttgtaatt gtccttttaa cggcgatcgc gtatttcgtc | 2280 |
| tcgctcaggc gcaatcacga atgaataacg gtttggttgg tgcgagtgat tttgatgacg | 2340 |
| agcgtaatgg ctggcctgtt gaacaagtct ggaaagaaat gcataagctt ttgccattct | 2400 |
| caccggattc agtcgtcact catggtgatt tctcacttga taaccttatt tttgacgagg | 2460 |
| ggaaattaat aggttgtatt gatgttggac gagtcggaat cgcagaccga taccaggatc | 2520 |
| ttgccatcct atggaactgc ctcggtgagt tttctccttc attacagaaa cggcttttc | 2580 |
| aaaaatatgg tattgataat cctgatatga ataaattgca gtttcacttg atgctcgatg | 2640 |
| agttttctta atgagggccc aaatgtaatc acctggctca ccttcgggtg gcctttctg | 2700 |
| cgttgctggc gttttccat aggctccgcc ccctgacga gcatcacaaa aatcgatgct | 2760 |
| caagtcagag gtggcgaaac ccgacaggac tataaagata ccaggcgttt ccccctggaa | 2820 |
| gctccctcgt gcgctctcct gttccgaccc tgccgcttac cggatacctg tccgcctttc | 2880 |
| tcccttcggg aagcgtggcg ctttctcata gctcacgctg taggtatctc agttcggtgt | 2940 |
| aggtcgttcg ctccaagctg ggctgtgtgc acgaaccccc cgttcagccc gaccgctgcg | 3000 |
| ccttatccgg taactatcgt cttgagtcca acccggtaag acacgactta tcgccactgg | 3060 |
| cagcagccac tggtaacagg attagcagag cgaggtatgt aggcggtgct acagagttct | 3120 |
| tgaagtggtg gcctaactac ggctacacta agaacagt atttggtatc tgcgctctgc | 3180 |
| tgaagccagt tacctcggaa aaagagttgg tagctcttga tccggcaaac aaaccaccgc | 3240 |
| tggtagcggt ggtttttttg tttgcaagca gcagattacg cgcagaaaaa aaggatctca | 3300 |
| agaagatcct ttgatttct accgaagaaa ggcccacccg tgaaggtgag ccagtgagtt | 3360 |
| gattgcagtc cagttacgct ggagtctgag gctcgtcctg aatgatatca gcttgaatt | 3420 |
| cgtt | 3424 |

<210> SEQ ID NO 33
<211> LENGTH: 6275
<212> TYPE: DNA
<213> ORGANISM: Artificial Sequence
<220> FEATURE:
<223> OTHER INFORMATION: Plasmid pSMART-Mev1

<400> SEQUENCE: 33

| | |
|---|---|
| tgcccaggca tcaaataaaa cgaaaggctc agtcgaaaga ctgggccttt cgttttatct | 60 |
| gttgtttgtc ggtgaacgct ctctactaga gtcacactgg ctcaccttcg ggtgggcctt | 120 |
| tctgcgttta tacacagcta acaccacgtc gtccctatct gctgccctag gtctatgagt | 180 |
| ggttgctgga taacgtgcgt aattgtgctg atctcttata tagctgctct cattatctct | 240 |
| ctaccctgaa gtgactctct cacctgtaaa ataatatct cacaggctta atagtttctt | 300 |
| aatacaaagc ctgtaaaacg tcaggataac ttctatattc agggagacca caacggtttc | 360 |
| cctctacaaa taattttgtt taactttcgt ggaaaaagga gatataccat gaagacggta | 420 |

```
gttattatcg acgcactgcg taccccatt ggaaaataca aaggaagtct gagccaggta      480
agcgccgtcg acctgggcac acatgtgacc acgcagttgt tgaagcgtca cagcactatc      540
agcgaggaaa ttgatcaggt cattttggt aatgttctgc aggcgggcaa tgggcagaac      600
cctgcacgtc agattgcaat caactcaggt ttaagccatg aaattccagc gatgacggtc      660
aatgaggtct gtggcagtgg gatgaaagcg gtaatcctgg ccaaacagtt aatccagctg      720
ggtgaggcgg aggtacttat cgcaggtggt attgaaaaca tgtcacaggc cccgaaactg      780
caacgcttta actacgaaac agaaagctac gatgcgcctt tttcgtccat gatgtatgat      840
ggtcttaccg acgcattcag tggtcaggcg atgggtctga cggccgagaa tgttgctgaa      900
aaataccacg ttacccgtga ggaacaagac caattctctg tccatagcca actcaaagcg      960
gcacaggctc aggcagaagg catttttgcc gatgagattg caccactgga gtttccggc      1020 accctggtgg aaaaggacga gggcattcgt ccgaatagca gtgttgaaaa actcggtact      1080
ttgaaaaccg tattcaaaga ggacggcacg tgactgccg gtaatgcctc aactatcaac      1140
gacggtgcct cggcactgat tattgcgtct caagaatacg cggaagcgca cggcttgccg      1200
tatctcgcga ttatccgcga ttcagtggag gtcggcatcg atcccgcgta catgggcatt      1260
tcgccgatca aagcaattca gaagcttctg cacgcaacc agttgacgac cgaagagatt      1320
gatttatacg aaatcaatga agcgttcgcg gcgacctcga ttgtggttca gcgtgaactt      1380
gccctcccgg aagaaaaggt caacatctat ggcggaggca tcagtttggg ccatgccatc      1440
ggagcgaccg gtgcccgtct gctcaccagc ttatcatatc agttgaacca gaaagaaaaa      1500
aagtacggcg ttgcatctct gtgtattggc ggaggtctgg gcctcgccat gttgttagaa      1560
cgtccgcagc aaaaaaaaa ctcccgcttt tatcagatgt cgccggagga acgtctggcg      1620
agcttgttga acgaagggca gatctctgcc gacactaaaa aggaattcga aaacacggca      1680
ctgagcagtc agattgcgaa ccatatgatt gaaaatcaga tcagcgagac cgaggtgccc      1740
atgggcgtgg gccttcatct cacggtggac gaaacggatt atctggtacc aatgccaca      1800 gaagaaccgt cggtaatcgc cgcgttgtca aatggcgcga aaatcgcgca agggttcaaa      1860
acggtcaacc agcagcgtct catgcgcggc cagatcgtgt tctatgatgt agcagatgca      1920
gagagtctga ttgacgagtt acaggttcgt gagacggaga ttttcagca agccgagctg      1980 tcgtacccga gcattgttaa acgtggcggt ggccttcgtg acttgcagta tcgcgccttc      2040
gacgaatcgt tcgtgagtgt cgactttctg gtagacgtga aggacgccat gggggccaat      2100
atcgttaatg ccatgctgga aggggttgca gagctgtttc gtgagtggtt cgccgaacaa      2160
aaaatcctgt ttagcatctt aagcaattac gcaacggaaa gcgtcgtgac catgaaaacc      2220
gcgatccctg ttagccgcct ttcaaagggc agtaacggtc gtgaaatcgc tgaaaaaatt      2280
gttctcgcgt cccgctatgc atcgttggat ccttatcgcg cggtgacaca caacaaaggc      2340
attatgaatg gtatcgaagc ggtcgttctg cgcaccggca acgatactcg cgccgtgagc      2400
gcgtcctgcc atgcttttgc tgtgaaagag ggccgttatc agggcttgac gtcctggacc      2460
ctggacggtg aacagctgat cggcgaaatc tcggtgcccc tcgccctggc cactgtgggc      2520
ggcgccacaa aagtgttgcc aaaaagccaa gcggcggcgg atctgctggc cgtaactgat      2580
gctaaggaac tgagtcgcgt ggttgccgca gtgggcctgg cccaaaacct ggcagcactg      2640
cgcgcgctgg tttctgaagg catccagaaa ggtcatatgg ccctgcaagc gcgctctctg      2700
gccatgaccg taggggcgac cggcaaggaa gtcgaagcgg tagctcaaca gttaaaacgc      2760
cagaaaacta tgaatcagga tcgtgcgctg gccatcctca atgacctgcg caaacagtaa      2820
```

```
tagtcgcgcc gaaaacccg cttcggcggg gttttgccgc acgtctccat cgcttgccca    2880
agttgtgaag cacagctaac accacgtcgt ccctatctgc tgcccctaggt ctatgagtgg   2940
ttgctggata accatccata aattttgcat aattaatgta aagaccaggc tcgccagtaa   3000
cgctaaattc atttggctgt aagcgcggtg tcatccgcgt caggaaaatt aaacagttac   3060
tttaaaaaat gaaaacgtaa aaaggttggg tttcgatgta ttgacgggta aactttgtcg   3120
cccgctaaac atttgtttat attcagggag accacaacgg tttccctcta caaataattt   3180
tgtttaactt tgctggaaaa aggagatata ccatgaccat gggattgat aaaatctcgt    3240
ttttcgtgcc tccttattat atcgacatga cggccctggc cgaggctcgc aatgtggatc   3300
ccggcaaatt tcacatcggt atcggccagg accaaatggc ggtgaatccc atctcgcagg   3360
acattgtcac cttcgccgca aacgcagcag aagctatctt gactaaagaa gataaagagg   3420
ccatcgacat ggtgatcgtg ggtacggaaa gctctattga cgaaagtaaa gccgcggcgg   3480
tggtattaca ccgcctgatg ggtatccagc cgtttgcgcg ctcctttgaa atcaaagagg   3540
cctgctacgg cgcaacggct ggactgcaac tcgcgaagaa ccatgttgca ttacatccgg   3600
ataaaaaagt cctggttgtc gcggcggaca tcgcgaaata cggcctgaac tccggcgggg   3660
aaccaacgca gggtgccggc gcagtggcga tgcttgtcgc aagcgagcct cgtatcctgg   3720
ctttaaagga ggacaacgtg atgctgacac aggatattta cgattttgg cgtcccaccg    3780
gtcatccata tccgatggtt gatggtcctc tgtccaatga aacttatatt cagagcttcg   3840
cgcaagtttg ggatgaacat aagaaacgta ccggtctgga ttttgcggat tacgacgctc   3900
tggcttttca cattccatac acgaaaatgg gcaaaaaagc cctcttagct aaaatctcag   3960
accagaccga ggcagaacag gaacgcattt tagcgcgtta cgaagagtca attatctaca   4020
gccgccgtgt aggtaattta tatacggggt cgctttatct gggattgatt tccttactcg   4080
aaaacgccac aaccctgacg gcgggtaacc aaatcggttt attctcttac ggtagcggtg   4140
ccgttgccga attcttcacg ggtgagctgg ttgccggtta ccagaaccac ttacagaaag   4200
aaacccacct cgccctgctg gacaaccgta ctgaactcag catcgcgaaa tatgaggcca   4260
tgttcgccga aacactcgac acggatatcg atcaaacctt agaggatgaa ctcaaatatt   4320
ccatttcagc gattaataac accgtccgct cctatcgcaa ttagtaagat cgtcccggct   4380
tatcggtcag tttcacctga tttacgtaaa aacccgcttc ggcgggtttt tgcttttgga   4440
ggggcagaaa gatgaatgac tgtccacgac gctatcccaa aaagaaagac gaattctcta   4500
gatatcgctc aatactgacc atttaaatca tacctgacct ccatagcaga aagtcaaaag   4560
cctccgaccg gaggcttttg acttgatcgg cacgtaagag gttccaactt tcaccataat   4620
gaaataagat cactaccggg cgtatttttt gagttatcga gattttcagg agctaaggaa   4680
gctaaaatga gccatattca acgggaaacg tcttgctcga ggccgcgatt aaattccaac   4740
atggatgctg atttatatgg gtataaatgg gctcgcgata atgtcgggca atcaggtgcg   4800
acaatctatc gattgtatgg gaagcccgat gcgccagagt tgtttctgaa acatggcaaa   4860
ggtagcgttg ccaatgatgt tacagatgag atggtcaggc taaactggct gacggaattt   4920
atgcctcttc cgaccatcaa gcattttatc cgtactcctg atgatgcatg ttactcacc    4980
actgcgatcc cagggaaaac agcattccag gtattagaag aatatcctga ttcaggtgaa   5040
aatattgttg atgcgctggc agtgttcctg cgccggttgc attcgattcc tgtttgtaat   5100
tgtccttta acggcgatcg cgtatttcgt ctcgctcagg cgcaatcacg aatgaataac   5160
```

| | |
|---|---:|
| ggtttggttg gtgcgagtga ttttgatgac gagcgtaatg gctggcctgt tgaacaagtc | 5220 |
| tggaaagaaa tgcataagct tttgccattc tcaccggatt cagtcgtcac tcatggtgat | 5280 |
| ttctcacttg ataaccttat ttttgacgag gggaaattaa taggttgtat tgatgttgga | 5340 |
| cgagtcggaa tcgcagaccg ataccaggat cttgccatcc tatggaactg cctcggtgag | 5400 |
| ttttctcctt cattacagaa acggcttttt caaaaatatg gtattgataa tcctgatatg | 5460 |
| aataaattgc agtttcactt gatgctcgat gagttttttct aatgagggcc caaatgtaat | 5520 |
| cacctggctc accttcgggt gggcctttct gcgttgctgg cgttttttcca taggctccgc | 5580 |
| cccccctgacg agcatcacaa aaatcgatgc tcaagtcaga ggtggcgaaa cccgacagga | 5640 |
| ctataaagat accaggcgtt tccccctgga agctccctcg tgcgctctcc tgttccgacc | 5700 |
| ctgccgctta ccggatacct gtccgccttt ctcccttcgg gaagcgtggc gctttctcat | 5760 |
| agctcacgct gtaggtatct cagttcggtg taggtcgttc gctccaagct gggctgtgtg | 5820 |
| cacgaacccc ccgttcagcc cgaccgctgc gccttatccg gtaactatcg tcttgagtcc | 5880 |
| aacccggtaa gacacgactt atcgccactg gcagcagcca ctggtaacag gattagcaga | 5940 |
| gcgaggtatg taggcggtgc tacagagttc ttgaagtggt ggcctaacta cggctacact | 6000 |
| agaagaacag tatttggtat ctgcgctctg ctgaagccag ttaccttcgga aaaagagttg | 6060 |
| gtagctcttg atccggcaaa caaaccaccg ctggtagcgg tggttttttt gtttgcaagc | 6120 |
| agcagattac gcgcagaaaa aaggatctca agaagatcc tttgattttc taccgaagaa | 6180 |
| aggcccaccc gtgaaggtga gccagtgagt tgattgcagt ccagttacgc tggagtctga | 6240 |
| ggctcgtcct gaatgatatc aagcttgaat tcgtt | 6275 |

<210> SEQ ID NO 34
<211> LENGTH: 5364
<212> TYPE: DNA
<213> ORGANISM: Artificial Sequence
<220> FEATURE:
<223> OTHER INFORMATION: Plasmid pSMART-2,3-BDO1

<400> SEQUENCE: 34

| | |
|---|---:|
| gtgcgtaatt gtgctgatct cttatatagc tgctctcatt atctctctac cctgaagtga | 60 |
| ctctctcacc tgtaaaaata atatctcaca ggcttaatag tttcttaata caaagcctgt | 120 |
| aaaacgtcag gataacttct tggaaaaagg agatatacca tgatgcacag cagcgcatgt | 180 |
| gattgtgaag cgagtttgtg cgagacactc cgtggttttt ccgcaaaaca cccggattcc | 240 |
| gtaatctacc agacatcact gatgtccgcc cttctgtcag gcgtatatga aggggacacg | 300 |
| actattgcgg atcttctggc ccacggcgat tttggcctgg gtacgttcaa tgaactcgac | 360 |
| ggcgaaatga tcgcgttttc ttcgcaagtt tatcagctcc gtgcggatgg gagcgcccgc | 420 |
| gccgcgaagc cagaacaaaa aacaccgttt gcagtaatga catggttcca accgcagtat | 480 |
| cgtaaaactt tcgatgcccc ggtgagtcgt cagcagatcc acgatgtaat cgatcaacag | 540 |
| attccttcag acaacctgtt ttgcgcgctg cgtattgacg ggaatttccg tcatgctcac | 600 |
| acacgtaccg ttccgcgcca gaccccaccc tatcgcgcga tgaccgatgt gctggatgat | 660 |
| caaccggtct ttcgttttaa ccagcgcgaa ggagttctgg tgggttttcg taccccgcaa | 720 |
| catatgcagg gtattaacgt ggcgggctac catgagcatt tcattacaga tgatcgccaa | 780 |
| ggcggtggtc acctgttgga ttaccagctg gaatctggcg tcctgacttt cggcgagatt | 840 |
| cacaaactga tgattgacct gccggtggat tctgcattcc tgcaggcaaa tttgcaccccc | 900 |
| agcaaccttg atgccgccat ccgctccgtc gagaactaat aggctcttca cttctggaaa | 960 |

| | |
|---|---|
| aaggagatat accatgaatt ccgaaaaaca atcgcgtcag tgggcacatg gtgctgatat | 1020 |
| ggttgtgggc cagctggagg cgcagggggt taaacaggtc tttggtattc cgggtgctaa | 1080 |
| gatcgacaaa gtgtttgatt ctttactgga tagctcaatc gagattatcc cggtgcgtca | 1140 |
| tgaagcaaac gcagcgttca tggccgcggc agttggtcgc cttacgggta aagctggcgt | 1200 |
| agccctggtc acaagcggcc ccgggtgctc gaatctcatt accggcattg caaccgcaaa | 1260 |
| ttctgaggga gatcctgtag tggcactggg gggcgcggta aaacgtgctg ataaagcgaa | 1320 |
| attagttcac cagagtatgg acaccgtcgc gatgttctct ccagtaacca aatatgcggt | 1380 |
| tgaagtttct tccccagatg caattgcaga ggtagtatca aacgcttttc gtgccgcgga | 1440 |
| acatggccgc ccaggtgggg cgttcgtttc gctgccgcag gatattgtag accaaccggc | 1500 |
| gacaggcgca atcctgcctg catctggccc ggcactgatg ggcccagcgc cagagtcggc | 1560 |
| gattaacgat gtggcaaaac ttatcgacaa cgccaaaaac cctgtgattc tgttgggctt | 1620 |
| aatggcatca cagccggcta attcggctgc attgcgtaag ctgctggaga agagtcgcat | 1680 |
| cccggtgact tccacctacc aagccgccgg agctgtgaac caagaacatt tcacccgctt | 1740 |
| cgccggtcgt gttggccttt tcaataacca agcgggagac cgtctgctgc atttggccga | 1800 |
| tctcattatc tgtattggat actctccagt cgagtatgaa ccgagcatgt ggaactcggg | 1860 |
| tgacgcaacc ctcgttcata ttgacgtgct gccagcttat gaagaacgca actatgtacc | 1920 |
| cgatatcgag ttggtaggcg acattgcggc gacactgaac ctgctcgctt cccgcattga | 1980 |
| tcataaactg gagctctcgc agcgtgcctc cgagatctta gtcgatcgcc aacaccagcg | 2040 |
| cgatctgctg gatcgccgtg gcgcaagctt aaatcaattt gcgctgcatc cattacgtat | 2100 |
| cgtccgtgcc atgcaggaca tcgtaaacaa tgacgtaacg ctgaccgtgg acatgggctc | 2160 |
| atttcatatt tggatcgcac gctatctcta ttcatttcgc gcacgtcagg tcatgattag | 2220 |
| taatgggcaa caaactatgg gcgtggctct gccttgggct atcggtgcgt ggctggtgaa | 2280 |
| ccccggccgc aaagtggtga cgttagcgg tgacggagga tttctgcaga gtagcatgga | 2340 |
| gttagaaacc gctgtccgcc tgaacgctaa tgtgttacac atcatttggg tggataatgg | 2400 |
| ttataatatg gttgcaatcc aggaggagaa aaagtatcag cgtttaagcg gtgtggcgtt | 2460 |
| tggaccggta gatttcaaag cctacgccga tgcattcggc gcccgtggct tcgcggtcga | 2520 |
| aagcgcggat gccttagaga gcaccttacg tgcggcaatg gatgtgaatg gtccggccgt | 2580 |
| cgtggcgatt ccggtggatt attcggataa tccgctgctg atgggacaac tgcaccttc | 2640 |
| gcagatcctg tagtaagctc ttctggaaaa aggagatata ccatgcagaa ggtggcgctc | 2700 |
| gttaccggat ctggccaagg cattggcaaa gcgattgcgc ttcgtctggt caaagacgga | 2760 |
| ttcgccgttg caattgctga ttacaacgac gaaacgcgc gtgctgtcgc cgatgaaatc | 2820 |
| atccgtaatg gtggcaacgc tgtcgcagtg aaagtggacg tctctgatcg cgaccaagta | 2880 |
| tttgcagcgt tcgagaaagc acgtaccgct ctgggcggtt tcaacgttat cgtgaacaac | 2940 |
| gcgggcattg cgccgtcgac gcctatcgaa agcatcaccc cggagattgt agataaggtg | 3000 |
| tacaacatca acgtaaaagg agtaatctgg ggtatgcaag ctgccatcga tgcgttccgc | 3060 |
| aaagaggggc acgcggtaa aatcattaac gcgtgttcgc aggctggtca tactggtaac | 3120 |
| ccggaactgg cggtttatag cagcagcaaa ttcgccgtgc gtggcctgac ccagaccgct | 3180 |
| gcacgcgatc tggcgccgct ggggatcacc gtcaatgcat attgtccggg tatcgtaaaa | 3240 |
| accccgatgt gggcggaaat tgatcgccag gtatcagagg ccgctggcaa accgctgggc | 3300 |

```
tatggcacgg aaacgtttgc caagcgcatc acgttaggcc gtctgtcgga accggaggat    3360
gttgcagcat gcgtctctta cctggcgggc ccggattctg attatatgac gggtcagtcc    3420
ctgctgattg atggtggcat ggtctttaac tagtaagatc gtcccggctt atcggtcagt    3480
ttcacctgat ttacgtaaaa acccgcttcg gcgggttttt gcttttggag gggcagaaag    3540
atgaatgact gtccacgacg ctatacccaa agaaagacg aattctctag atatcgctca     3600
atactgacca tttaaatcat acctgacctc catagcagaa agtcaaaagc ctccgaccgg    3660
aggcttttga cttgatcggc acgtaagagg ttccaacttt caccataatg aaataagatc    3720
actaccgggc gtattttttg agttatcgag attttcagga gctaaggaag ctaaaatgag    3780
ccatattcaa cgggaaacgt cttgctcgag gccgcgatta aattccaaca tggatgctga    3840
tttatatggg tataaatggg ctcgcgataa tgtcgggcaa tcaggtgcga caatctatcg    3900
attgtatggg aagcccgatg cgccagagtt gtttctgaaa catggcaaag gtagcgttgc    3960
caatgatgtt acagatgaga tggtcaggct aaactggctg acggaattta tgcctcttcc    4020
gaccatcaag cattttatcc gtactcctga tgatgcatgg ttactcacca ctgcgatccc    4080
agggaaaaca gcattccagg tattagaaga atatcctgat tcaggtgaaa atattgttga    4140
tgcgctggca gtgttcctgc gccggttgca ttcgattcct gtttgtaatt gtccttttaa    4200
cggcgatcgc gtatttcgtc tcgctcaggc gcaatcacga atgaataacg gtttggttgg    4260
tgcgagtgat tttgatgacg agcgtaatgg ctggcctgtt gaacaagtct ggaaagaaat    4320
gcataagctt ttgccattct caccggattc agtcgtcact catggtgatt tctcacttga    4380
taaccttatt tttgacgagg ggaaattaat aggttgtatt gatgttggac gagtcggaat    4440
cgcagaccga taccaggatc ttgccatcct atggaactgc ctcggtgagt tttctccttc    4500
attacagaaa cggcttttttc aaaaatatgg tattgataat cctgatatga ataaattgca    4560
gtttcacttg atgctcgatg agttttttcta atgagggccc aaatgtaatc acctggctca    4620
ccttcgggtg ggcctttctg cgttgctggc gttttttccat aggctccgcc ccctgacga    4680
gcatcacaaa aatcgatgct caagtcagag gtggcgaaac ccgacaggac tataaagata    4740
ccaggcgttt ccccctggaa gctccctcgt gcgctctcct gttccgaccc tgccgcttac    4800
cggatacctg tccgcctttc tcccttcggg aagcgtggcg ctttctcata gctcacgctg    4860
taggtatctc agttcggtgt aggtcgttcg ctccaagctg ggctgtgtgc acgaaccccc    4920
cgttcagccc gaccgctgcg ccttatccgg taactatcgt cttgagtcca acccggtaag    4980
acacgactta tcgccactgg cagcagccac tggtaacagg attagcagag cgaggtatgt    5040
aggcggtgct acagagttct tgaagtggtg gcctaactac ggctacacta agaacagt     5100
atttggtatc tgcgctctgc tgaagccagt tacctcggaa aaagagttgg tagctcttga    5160
tccggcaaac aaaccaccgc tggtagcggt ggtttttttg tttgcaagca gcagattacg    5220
cgcagaaaaa aaggatctca agaagatcct ttgatttct accgaagaaa ggcccacccg    5280
tgaaggtgag ccagtgagtt gattgcagtc cagttacgct ggagtctgag gctcgtcctg    5340
aatgatatca agcttgaatt cgtt                                          5364
```

<210> SEQ ID NO 35
<211> LENGTH: 5748
<212> TYPE: DNA
<213> ORGANISM: Artificial Sequence
<220> FEATURE:
<223> OTHER INFORMATION: Plasmid pSMART-2,3-BDO2

<400> SEQUENCE: 35

```
gtgcgtaatt gtgctgatct cttatatagc tgctctcatt atctctctac cctgaagtga    60
ctctctcacc tgtaaaaata atatctcaca ggcttaatag tttcttaata caaagcctgt   120
aaaacgtcag gataacttct tggaaaaagg agatatacca tgatgcacag cagcgcatgt   180
gattgtgaag cgagtttgtg cgagacactc cgtggttttt ccgcaaaaca cccggattcc   240
gtaatctacc agacatcact gatgtccgcc cttctgtcag gcgtatatga aggggacacg   300
actattgcgg atcttctggc ccacggcgat tttggcctgg gtacgttcaa tgaactcgac   360
ggcgaaatga tcgcgttttc ttcgcaagtt tatcagctcc gtgcggatgg gagcgcccgc   420
gccgcgaagc cagaacaaaa aacaccgttt gcagtaatga catggttcca accgcagtat   480
cgtaaaactt tcgatgcccc ggtgagtcgt cagcagatcc acgatgtaat cgatcaacag   540
attccttcag acaacctgtt ttgcgcgctg cgtattgacg ggaatttccg tcatgctcac   600
acacgtaccg ttccgcgcca gaccccaccc tatcgcgcga tgaccgatgt gctggatgat   660
caaccggtct ttcgttttaa ccagcgcgaa ggagttctgg tgggttttcg taccccgcaa   720
catatgcagg gtattaacgt ggcgggctac catgagcatt tcattacaga tgatcgccaa   780
ggcggtggtc acctgttgga ttaccagctg gaatctggcg tcctgacttt cggcgagatt   840
cacaaactga tgattgacct gccggcggat tctgcattcc tgcaggcaaa tttgcaccccc   900 agcaaccttg atgccgccat ccgctccgtc gagaactaat aggctcttca cttctggaaa   960
aaggagatat accatgaatt ccgaaaaaca atcgcgtcag tgggcacatg gtgctgatat  1020
ggttgtgggc cagctggagg cgcaggggggt taaacaggtc tttggtattc cgggtgctaa  1080
gatcgacaaa gtgtttgatt ctttactgga tagctcaatc gagattatcc cggtgcgtca  1140
tgaagcaaac gcagcgttca tggccgcggc agttggtcgc cttacgggta aagctggcgt  1200
agccctggtc acaagcggcc ccgggtgctc gaatctcatt accggcattg caaccgcaaa  1260
ttctgaggga gatcctgtag tggcactggg gggcgcggta aaacgtgctg ataaagcgaa  1320
attagttcac cagagtatgg acaccgtcgc gatgttctct ccagtaacca aatatgcggt  1380
tgaagtttct tccccagatg caattgcaga ggtagtatca aacgcttttc gtgccgcgga  1440
acatggccgc ccaggtgggg cgttcgtttc gctgccgcag gatattgtag accaaccggc  1500
gacaggcgcc atcctgcctg catctggccc ggcactgatg ggcccagcgc cagagtcggc  1560
gattaacgat gtgcaaaac ttatcgacaa cgccaaaaac cctgtgattc tgttgggctt  1620
aatggcatca cagccggcta attcggctgc attgcgtaag ctgctggaga gagtcgcat  1680 cccggtgact tccacctacc aagccgccgg agctgtgaac caagaacatt tcaccgcctt  1740
cgccggtcgt gttggccttt tcaataacca agcgggagac cgtctgctgc atttggccga  1800
tctcattatc tgtattggat actctccagt cgagtatgaa ccgagcatgt ggaactcggg  1860
tgacgcaacc ctcgttcata ttgacgtgct gccagcttat gaagaacgca actatgtacc  1920
cgatatcgag ttggtaggcg acattgcggc gacactgaac ctgctcgctt cccgcattga  1980
tcataaactg gagctctcgc agcgtgcctc cgagatctta gtcgatcgcc aacaccagcg  2040
cgatctgctg gatcgccgtg gcgcaagctt aaatcaattt gcgctgcatc cattacgtat  2100
cgtccgtgcc atgcaggaca tcgtaaacaa tgacgtaacg ctgaccgtgg acatgggctc  2160
atttcatatt tggatcgcac gctatctcta ttcatttcgc gcacgtcagg tcatgattag  2220
taatgggcaa caaactatgg gcgtggctct gccttgggct atcggtgcgt ggctggtgaa  2280
ccccggccgc aaagtggtga gcgttagcgg tgacggagga tttctgcaga gtagcatgga  2340
```

```
gttagaaacc gctgtccgcc tgaacgctaa tgtgttacac atcatttggg tggataatgg      2400
ttataatatg gttgcaatcc aggaggagaa aaagtatcag cgtttaagcg gtgtggcgtt      2460
tggaccggta gatttcaaag cctacgccga tgcattcggc gcccgtggct tcgcggtcga      2520
aagcgcggat gccttagaga gcaccttacg tgcggcaatg gatgtgaatg gtccggccgt      2580
cgtggcgatt ccggtggatt attcggataa tccgctgctg atgggacaac tgcacctttc      2640
gcagatcctg tagtaagctc ttctggaaaa aggagatata ccatgcgtgc gttggcatat      2700
ttcaaaaaag gagacatcca ctttaccaac gatattccgc gtccggagat ccagacggat      2760
gatgaagtga ttattgatgt gagctggtgt gggatttgcg gttcggattt gcatgaatat      2820
ctggatggtc caatttttat gccgaaggat ggcgaatgtc acaaactgag taacgcggcg      2880
ctgcccctgg caatgggaca cgagatgtcg ggaattgtca gtaaagtcgg cccgaaagtg      2940
accaaggtca agtgggcga tcatgttgtt gttgatgctg catcgtcctg tgccgatctc      3000
cattgctggc cccacagcaa attctataac tctaaacctt gtgacgcgtg tcaacgcgga      3060
tcggagaacc tgtgcacgca tgccggtttt gtcgggcttg gggttatctc tggcggtttt      3120
gcggaacaag tggtggtatc tcaacatcac attattcccg tgccgaagga aatccctctg      3180
gacgtagcag cactggtgga accgctctcg gtaacctggc acgcagtaaa aatttcgggc      3240
tttaagaaag gctcgagtgc actggtgttg ggggccggcc caatcggtct gtgtacgatt      3300
ctggtgctga aagtatggg tgcgagcaaa atcgtagtta gttcgcgttc cgagcgtcgc      3360
atcgaaatgg caaaaaaact cggcgtcgaa gtgtttaatc catcgaaaca cggccataag      3420
agtattgaaa ttctgcgtgg tctgaccaaa tcacatgacg gtttcgatta tagctatgac      3480
tgcagtggaa ttcaggttac cttcgaaacc agccttaaag cccttacttt taaaggcacc      3540
gccaccaata tcgctgtttg gggtcccaaa cccgtacctt ccagcctat ggatgtgaca      3600 cttcaggaaa aagttatgac gggatccatc ggctacgtgg tggaggactt cgaagaagtg      3660
gtccgtgcca ttcacaacgg agatatcgcg atggaagatt gtaagcagct gattaccggc      3720
aaacagcgca ttgaggatgg gtgggaaaaa ggcttccagg aattaatgga ccacaaagag      3780
tctaatgtaa aaattctgct gaccccgaat aatcatggag aaatgaaata gtaatagtaa      3840
gatcgtcccg gcttatcggt cagtttcacc tgatttacgt aaaaaccgc ttcggcgggt      3900 ttttgctttt ggagggggcag aaagatgaat gactgtccac gacgctatac ccaaaagaaa      3960
gacgaattct ctagatatcg ctcaatactg accatttaaa tcatacctga cctccatagc      4020
agaaagtcaa aagcctccga ccggaggctt ttgacttgat cggcacgtaa gaggttccaa      4080 cttttcaccat aatgaaataa gatcactacc gggcgtattt tttgagttat cgagattttc      4140
aggagctaag gaagctaaaa tgagccatat tcaacgggaa acgtcttgct cgaggccgcg      4200
attaaattcc aacatggatg ctgatttata tgggtataaa tgggctcgcg ataatgtcgg      4260
gcaatcaggt gcgacaatct atcgattgta tgggaagccc gatgcgccag agttgtttct      4320
gaaacatggc aaaggtagcg ttgccaatga tgttacagat gagatggtca ggctaaactg      4380
gctgacggaa tttatgcctc ttccgaccat caagcatttt atccgtactc ctgatgatgc      4440
atggttactc accactgcga tccccgggaa acagcattc caggtattag aagaatatcc      4500
tgattcaggt gaaaatattg ttgatgcgct ggcagtgttc ctgcgccggt tgcattcgat      4560
tcctgtttgt aattgtccctt ttaacggcga tcgcgtattt cgtctcgctc aggcgcaatc      4620
acgaatgaat aacggtttgg ttggtgcgag tgattttgat gacgagcgta atggctggcc      4680
tgttgaacaa gtctggaaag aaatgcataa gcttttgcca ttctcaccgg attcagtcgt      4740
```

-continued

```
cactcatggt gatttctcac ttgataacct tattttttgac gaggggaaat taataggttg    4800
tattgatgtt ggacgagtcg gaatcgcaga ccgataccag gatcttgcca tcctatggaa    4860
ctgcctcggt gagttttctc cttcattaca gaaacggctt tttcaaaaat atggtattga    4920
taatcctgat atgaataaat tgcagtttca cttgatgctc gatgagtttt tctaatgagg    4980
gcccaaatgt aatcacctgg ctcaccttcg ggtgggcctt tctgcgttgc tggcgttttt    5040
ccataggctc cgcccccctg acgagcatca caaaaatcga tgctcaagtc agaggtggcg    5100
aaacccgaca ggactataaa gataccaggc gtttccccct ggaagctccc tcgtgcgctc    5160
tcctgttccg accctgccgc ttaccggata cctgtccgcc tttctccctt cgggaagcgt    5220
ggcgctttct catagctcac gctgtaggta tctcagttcg gtgtaggtcg ttcgctccaa    5280
gctgggctgt gtgcacgaac cccccgttca gcccgaccgc tgcgccttat ccggtaacta    5340
tcgtcttgag tccaacccgg taagacacga cttatcgcca ctggcagcag ccactggtaa    5400
caggattagc agagcgaggt atgtaggcgg tgctacagag ttcttgaagt ggtggcctaa    5460
ctacggctac actagaagaa cagtatttgg tatctgcgct ctgctgaagc cagttacctc    5520
ggaaaaagag ttggtagctc ttgatccggc aaacaaacca ccgctggtag cggtggtttt    5580
tttgtttgca agcagcagat tacgcgcaga aaaaaggat ctcaagaaga tcctttgatt    5640
ttctaccgaa gaaggcccca cccgtgaagg tgagccagtg agttgattgc agtccagtta    5700
cgctggagtc tgaggctcgt cctgaatgat atcaagcttg aattcgtt              5748
```

<210> SEQ ID NO 36
<211> LENGTH: 2818
<212> TYPE: DNA
<213> ORGANISM: Artificial Sequence
<220> FEATURE:
<223> OTHER INFORMATION: Plasmid pSMART-amnp-GFPuv

<400> SEQUENCE: 36

```
tgaggctcgt cctgaatgat atcaagcttg aattcgttag acagtcaacg cgcttgatag      60
cctggcgaag atcatccgat cttcgcctta cacttttgtt tcacatttct gtgacatact     120
atcggatgtg cggtaattgt atgtgtagga ggataatcta tggctagcaa aggagaagaa     180
cttttcacat ggctagcaaa ggagaagaac ttttcactgg agttgtccca attcttgttg     240
aattagatgg tgatgttaat gggcacaaat tttctgtcag tggagagggt gaaggtgatg     300
ctacatacgg aaagcttacc cttaaattta tttgcactac tggaaaacta cctgttccat     360
ggccaacact tgtcactact ttctcttatg gtgttcaatg cttttcccgt tatccggatc     420
atatgaaacg gcatgacttt ttcaagagtg ccatgcccga aggttatgta caggaacgca     480
ctatatcttt caaagatgac gggaactaca agacgcgtgc tgaagtcaag tttgaaggtg     540 ataccctttgt taatcgtatc gagttaaaag gtattgattt taaagaagat ggaaacattc     600
tcggacacaa actcgagtac aactataact cacacaatgt atacatcacg gcagacaaac     660
aaaagaatgg aatcaaagct aacttcaaaa ttcgccacaa cattgaagat ggatccgttc     720
aactagcaga ccattatcaa caaaatactc caattggcga tggccctgtc cttttaccag     780
acaaccatta cctgtcgaca caatctgccc tttcgaaaga tcccaacgaa aagcgtgacc     840
acatggtcct tcttgagttt gtaactgctg ctgggattac acatggcatg gatgagctct     900
acaaataatg aggatccccg gcttatcggt cagtttcacc tgatttacgt aaaaacccgc     960
ttcggcgggt ttttgctttt ggaggggcag aaagatgaat gactgtccac gacgctatac    1020
```

| | |
|---|---|
| ccaaaagaaa gacgaattct ctagatatcg ctcaatactg accatttaaa tcatacctga | 1080 |
| cctccatagc agaaagtcaa aagcctccga ccggaggctt ttgacttgat cggcacgtaa | 1140 |
| gaggttccaa cttttcaccat aatgaaataa gatcactacc gggcgtattt tttgagttat | 1200 |
| cgagattttc aggagctaag gaagctaaaa tgagccatat tcaacgggaa acgtcttgct | 1260 |
| cgaggccgcg attaaattcc aacatggatg ctgatttata tgggtataaa tgggctcgcg | 1320 |
| ataatgtcgg gcaatcaggt gcgacaatct atcgattgta tgggaagccc gatgcgccag | 1380 |
| agttgtttct gaaacatggc aaaggtagcg ttgccaatga tgttacagat gagatggtca | 1440 |
| ggctaaactg gctgacggaa tttatgcctc ttccgaccat caagcatttt atccgtactc | 1500 |
| ctgatgatgc atggttactc accactgcga tcccagggaa aacagcattc caggtattag | 1560 |
| aagaatatcc tgattcaggt gaaaatattg ttgatgcgct ggcagtgttc ctgcgccggt | 1620 |
| tgcattcgat tcctgtttgt aattgtcctt ttaacggcga tcgcgtattt cgtctcgctc | 1680 |
| aggcgcaatc acgaatgaat aacggtttgg ttggtgcgag tgattttgat gacgagcgta | 1740 |
| atggctggcc tgttgaacaa gtctggaaag aaatgcataa gcttttgcca ttctcaccgg | 1800 |
| attcagtcgt cactcatggt gatttctcac ttgataacct tatttttgac gaggggaaat | 1860 |
| taataggttg tattgatgtt ggacgagtcg gaatcgcaga ccgataccag gatcttgcca | 1920 |
| tcctatggaa ctgcctcggt gagttttctc cttcattaca gaaacggctt tttcaaaaat | 1980 |
| atggtattga taatcctgat atgaataaat tgcagtttca cttgatgctc gatgagtttt | 2040 |
| tctaatgagg gcccaaatgt aatcacctgg ctcaccttcg ggtgggcctt tctgcgttgc | 2100 |
| tggcgttttt ccataggctc cgcccccctg acgagcatca caaaaatcga tgctcaagtc | 2160 |
| agaggtggcg aaacccgaca ggactataaa gataccaggc gtttccccct ggaagctccc | 2220 |
| tcgtgcgctc tcctgttccg accctgccgc ttaccggata cctgtccgcc tttctccctt | 2280 |
| cgggaagcgt ggcgctttct catagctcac gctgtaggta tctcagttcg gtgtaggtcg | 2340 |
| ttcgctccaa gctgggctgt gtgcacgaac cccccgttca gcccgaccgc tgcgccttat | 2400 |
| ccggtaacta tcgtcttgag tccaacccgg taagacacga cttatcgcca ctggcagcag | 2460 |
| ccactggtaa caggattagc agagcgaggt atgtaggcgg tgctacagag ttcttgaagt | 2520 |
| ggtggcctaa ctacggctac actagaagaa cagtatttgg tatctgcgct ctgctgaagc | 2580 |
| cagttacctc ggaaaaagag ttggtagctc ttgatccggc aaacaaacca ccgctggtag | 2640 |
| cggtggtttt tttgtttgca agcagcagat tacgcgcaga aaaaaggat ctcaagaaga | 2700 |
| tcctttgatt ttctaccgaa gaaaggccca ccgtgaagg tgagccagtg agttgattgc | 2760 |
| agtccagtta cgctggagtc tgaggctcgt cctgaatgat atcaagcttg aattcgtt | 2818 |

<210> SEQ ID NO 37
<211> LENGTH: 2839
<212> TYPE: DNA
<213> ORGANISM: Artificial Sequence
<220> FEATURE:
<223> OTHER INFORMATION: Plasmid pSMART-phoAp-GFPuv

<400> SEQUENCE: 37

| | |
|---|---|
| tgaggctcgt cctgaatgat atcaagcttg aattcgttcg attacgtaaa gaagttattg | 60 |
| aagcatcctc gtcagtaaaa agttaatctt ttcaacagct gtcataaagt tgtcacggcc | 120 |
| gagacttata gtcgctttgt ttttattttt taatgtattt gtagtgtagg aggataatct | 180 |
| atggctagca aaggagaaga actttttcaca tggctagcaa aggagaagaa cttttcactg | 240 |
| gagttgtccc aattcttgtt gaattagatg gtgatgttaa tgggcacaaa ttttctgtca | 300 |

```
gtggagaggg tgaaggtgat gctacatacg gaaagcttac ccttaaattt atttgcacta    360
ctggaaaact acctgttcca tggccaacac ttgtcactac tttctcttat ggtgttcaat    420
gcttttcccg ttatccggat catatgaaac ggcatgactt tttcaagagt gccatgcccg    480
aaggttatgt acaggaacgc actatatctt caaagatga cgggaactac aagacgcgtg    540
ctgaagtcaa gtttgaaggt gatacccttg ttaatcgtat cgagttaaaa ggtattgatt    600
ttaaagaaga tggaaacatt ctcggacaca aactcgagta caactataac tcacacaatg    660
tatacatcac ggcagacaaa caaaagaatg gaatcaaagc taacttcaaa attcgccaca    720
acattgaaga tggatccgtt caactagcag accattatca acaaaatact ccaattggcg    780
atggccctgt ccttttacca gacaaccatt acctgtcgac acaatctgcc ctttcgaaag    840
atcccaacga aaagcgtgac cacatggtcc ttcttgagtt tgtaactgct gctgggatta    900
cacatggcat ggatgagctc tacaaataat gaggatcccc ggcttatcgg tcagtttcac    960
ctgatttacg taaaaacccg cttcggcggg ttttgctttt tggaggggca gaaagatgaa    1020
tgactgtcca cgacgctata cccaaaagaa agacgaattc tctagatatc gctcaatact    1080
gaccatttaa atcatacctg acctccatag cagaaagtca aaagcctccg accggaggct    1140
tttgacttga tcggcacgta agaggttcca actttcacca taatgaaata agatcactac    1200
cgggcgtatt ttttgagtta tcgagatttt caggagctaa ggaagctaaa atgagccata    1260
ttcaacggga aacgtcttgc tcgaggccgc gattaaattc aacatggat gctgatttat    1320 atgggtataa atgggctcgc gataatgtcg ggcaatcagg tgcgacaatc tatcgattgt    1380
atgggaagcc cgatgcgcca gagttgtttc tgaaacatgg caaaggtagc gttgccaatg    1440
atgttacaga tgagatggtc aggctaaact ggctgacgga atttatgcct cttccgacca    1500
tcaagcattt tatccgtact cctgatgatg catggttact caccactgcg atcccaggga    1560
aaacagcatt ccaggtatta gaagaatatc ctgattcagg tgaaaatatt gttgatgcgc    1620
tggcagtgtt cctgcgccgg ttgcattcga ttcctgtttg taattgtcct tttaacggcg    1680
atcgcgtatt tcgtctcgct caggcgcaat cacgaatgaa taacggtttg gttggtgcga    1740
gtgattttga tgacgagcgt aatggctggc ctgttgaaca agtctggaaa gaaatgcata    1800
agcttttgcc attctcaccg gattcagtcg tcactcatgg tgatttctca cttgataacc    1860 ttattttga cgaggggaaa ttaataggtt gtattgatgt tggacgagtc ggaatcgcag    1920
accgatacca ggatcttgcc atcctatgga actgcctcgg tgagttttct ccttcattac    1980
agaaacggct ttttcaaaaa tatggtattg ataatcctga tatgaataaa ttgcagtttc    2040
acttgatgct cgatgagttt ttctaatgag gcccaaatg taatcacctg gctcaccttc    2100
gggtgggcct ttctgcgttg ctggcgtttt tccataggct ccgcccccct gacgagcatc    2160
acaaaaatcg atgctcaagt cagaggtggc gaaacccgac aggactataa agataccagg    2220
cgtttccccc tggaagctcc ctcgtgcgct ctcctgttcc gaccctgccg cttaccggat    2280
acctgtccgc ctttctccct tcgggaagcg tggcgctttc tcatagctca cgctgtaggt    2340
atctcagttc ggtgtaggtc gttcgctcca agctgggctg tgtgcacgaa ccccccgttc    2400
agcccgaccg ctgcgcctta tccggtaact atcgtcttga gtccaacccg gtaagacacg    2460
acttatcgcc actggcagca gccactggta acaggattag cagagcgagg tatgtaggcg    2520
gtgctacaga gttcttgaag tggtggccta actacggcta cactagaaga acagtatttg    2580
gtatctgcgc tctgctgaag ccagttacct cggaaaaaga gttggtagct cttgatccgg    2640
```

```
caaacaaacc accgctggta gcggtggttt ttttgtttgc aagcagcaga ttacgcgcag    2700
aaaaaaagga tctcaagaag atcctttgat tttctaccga agaaaggccc acccgtgaag    2760
gtgagccagt gagttgattg cagtccagtt acgctggagt ctgaggctcg tcctgaatga    2820
tatcaagctt gaattcgtt                                                 2839

<210> SEQ ID NO 38
<211> LENGTH: 2819
<212> TYPE: DNA
<213> ORGANISM: Artificial Sequence
<220> FEATURE:
<223> OTHER INFORMATION: Plasmid pSMART-phoBp-GFPuv

<400> SEQUENCE: 38
tgaggctcgt cctgaatgat atcaagcttg aattcgttgc cacggaaatc aataacctga      60
agatatgtgc gacgagcttt tcataaatct gtcataaatc tgacgcataa tgacgtcgca     120
ttaatgatcg caacctattt attgtgtagg aggataatct atggctagca aggagaaga     180 acttttcaca tggctagcaa aggagaagaa cttttcactg gagttgtccc aattcttgtt    240
gaattagatg gtgatgttaa tgggcacaaa ttttctgtca gtggagaggg tgaaggtgat    300
gctacatacg gaaagcttac ccttaaattt atttgcacta ctggaaaact acctgttcca    360
tggccaacac ttgtcactac tttctcttat ggtgttcaat gcttttcccg ttatccggat    420
catatgaaac ggcatgactt tttcaagagt gccatgcccg aaggttatgt acaggaacgc    480
actatatctt tcaaagatga cgggaactac aagacgcgtg ctgaagtcaa gtttgaaggt    540
gatacccttg ttaatcgtat cgagttaaaa ggtattgatt ttaaagaaga tggaaacatt    600
ctcggacaca aactcgagta caactataac tcacacaatg tatacatcac ggcagacaaa    660
caaaagaatg gaatcaaagc taacttcaaa attcgccaca acattgaaga tggatccgtt    720
caactagcag accattatca acaaaatact ccaattggcg atggccctgt ccttttacca    780
gacaaccatt acctgtcgac acaatctgcc ctttcgaaag atcccaacga aaagcgtgac    840
cacatggtcc ttcttgagtt tgtaactgct gctgggatta cacatggcat ggatgagctc    900
tacaaataat gaggatcccc ggcttatcgg tcagtttcac ctgatttacg taaaaacccg    960
cttcggcggg ttttttgctt tggagggca gaaagatgaa tgactgtcca cgacgctata   1020
cccaaaagaa agacgaattc tctagatatc gctcaatact gaccatttaa atcatacctg   1080
acctccatag cagaaagtca aaagcctccg accggaggct tttgacttga tcggcacgta   1140
agaggttcca actttcacca taatgaaata agatcactac cgggcgtatt ttttgagtta   1200
tcgagatttt caggagctaa ggaagctaaa atgagccata ttcaacggga acgtcttgc    1260 tcgaggccgc gattaaattc caacatggat gctgatttat atgggtataa atgggctcgc   1320
gataatgtcg ggcaatcagg tgcgacaatc tatcgattgt atgggaagcc cgatgcgcca   1380
gagttgtttc tgaaacatgg caaaggtagc gttgccaatg atgttacaga tgagatggtc   1440
aggctaaact ggctgacgga atttatgcct cttccgacca tcaagcattt tatccgtact   1500
cctgatgatg catggttact caccactgcg atcccaggga aaacagcatt ccaggtatta   1560
gaagaatatc ctgattcagg tgaaaatatt gttgatgcgc tggcagtgtt cctgcgccgg   1620
ttgcattcga ttcctgtttg taattgtcct tttaacggcg atcgcgtatt tcgtctcgct   1680
caggcgcaat cacgaatgaa taacggtttg gttggtgcga gtgatttga tgacgagcgt   1740 aatggctggc ctgttgaaca gtctggaaa gaaatgcata agcttttgcc attctcaccg   1800
gattcagtcg tcactcatgg tgatttctca cttgataacc ttatttttga cgaggggaaa   1860
```

```
ttaataggtt gtattgatgt tggacgagtc ggaatcgcag accgatacca ggatcttgcc    1920
atcctatgga actgcctcgg tgagttttct ccttcattac agaaacggct ttttcaaaaa    1980
tatggtattg ataatcctga tatgaataaa ttgcagtttc acttgatgct cgatgagttt    2040
ttctaatgag ggcccaaatg taatcacctg gctcaccttc gggtgggcct ttctgcgttg    2100
ctggcgtttt tccataggct ccgcccccct gacgagcatc acaaaaatcg atgctcaagt    2160
cagaggtggc gaaacccgac aggactataa agataccagg cgtttccccc tggaagctcc    2220
ctcgtgcgct ctcctgttcc gaccctgccg cttaccggat acctgtccgc ctttctccct    2280
tcgggaagcg tggcgctttc tcatagctca cgctgtaggt atctcagttc ggtgtaggtc    2340
gttcgctcca agctgggctg tgtgcacgaa ccccccgttc agcccgaccg ctgcgcctta    2400
tccggtaact atcgtcttga gtccaacccg gtaagacacg acttatcgcc actggcagca    2460
gccactggta acaggattag cagagcgagg tatgtaggcg gtgctacaga gttcttgaag    2520
tggtggccta actacggcta cactagaaga acagtatttg gtatctgcgc tctgctgaag    2580
ccagttacct cggaaaaaga gttggtagct cttgatccgg caaacaaacc accgctggta    2640
gcggtggttt ttttgtttgc aagcagcaga ttacgcgcag aaaaaaagga tctcaagaag    2700
atcctttgat tttctaccga gaaaggccc accgtgaag gtgagccagt gagttgattg    2760
cagtccagtt acgctggagt ctgaggctcg tcctgaatga tatcaagctt gaattcgtt     2819
```

<210> SEQ ID NO 39
<211> LENGTH: 2880
<212> TYPE: DNA
<213> ORGANISM: Artificial Sequence
<220> FEATURE:
<223> OTHER INFORMATION: Plasmid pSMART-phoEp-GFPuv

<400> SEQUENCE: 39

```
tgaggctcgt cctgaatgat atcaagcttg aattcgttag catggcgttt tgttgcgcgg      60
gatcagcaag cctagcggca gttgtttacg cttttattac agatttaata aattaccaca    120
ttttaagaat attattaatc tgtaatatat ctttaacaat ctcaggttaa aactttcct     180 gttttcaacg ggactctccc gctggtgtag gaggataatc tatggctagc aaaggagaag    240 aactttcac atggctagca aggagaaga acttttcact ggagttgtcc caattcttgt     300
tgaattagat ggtgatgtta atgggcacaa attttctgtc agtggagagg gtgaaggtga    360
tgctacatac ggaaagctta cccttaaatt tatttgcact actggaaaac tacctgttcc    420
atggccaaca cttgtcacta cttcctctta tggtgttcaa tgcttttccc gttatccgga    480
tcatatgaaa cggcatgact ttttcaagag tgccatgccc gaaggttatg tacaggaacg    540
cactatatct ttcaaagatg acgggaacta caagacgcgt gctgaagtca gtttgaagg    600 tgataccctt gttaatcgta tcgagttaaa aggtattgat tttaagaag atggaaacat    660 tctcggacac aaactcgagt acaactataa ctcacacaat gtatacatca cggcagacaa    720
acaaaagaat ggaatcaaag ctaacttcaa aattcgccac aacattgaag atggatccgt    780
tcaactagca gaccattatc aacaaaatac tccaattggc gatggccctg tccttttacc    840
agacaaccat tacctgtcga cacaatctgc cctttcgaaa gatcccaacg aaaagcgtga    900
ccacatggtc cttcttgagt ttgtaactgc tgctgggatt acacatggca tggatgagct    960
ctacaaataa tgaggatccc cggcttatcg gtcagtttca cctgatttac gtaaaaaccc   1020
gcttcggcgg ttttttgctt ttggagggc agaaagatga atgactgtcc acgacgctat   1080
```

```
acccaaaaga aagacgaatt ctctagatat cgctcaatac tgaccattta aatcatacct   1140
gacctccata gcagaaagtc aaaagcctcc gaccggaggc ttttgacttg atcggcacgt   1200
aagaggttcc aactttcacc ataatgaaat aagatcacta ccgggcgtat ttttgagtt    1260 atcgagattt tcaggagcta aggaagctaa atgagccat attcaacggg aaacgtcttg    1320
ctcgaggccg cgattaaatt ccaacatgga tgctgattta tatgggtata atgggctcg    1380 cgataatgtc gggcaatcag gtgcgacaat ctatcgattg tatgggaagc ccgatgcgcc   1440
agagttgttt ctgaaacatg gcaaaggtag cgttgccaat gatgttacag atgagatggt   1500
caggctaaac tggctgacgg aatttatgcc tcttccgacc atcaagcatt ttatccgtac   1560
tcctgatgat gcatggttac tcaccactgc gatcccaggg aaaacagcat ccaggtatt    1620 agaagaatat cctgattcag gtgaaaatat tgttgatgcg ctggcagtgt tcctgcgccg   1680
gttgcattcg attcctgttt gtaattgtcc ttttaacggc gatcgcgtat ttcgtctcgc   1740
tcaggcgcaa tcacgaatga ataacggttt ggttggtgcg agtgattttg atgacgagcg   1800
taatggctgg cctgttgaac aagtctggaa agaaatgcat aagcttttgc cattctcacc   1860
ggattcagtc gtcactcatg gtgatttctc acttgataac cttattttg acgaggggaa    1920 attaataggt tgtattgatg ttggacgagt cggaatcgca gaccgatacc aggatcttgc   1980
catcctatgg aactgcctcg gtgagttttc tccttcatta cagaaacggc ttttcaaaa    2040 atatggtatt gataatcctg atatgaataa attgcagttt cacttgatgc tcgatgagtt   2100
tttctaatga gggcccaaat gtaatcacct ggctcacctt cgggtgggcc tttctgcgtt   2160
gctggcgttt ttccataggc tccgcccccc tgacgagcat cacaaaaatc gatgctcaag   2220
tcagaggtgg cgaaacccga caggactata agataccag gcgtttcccc ctggaagctc    2280
cctcgtgcgc tctcctgttc cgaccctgcc gcttaccgga tacctgtccg cctttctccc   2340
ttcgggaagc gtggcgcttt ctcatagctc acgctgtagg tatctcagtt cggtgtaggt   2400
cgttcgctcc aagctgggct gtgtgcacga accccccgtt cagcccgacc gctgcgcctt   2460
atccggtaac tatcgtcttg agtccaaccc ggtaagacac gacttatcgc cactggcagc   2520
agccactggt aacaggatta gcagagcgag gtatgtaggc ggtgctacag agttcttgaa   2580
gtggtggcct aactacggct acactagaag aacagtattt ggtatctgcg ctctgctgaa   2640
gccagttacc tcggaaaaag agttggtagc tcttgatccg gcaaacaaac caccgctggt   2700
agcggtggtt ttttgtttg caagcagcag attacgcgca gaaaaaaggg atctcaagaa    2760
gatcctttga ttttctaccg aagaaaggcc caccgtgaa ggtgagccag tgagttgatt    2820
gcagtccagt tacgctggag tctgaggctc gtcctgaatg atatcaagct tgaattcgtt   2880
```

<210> SEQ ID NO 40
<211> LENGTH: 2879
<212> TYPE: DNA
<213> ORGANISM: Artificial Sequence
<220> FEATURE:
<223> OTHER INFORMATION: Plasmid pSMART-phoHp-GFPuv

<400> SEQUENCE: 40

```
tgaggctcgt cctgaatgat atcaagcttg aattcgttaa tcctgctgaa agcacacagc     60
ttttttcatc actgtcatca ctctgtcatc tttccagtag aaactaatgt cactgaaatg    120 gtgtttata gttaaatata agtaaatata ttgttgcaat aaatgcgaga tctgttgtac      180
ttattaagta gcagcggaag ttcgtgtagg aggataatct atggctagca aaggagaaga   240
acttttcaca tggctagcaa aggagaagaa cttttcactg gagttgtccc aattcttgtt   300
```

```
gaattagatg gtgatgttaa tgggcacaaa ttttctgtca gtggagaggg tgaaggtgat      360
gctacatacg gaaagcttac ccttaaattt atttgcacta ctggaaaact acctgttcca      420
tggccaacac ttgtcactac tttctcttat ggtgttcaat gcttttcccg ttatccggat      480
catatgaaac ggcatgactt tttcaagagt gccatgcccg aaggttatgt acaggaacgc      540
actatatctt tcaaagatga cgggaactac aagacgcgtg ctgaagtcaa gtttgaaggt      600
gatacccttg ttaatcgtat cgagttaaaa ggtattgatt ttaaagaaga tggaaacatt      660
ctcggacaca aactcgagta caactataac tcacacaatg tatacatcac ggcagacaaa      720
caaaagaatg gaatcaaagc taacttcaaa attcgccaca acattgaaga tggatccgtt      780
caactagcag accattatca acaaaatact ccaattggcg atggccctgt cctttacca       840
gacaaccatt acctgtcgac acaatctgcc ctttcgaaag atcccaacga aaagcgtgac      900
cacatggtcc ttcttgagtt tgtaactgct gctgggatta cacatggcat ggatgagctc      960
tacaaataat gaggatcccc ggcttatcgg tcagtttcac ctgatttacg taaaaacccg     1020
cttcggcggg ttttgctttt tggaggggca gaaagatgaa tgactgtcca cgacgctata     1080
cccaaaagaa agacgaattc tctagatatc gctcaatact gaccatttaa atcatacctg     1140
acctccatag cagaaagtca aaagcctccg accggaggct tttgacttga tcggcacgta     1200
agaggttcca actttcacca taatgaaata agatacactac cggcgtatt ttttgagtta     1260
tcgagatttt caggagctaa ggaagctaaa atgagccata ttcaacggga aacgtcttgc     1320
tcgaggccgc gattaaattc caacatggat gctgatttat atgggtataa atgggctcgc     1380
gataatgtcg ggcaatcagg tgcgacaatc tatcgattgt atgggaagcc cgatgcgcca     1440
gagttgtttc tgaaacatgg caaaggtagc gttgccaatg atgttacaga tgagatggtc     1500
aggctaaact ggctgacgga atttatgcct cttccgacca tcaagcattt tatccgtact     1560
cctgatgatg catggttact caccactgcg atcccaggga aaacagcatt ccaggtatta     1620
gaagaatatc ctgattcagg tgaaaatatt gttgatgcgc tggcagtgtt cctgcgccgg     1680
ttgcattcga ttcctgtttg taattgtcct tttaacggcg atcgcgtatt tcgtctcgct     1740
caggcgcaat cacgaatgaa taacggtttg gttggtgcga gtgattttga tgacgagcgt     1800
aatggctggc ctgttgaaca agtctggaaa gaaatgcata agcttttgcc attctcaccg     1860
gattcagtcg tcactcatgg tgatttctca cttgataacc ttattttga cgaggggaaa      1920
ttaataggtt gtattgatgt tggacgagtc ggaatcgcag accgatacca ggatcttgcc     1980
atcctatgga actgcctcgg tgagttttct ccttcattac agaaacggct ttttcaaaaa     2040
tatggtattg ataatcctga tatgaataaa ttgcagtttc acttgatgct cgatgagttt     2100
ttctaatgag gcccaaatg taatcacctg gctcaccttc gggtgggcct ttctgcgttg      2160
ctggcgtttt tccataggct ccgcccccct gacgagcatc acaaaaatcg atgctcaagt     2220
cagaggtggc gaaacccgac aggactataa agataccagg cgtttccccc tggaagctcc     2280
ctcgtgcgct ctcctgttcc gaccctgccg cttaccggat acctgtccgc ctttctccct     2340
tcgggaagcg tggcgctttc tcatagctca cgctgtaggt atctcagttc ggtgtaggtc     2400
gttcgctcca agctgggctg tgtgcacgaa ccccccgttc agcccgaccg ctgcgcctta     2460
tccggtaact atcgtcttga gtccaacccg gtaagacacg acttatcgcc actggcagca     2520
gccactggta acaggattag cagagcgagg tatgtaggcg gtgctacaga gttcttgaag     2580
tggtggccta actacggcta cactagaaga acagtatttg gtatctgcgc tctgctgaag     2640
```

```
ccagttacct cggaaaaaga gttggtagct cttgatccgg caaacaaacc accgctggta    2700
gcggtggttt ttttgtttgc aagcagcaga ttacgcgcag aaaaaaagga tctcaagaag    2760
atcctttgat tttctaccga agaaaggccc acccgtgaag gtgagccagt gagttgattg    2820
cagtccagtt acgctggagt ctgaggctcg tcctgaatga tatcaagctt gaattcgtt     2879
```

<210> SEQ ID NO 41
<211> LENGTH: 2850
<212> TYPE: DNA
<213> ORGANISM: Artificial Sequence
<220> FEATURE:
<223> OTHER INFORMATION: Plasmid pSMART-phoUp-GFPuv

<400> SEQUENCE: 41

```
tgaggctcgt cctgaatgat atcaagcttg aattcgttac cgaactgaag caggattaca     60
ccgtggtgat cgtcacccac aacatgcagc aggctgcgcg ttgttccgac cacacggcgt    120
ttatgtacct gggcgaattg attgagttca gcaacacgga cgatctgttc accagtgtag    180
gaggataatc tatggctagc aaaggagaag aacttttcac atggctagca aaggagaaga    240
acttttcact ggagttgtcc caattcttgt tgaattagat ggtgatgtta atgggcacaa    300
attttctgtc agtggagagg gtgaaggtga tgctacatac ggaaagctta cccttaaatt    360
tatttgcact actggaaaac tacctgttcc atggccaaca cttgtcacta ctttctctta    420
tggtgttcaa tgcttttccc gttatccgga tcatatgaaa cggcatgact ttttcaagag    480
tgccatgccc gaaggttatg tacaggaacg cactatatct ttcaaagatg acgggaacta    540
caagacgcgt gctgaagtca gtttgaaggt gatacccttg ttaatcgta tcgagttaaa    600 aggtattgat tttaaagaag atggaaacat tctcggacac aaactcgagt acaactataa    660
ctcacacaat gtatacatca cggcagacaa acaaaagaat ggaatcaaag ctaacttcaa    720
aattcgccac aacattgaag atggatccgt tcaactagca gaccattatc aacaaaatac    780
tccaattggc gatggccctg tccttttacc agacaaccat tacctgtcga cacaatctgc    840
cctttcgaaa gatcccaacg aaaagcgtga ccacatggtc cttcttgagt ttgtaactgc    900
tgctgggatt acacatggca tggatgagct ctacaaataa tgaggatccc ggcttatcg     960 gtcagtttca cctgatttac gtaaaaaccc gcttcggcgg ttttttgctt ttggagggc   1020 agaaagatga atgactgtcc acgacgctat acccaaaaga aagacgaatt ctctagatat   1080
cgctcaatac tgaccattta atcatacct gacctccata gcagaaagtc aaaagcctcc   1140
gaccggaggc ttttgacttg atcggcacgt aagaggttcc aactttcacc ataatgaaat   1200
aagatcacta ccgggcgtat ttttgagtt atcgagattt tcaggagcta aggaagctaa   1260
aatgagccat attcaacggg aaacgtcttg ctcgaggccg cgattaaatt ccaacatgga   1320
tgctgattta tatgggtata atgggctcg cgataatgtc gggcaatcag gtgcgacaat   1380
ctatcgattg tatgggaagc ccgatgcgcc agagttgttt ctgaaacatg gcaaaggtag   1440
cgttgccaat gatgttacag atgagatggt caggctaaac tggctgacgg aatttatgcc   1500
tcttccgacc atcaagcatt ttatccgtac tcctgatgat gcatggttac tcaccactgc   1560
gatcccaggg aaaacagcat tccaggtatt agaagaatat cctgattcag gtgaaaatat   1620
tgttgatgcg ctggcagtgt tcctgcgccg gttgcattcg attcctgttt gtaattgtcc   1680
ttttaacggc gatcgcgtat ttcgtctcgc tcaggcgcaa tcacgaatga ataacggttt   1740
ggttggtgcg agtgatttg atgacgagcg taatggctgg cctgttgaac aagtctggaa   1800
agaaatgcat aagcttttgc cattctcacc ggattcagtc gtcactcatg gtgatttctc   1860
```

```
acttgataac cttattttg acgaggggaa attaataggt tgtattgatg ttggacgagt      1920
cggaatcgca gaccgatacc aggatcttgc catcctatgg aactgcctcg gtgagttttc      1980
tccttcatta cagaaacggc tttttcaaaa atatggtatt gataatcctg atatgaataa      2040
attgcagttt cacttgatgc tcgatgagtt tttctaatga gggcccaaat gtaatcacct      2100
ggctcacctt cgggtgggcc tttctgcgtt gctggcgttt ttccataggc tccgcccccc      2160
tgacgagcat cacaaaaatc gatgctcaag tcagaggtgg cgaaacccga caggactata      2220
aagataccag gcgtttcccc ctggaagctc cctcgtgcgc tctcctgttc cgaccctgcc      2280
gcttaccgga tacctgtccg cctttctccc ttcgggaagc gtggcgcttt ctcatagctc      2340
acgctgtagg tatctcagtt cggtgtaggt cgttcgctcc aagctgggct gtgtgcacga      2400
accccccgtt cagcccgacc gctgcgcctt atccggtaac tatcgtcttg agtccaaccc      2460
ggtaagacac gacttatcgc cactggcagc agccactggt aacaggatta gcagagcgag      2520
gtatgtaggc ggtgctacag agttcttgaa gtggtggcct aactacggct acactagaag      2580
aacagtattt ggtatctgcg ctctgctgaa gccagttacc tcggaaaaag agttggtagc      2640
tcttgatccg gcaaacaaac caccgctggt agcggtggtt ttttgtttg caagcagcag      2700
attacgcgca gaaaaaaagg atctcaagaa gatcctttga ttttctaccg aagaaggcc      2760
cacccgtgaa ggtgagccag tgagttgatt gcagtccagt tacgctggag tctgaggctc      2820
gtcctgaatg atatcaagct tgaattcgtt                                       2850
```

<210> SEQ ID NO 42
<211> LENGTH: 2900
<212> TYPE: DNA
<213> ORGANISM: Artificial Sequence
<220> FEATURE:
<223> OTHER INFORMATION: Plasmid pSMART-mipAp-GFPuv

<400> SEQUENCE: 42

```
tgaggctcgt cctgaatgat atcaagcttg aattcgttca tccataaatt ttgcataatt       60
aatgtaaaga ccaggctcgc cagtaacgct aaattcattt ggctgtaagc gcggtgtcat      120
ccgcgtcagg aaaattaaac agttacttta aaaaatgaaa acgtaaaaag gttgggtttc      180
gatgtattga cgggtaaact ttgtcgcccg ctaaacattt gtttgtgtag gaggataatc      240
tatggctagc aaaggagaag aacttttcac atggctagca aaggagaaga acttttcact      300
ggagttgtcc caattcttgt tgaattagat ggtgatgtta atgggcacaa attttctgtc      360
agtggagagg gtgaaggtga tgctacatac ggaaagctta cccttaaatt tatttgcact      420
actggaaaac tacctgttcc atggccaaca cttgtcacta ctttctctta tggtgttcaa      480
tgcttttccc gttatccgga tcatatgaaa cggcatgact ttttcaagag tgccatgccc      540
gaaggttatg tacaggaacg cactatatct ttcaaagatg acgggaacta caagacgcgt      600
gctgaagtca gtttgaagg tgatacccct gttaatcgta tcgagttaaa aggtattgat      660
tttaaagaag atggaaacat tctcggacac aaactcgagt acaactataa ctcacacaat      720
gtatacatca cggcagacaa acaaaagaat ggaatcaaag ctaacttcaa aattcgccac      780
aacattgaag atggatccgt tcaactagca gaccattatc aacaaaatac tccaattggc      840
gatggccctg tccttttacc agacaaccat tacctgtcga cacaatctgc cctttcgaaa      900
gatcccaacg aaaagcgtga ccacatggtc cttcttgagt ttgtaactgc tgctgggatt      960
acacatggca tggatgagct ctacaaataa tgaggatccc cggcttatcg gtcagtttca     1020
```

```
cctgatttac gtaaaaaccc gcttcggcgg ttttttgctt ttggagggc agaaagatga    1080 atgactgtcc acgacgctat acccaaaaga aagacgaatt ctctagatat cgctcaatac    1140
tgaccattta aatcatacct gacctccata gcagaaagtc aaaagcctcc gaccggaggc    1200
ttttgacttg atcggcacgt aagaggttcc aactttcacc ataatgaaat aagatcacta    1260
ccgggcgtat tttttgagtt atcgagattt tcaggagcta aggaagctaa aatgagccat    1320
attcaacggg aaacgtcttg ctcgaggccg cgattaaatt ccaacatgga tgctgattta    1380
tatgggtata aatgggctcg cgataatgtc gggcaatcag gtgcgacaat ctatcgattg    1440
tatgggaagc ccgatgcgcc agagttgttt ctgaaacatg gcaaaggtag cgttgccaat    1500
gatgttacag atgagatggt caggctaaac tggctgacgg aatttatgcc tcttccgacc    1560
atcaagcatt ttatccgtac tcctgatgat gcatggttac tcaccactgc gatcccaggg    1620
aaaacagcat tccaggtatt agaagaatat cctgattcag gtgaaaatat tgttgatgcg    1680
ctggcagtgt tcctgcgccg gttgcattcg attcctgttt gtaattgtcc ttttaacggc    1740
gatcgcgtat ttcgtctcgc tcaggcgcaa tcacgaatga ataacggttt ggttggtgcg    1800
agtgattttg atgacgagcg taatggctgg cctgttgaac aagtctggaa agaaatgcat    1860
aagcttttgc cattctcacc ggattcagtc gtcactcatg gtgatttctc acttgataac    1920 cttattttg acgaggggaa attaataggt tgtattgatg ttggacgagt cggaatcgca    1980
gaccgatacc aggatcttgc catcctatgg aactgcctcg gtgagttttc tccttcatta    2040
cagaaacggc tttttcaaaa atatggtatt gataatcctg atatgaataa attgcagttt    2100
cacttgatgc tcgatgagtt tttctaatga gggcccaaat gtaatcacct ggctcacctt    2160
cgggtgggcc tttctgcgtt gctggcgttt ttccataggc tccgccccc tgacgagcat    2220 cacaaaaatc gatgctcaag tcagaggtgg cgaaacccga caggactata agataccag    2280 gcgtttcccc ctggaagctc cctcgtgcgc tctcctgttc cgaccctgcc gcttaccgga    2340
tacctgtccg cctttctccc ttcgggaagc gtggcgcttt ctcatagctc acgctgtagg    2400
tatctcagtt cggtgtaggt cgttcgctcc aagctgggct gtgtgcacga accccccgtt    2460
cagcccgacc gctgcgcctt atccggtaac tatcgtcttg agtccaaccc ggtaagacac    2520
gacttatcgc cactggcagc agccactggt aacaggatta gcagagcgag gtatgtaggc    2580
ggtgctacag agttcttgaa gtggtggcct aactacggct acactagaag aacagtattt    2640
ggtatctgcg ctctgctgaa gccagttacc tcggaaaaag agttggtagc tcttgatccg    2700
gcaaacaaac caccgctggt agcggtggtt ttttgtttg caagcagcag attacgcgca    2760 gaaaaaagg atctcaagaa gatcctttga ttttctaccg aagaaaggcc cacccgtgaa    2820
ggtgagccag tgagttgatt gcagtccagt tacgctggag tctgaggctc gtcctgaatg    2880
atatcaagct tgaattcgtt                                                2900

<210> SEQ ID NO 43
<211> LENGTH: 2816
<212> TYPE: DNA
<213> ORGANISM: Artificial Sequence
<220> FEATURE:
<223> OTHER INFORMATION: Plasmid pSMART-pstSp-GFPuv

<400> SEQUENCE: 43
tgaggctcgt cctgaatgat atcaagcttg aattcgttaa gactttatct ctctgtcata     60
aaactgtcat attccttaca tataactgtc acctgttttgt cctattttgc ttctcgtagc    120
caacaaacaa tgctttatga gtgtaggagg ataatctatg gctagcaaag gagaagaact    180
```

```
tttcacatgg ctagcaaagg agaagaactt ttcactggag ttgtcccaat tcttgttgaa    240
ttagatggtg atgttaatgg gcacaaattt tctgtcagtg gagagggtga aggtgatgct    300
acatacggaa agcttaccct taaatttatt tgcactactg gaaaactacc tgttccatgg    360
ccaacacttg tcactacttt ctcttatggt gttcaatgct tttcccgtta tccggatcat    420
atgaaacggc atgactttt caagagtgcc atgcccgaag gttatgtaca ggaacgcact    480
atatctttca aagatgacgg gaactacaag acgcgtgctg aagtcaagtt tgaaggtgat    540 accctttgtta atcgtatcga gttaaaaggt attgattta agaagatgg aaacattctc    600 ggacacaaac tcgagtacaa ctataactca cacaatgtat acatcacggc agacaaacaa    660
aagaatggaa tcaaagctaa cttcaaaatt cgccacaaca ttgaagatgg atccgttcaa    720
ctagcagacc attatcaaca aaatactcca attggcgatg gccctgtcct tttaccagac    780
aaccattacc tgtcgacaca atctgccctt tcgaaagatc ccaacgaaaa gcgtgaccac    840
atggtccttc ttgagtttgt aactgctgct gggattacac atggcatgga tgagctctac    900
aaataatgag gatccccggc ttatcggtca gtttcacctg atttacgtaa aaacccgctt    960
cggcgggttt ttgcttttgg aggggcagaa agatgaatga ctgtccacga cgctataccc   1020
aaaagaaaga cgaattctct agatatcgct caatactgac catttaaatc atacctgacc   1080
tccatagcag aaagtcaaaa gcctccgacc ggaggctttt gacttgatcg gcacgtaaga   1140
ggttccaact ttcaccataa tgaaataaga tcactaccgg gcgtattttt tgagttatcg   1200
agattttcag gagctaagga agctaaaatg agccatattc aacgggaaac gtcttgctcg   1260
aggccgcgat taaattccaa catggatgct gatttatatg ggtataaatg gctcgcgat    1320 aatgtcgggc aatcaggtgc gacaatctat cgattgtatg ggaagcccga tgcgccagag   1380
ttgtttctga aacatggcaa aggtagcgtt gccaatgatg ttacagatga gatggtcagg   1440
ctaaactggc tgacggaatt tatgcctctt ccgaccatca agcattttat ccgtactcct   1500
gatgatgcat ggttactcac cactgcgatc ccagggaaaa cagcattcca ggtattagaa   1560
gaatatcctg attcaggtga aaatattgtt gatgcgctgg cagtgttcct gcgccggttg   1620
cattcgattc ctgtttgtaa ttgtcctttt aacggcgatc gcgtatttcg tctcgctcag   1680
gcgcaatcac gaatgaataa cggtttggtt ggtgcgagtg attttgatga cgagcgtaat   1740
ggctggcctg ttgaacaagt ctggaaagaa atgcataagc ttttgccatt ctcaccggat   1800
tcagtcgtca ctcatggtga tttctcactt gataacctta tttttgacga ggggaaatta   1860
ataggttgta ttgatgttgg acgagtcgga atcgcagacc gataccagga tcttgccatc   1920
ctatggaact gcctcggtga gttttctcct tcattacaga acggcttttt caaaaatat    1980 ggtattgata atcctgatat gaataaattg cagtttcact tgatgctcga tgagtttttc   2040
taatgagggc ccaaatgtaa tcacctggct caccttcggg tgggcctttc tgcgttgctg   2100
gcgtttttcc ataggctccg ccccctgac gagcatcaca aaaatcgatg ctcaagtcag    2160
aggtggcgaa acccgacagg actataaaga taccaggcgt ttccccctgg aagctccctc   2220
gtgcgctctc ctgttccgac cctgccgctt accggatacc tgtccgcctt tctcccttcg   2280
ggaagcgtgg cgctttctca tagctcacgc tgtaggtatc tcagttcggt gtaggtcgtt   2340
cgctccaagc tgggctgtgt gcacgaaccc cccgttcagc ccgaccgctg cgccttatcc   2400
ggtaactatc gtcttgagtc caacccggta agacacgact tatcgccact ggcagcagcc   2460
actggtaaca ggattagcag agcgaggtat gtaggcggtg ctacagagtt cttgaagtgg   2520
```

```
tggcctaact acggctacac tagaagaaca gtatttggta tctgcgctct gctgaagcca    2580
gttacctcgg aaaaagagtt ggtagctctt gatccggcaa acaaaccacc gctggtagcg    2640
gtggtttttt tgtttgcaag cagcagatta cgcgcagaaa aaaggatct caagaagatc    2700 ctttgatttt ctaccgaaga aaggcccacc cgtgaaggtg agccagtgag ttgattgcag    2760
tccagttacg ctggagtctg aggctcgtcc tgaatgatat caagcttgaa ttcgtt       2816

<210> SEQ ID NO 44
<211> LENGTH: 2808
<212> TYPE: DNA
<213> ORGANISM: Artificial Sequence
<220> FEATURE:
<223> OTHER INFORMATION: Plasmid pSMART-ugpBp-GFPuv

<400> SEQUENCE: 44
tgaggctcgt cctgaatgat atcaagcttg aattcgtttc tttctgacac cttactatct      60
tacaaatgta acaaaaaagt tattttttctg taattcgagc atgtcatgtt accccgcgag    120
cataaaacgc gtgtgtagga ggataatcta tggctagcaa aggagaagaa cttttcacat    180
ggctagcaaa ggagaagaac ttttcactgg agttgtccca attcttgttg aattagatgg    240
tgatgttaat gggcacaaat tttctgtcag tggagagggt gaaggtgatg ctacatacgg    300
aaagcttacc cttaaattta tttgcactac tggaaaacta cctgttccat ggccaacact    360
tgtcactact ttctcttatg gtgttcaatg cttttcccgt tatccggatc atatgaaacg    420
gcatgacttt ttcaagagtg ccatgcccga aggttatgta caggaacgca ctatatcttt    480
caaagatgac gggaactaca agacgcgtgc tgaagtcaag tttgaaggtg ataccctggt    540
taatcgtatc gagttaaaag gtattgattt taaagaagat ggaaacattc tcggacacaa    600
actcgagtac aactataact cacacaatgt atacatcacg gcagacaaac aaaagaatgg    660
aatcaaagct aacttcaaaa ttcgccacaa cattgaagat ggatccgttc aactagcaga    720
ccattatcaa caaaatactc caattggcga tggccctgtc cttttaccag acaaccatta    780
cctgtcgaca caatctgccc tttcgaaaga tcccaacgaa aagcgtgacc acatggtcct    840
tcttgagttt gtaactgctg ctgggattac acatggcatg gatgagctct acaaataatg    900
aggatccccg gcttatcggt cagtttcacc tgatttacgt aaaaacccgc ttcggcgggt    960
ttttgctttt ggaggggcag aaagatgaat gactgtccac gacgctatac ccaaaagaaa   1020
gacgaattct ctagatatcg ctcaatactg accatttaaa tcatacctga cctccatagc   1080
agaaagtcaa aagcctccga ccggaggctt ttgacttgat cggcacgtaa gaggttccaa   1140
cttttaccat aatgaaataa gatcactacc gggcgtattt tttgagttat cgagattttc   1200
aggagctaag gaagctaaaa tgagccatat tcaacgggaa acgtcttgct cgaggccgcg   1260
attaaattcc aacatggatg ctgatttata tgggtataaa tgggctcgcg ataatgtcgg   1320
gcaatcaggt gcgacaatct atcgattgta tgggaagccc gatgcgccag agttgtttct   1380
gaaacatggc aaaggtagcg ttgccaatga tgttacagat gagatggtca ggctaaactg   1440
gctgacggaa tttatgcctc ttccgaccat caagcatttt atccgtactc ctgatgatgc   1500
atggttactc accactgcga tccccgggga acagcattc aggtattag aagaatatcc   1560 tgattcaggt gaaaatattg ttgatgcgct ggcagtgttc ctgcgccggt tgcattcgat   1620
tcctgtttgt aattgtcctt ttaacggcga tcgcgtattt cgtctcgctc aggcgcaatc   1680
acgaatgaat aacggtttgg ttggtgcgag tgattttgat gacgagcgta atggctggcc   1740
tgttgaacaa gtctggaaag aaatgcataa gcttttgcca ttctcaccgg attcagtcgt   1800
```

```
cactcatggt gatttctcac ttgataacct tattttgac gaggggaaat taataggttg    1860
tattgatgtt ggacgagtcg gaatcgcaga ccgataccag gatcttgcca tcctatggaa   1920
ctgcctcggt gagttttctc cttcattaca gaaacggctt tttcaaaaat atggtattga   1980
taatcctgat atgaataaat tgcagtttca cttgatgctc gatgagtttt tctaatgagg   2040
gcccaaatgt aatcacctgg ctcaccttcg ggtgggcctt tctgcgttgc tggcgttttt   2100
ccataggctc cgcccccctg acgagcatca caaaaatcga tgctcaagtc agaggtggcg   2160
aaacccgaca ggactataaa gataccaggc gtttccccct ggaagctccc tcgtgcgctc   2220
tcctgttccg accctgccgc ttaccggata cctgtccgcc tttctccctt cgggaagcgt   2280
ggcgctttct catagctcac gctgtaggta tctcagttcg gtgtaggtcg ttcgctccaa   2340
gctgggctgt gtgcacgaac cccccgttca gcccgaccgc tgcgccttat ccggtaacta   2400
tcgtcttgag tccaacccgg taagacacga cttatcgcca ctggcagcag ccactggtaa   2460
caggattagc agagcgaggt atgtaggcgg tgctacagag ttcttgaagt ggtggcctaa   2520
ctacggctac actagaagaa cagtatttgg tatctgcgct ctgctgaagc cagttacctc   2580
ggaaaaagag ttggtagctc ttgatccggc aaacaaacca ccgctggtag cggtggtttt   2640
tttgtttgca agcagcagat tacgcgcaga aaaaaggat ctcaagaaga tcctttgatt    2700
ttctaccgaa gaaaggccca cccgtgaagg tgagccagtg agttgattgc agtccagtta   2760
cgctggagtc tgaggctcgt cctgaatgat atcaagcttg aattcgtt               2808
```

<210> SEQ ID NO 45
<211> LENGTH: 2819
<212> TYPE: DNA
<213> ORGANISM: Artificial Sequence
<220> FEATURE:
<223> OTHER INFORMATION: Plasmid pSMART-ydfHp-GFPuv

<400> SEQUENCE: 45

```
tgaggctcgt cctgaatgat atcaagcttg aattcgttgc tatgccggac tgaatgtcca     60
ccgtcagtaa ttttatacc cggcgtaact gccgggttat tgcttgtcac aaaaaagtgg    120
tagactcatg cagttaactc actgtgtagg aggataatct atggctagca aggagaaga    180
acttttcaca tggctagcaa aggagaagaa cttttcactg gagttgtccc aattcttgtt   240
gaattagatg gtgatgttaa tgggcacaaa ttttctgtca gtggagaggg tgaaggtgat   300
gctacatacg gaaagcttac ccttaaattt atttgcacta ctggaaaact acctgttcca   360
tggccaacac ttgtcactac tttctcttat ggtgttcaat gctttccccg ttatccggat   420
catatgaaac ggcatgactt tttcaagagt gccatgcccg aaggttatgt acaggaacgc   480
actatatctt tcaaagatga cgggaactac aagacgcgtg ctgaagtcaa gtttgaaggt   540
gatacccttg ttaatcgtat cgagttaaaa ggtattgatt taaagaaga tggaaacatt   600
ctcggacaca aactcgagta caactataac tcacacaatg tatacatcac ggcagacaaa   660
caaaagaatg gaatcaaagc taacttcaaa attcgccaca cattgaaga tggatccgtt   720
caactagcag accattatca acaaaatact ccaattggcg atggccctgt ccttttacca   780
gacaaccatt acctgtcgac acaatctgcc ctttcgaaag atcccaacga aaagcgtgac   840
cacatggtcc ttcttgagtt tgtaactgct gctgggatta cacatggcat ggatgagctc   900
tacaaataat gaggatcccc ggcttatcgg tcagtttcac ctgatttacg taaaaacccg   960
cttcggcggg ttttgctttt tggaggggca gaaagatgaa tgactgtcca cgacgctata  1020
```

```
cccaaaagaa agacgaattc tctagatatc gctcaatact gaccatttaa atcatacctg    1080
acctccatag cagaaagtca aaagcctccg accggaggct tttgacttga tcggcacgta    1140
agaggttcca actttcacca taatgaaata agatcactac cgggcgtatt ttttgagtta    1200
tcgagatttt caggagctaa ggaagctaaa atgagccata ttcaacggga aacgtcttgc    1260
tcgaggccgc gattaaattc caacatggat gctgatttat atgggtataa atgggctcgc    1320
gataatgtcg ggcaatcagg tgcgacaatc tatcgattgt atgggaagcc cgatgcgcca    1380
gagttgtttc tgaaacatgg caaaggtagc gttgccaatg atgttacaga tgagatggtc    1440
aggctaaact ggctgacgga atttatgcct cttccgacca tcaagcattt tatccgtact    1500
cctgatgatg catggttact caccactgcg atcccaggga aaacagcatt ccaggtatta    1560
gaagaatatc ctgattcagg tgaaaatatt gttgatgcgc tggcagtgtt cctgcgccgg    1620
ttgcattcga ttcctgtttg taattgtcct tttaacggcg atcgcgtatt tcgtctcgct    1680
caggcgcaat cacgaatgaa taacggtttg gttggtgcga gtgattttga tgacgagcgt    1740
aatggctggc ctgttgaaca agtctggaaa gaaatgcata agcttttgcc attctcaccg    1800
gattcagtcg tcactcatgg tgatttctca cttgataacc ttattttga cgaggggaaa    1860
ttaataggtt gtattgatgt tggacgagtc ggaatcgcag accgatacca ggatcttgcc    1920
atcctatgga actgcctcgg tgagttttct ccttcattac agaaacggct ttttcaaaaa    1980
tatggtattg ataatcctga tatgaataaa ttgcagtttc acttgatgct cgatgagttt    2040
ttctaatgag ggcccaaatg taatcacctg gctcaccttc gggtgggcct ttctgcgttg    2100
ctggcgtttt tccataggct ccgcccccct gacgagcatc acaaaaatcg atgctcaagt    2160
cagaggtggc gaaacccgac aggactataa agataccagg cgtttccccc tggaagctcc    2220
ctcgtgcgct ctcctgttcc gaccctgccg cttaccggat acctgtccgc ctttctccct    2280
tcgggaagcg tggcgctttc tcatagctca cgctgtaggt atctcagttc ggtgtaggtc    2340
gttcgctcca agctgggctg tgtgcacgaa ccccccgttc agcccgaccg ctgcgcctta    2400
tccggtaact atcgtcttga gtccaacccg gtaagacacg acttatcgcc actggcagca    2460
gccactggta acaggattag cagagcgagg tatgtaggcg gtgctacaga gttcttgaag    2520
tggtggccta actacggcta cactagaaga acagtatttg gtatctgcgc tctgctgaag    2580
ccagttacct cggaaaaaga gttggtagct cttgatccgg caaacaaacc accgctggta    2640
gcggtggttt ttttgtttgc aagcagcaga ttacgcgcag aaaaaaagga tctcaagaag    2700
atcctttgat tttctaccga gaaaaggccc accgtgaag gtgagccagt gagttgattg    2760
cagtccagtt acgctggagt ctgaggctcg tcctgaatga tatcaagctt gaattcgtt    2819
```

<210> SEQ ID NO 46
<211> LENGTH: 3424
<212> TYPE: DNA
<213> ORGANISM: Artificial Sequence
<220> FEATURE:
<223> OTHER INFORMATION: Plasmid pSMART-Ala2

<400> SEQUENCE: 46

```
ccaggcatca ataaaacga aaggctcagt cgaaagactg gcctttcgt tttatctgtt      60
gtttgtcggt gaacgctctc tactagagtc acactggctc accttcgggt gggcctttct    120
gcgtttatac acagctaaca ccacgtcgtc cctatctgct gccctaggtc tatgagtggt    180
tgctggataa ctctttctga cccttacta tcttacaaat gtaacaaaaa agttatttt     240
ctgtaattcg agcatgtcat gttaccccgc gagcataaaa cgcgtatatt cagggagacc    300
```

```
acaacggttt ccctctacaa ataattttgt ttaactttgg aaaaaggaga tataccatga    360
tcattggggt gccgaaggag atcaaaaata atgagaaccg cgtcgcgttg accccgggag    420
gtgtcagcca gctgatctct aatggccatc gtgtcttagt tgaaacaggc gctggcctgg    480
gttctggctt cgaaaacgag gcctacgaat ctgcaggtgc ggaaattatt gctgatccaa    540
aacaggtctg ggatgcagag atggtcatga aagtgaaaga accgctcccg gaagaatatg    600
tctattttcg taaaggtctg gtgctgttta catatctgca tctggcagct gaaccggagc    660
tcgcacaagc ccttaaagat aaaggtgtca cggccatcgc atacgaaact gtcagcgaag    720
ggcgcacgct gccattactg accccgatgt cagaagtggc aggccgtatg gctgcgcaga    780
tcggcgcaca gtttcttgaa aaccaaaggg cgggaaggg tattctctta gcaggagtgc     840
cgggcgtcag tcgtgggaaa gtaactatta ttggtggcgg cgtggtagga acaaatgctg    900
ccaaaatggc cgtcggtttg ggggccgacg taacaatcat tgcgcgtaat gccgatcgcc    960
ttcgtcaatt agacgatatc tttggccacc aaatcaaaac cctgatttcg aacccagtca   1020
atatcgcgga tgcggtggcg gaagctgatt tgttgatctg cgccgtgtta attccgggag   1080
cgaaagcacc tacattggtg acggaagaaa tggtgaaaca aatgaaaccg ggttcagtca   1140
ttgttgatgt ggctattgat cagggtggca tcgtggaaac ggtggaccat attaccactc   1200
acgaccagcc gacgtatgaa aaacatggtg tcgtacacta tgcggtggcg aatatgcctg   1260
gtgcggtccc acgtacgagt acaatcgcac tgacaaatgt caccgtgccg tatgcgttgc   1320
aaatcgcgaa caaggtgcc gtgaaagcgc tggccgacaa tacggcgtta cgtgccggtc    1380
tgaacaccgc taacggtcac gtgacatatg aagcggtcgc gcgtgatttg gggtacgaat   1440
atgtaccggc ggaaaaagcc ttacaagacg aatcgagtgt cgctggtgca tagtaagctc   1500
ttctaatacg actcactata gggccggctt atcggtcagt ttcacctgat ttacgtaaaa   1560
acccgcttcg gcgggttttt gcttttggag gggcagaaag atgaatgact gtccacgacg   1620
ctatacccaa aagaaagacg aattctctag atatcgctca atactgacca tttaaatcat   1680
acctgacctc catagcagaa agtcaaaagc ctccgaccgg aggcttttga cttgatcggc   1740
acgtaagagg ttccaacttt caccataatg aaataagatc actaccgggc gtatttttg    1800
agttatcgag attttcagga gctaaggaag ctaaaatgag ccatattcaa cgggaaacgt   1860
cttgctcgag gccgcgatta aattccaaca tggatgctga tttatatggg tataaatggg   1920
ctcgcgataa tgtcgggcaa tcaggtgcga caatctatcg attgtatggg aagcccgatg   1980
cgccagagtt gtttctgaaa catggcaaag gtagcgttgc caatgatgtt acagatgaga   2040
tggtcaggct aaactggctg acggaattta tgcctcttcc gaccatcaag cattttatcc   2100
gtactcctga tgatgcatgg ttactcacca ctgcgatccc agggaaaaca gcattccagg   2160
tattagaaga atatcctgat tcaggtgaaa atattgttga tgcgctggca gtgttcctgc   2220
gccggttgca ttcgattcct gtttgtaatt gtccttttaa cggcgatcgc gtatttcgtc   2280
tcgctcaggc gcaatcacga atgaataacg gtttggttgg tgcgagtgat tttgatgacg   2340
agcgtaatgg ctggcctgtt gaacaagtct ggaaagaaat gcataagctt ttgccattct   2400
caccggattc agtcgtcact catggtgatt tctcacttga taaccttatt tttgacgagg   2460
ggaaattaat aggttgtatt gatgttggac gagtcggaat cgcagaccga taccaggatc   2520
ttgccatcct atggaactgc ctcggtgagt tttctccttc attacagaaa cggctttttc   2580
aaaaatatgg tattgataat cctgatatga ataaattgca gtttcacttg atgctcgatg   2640
```

-continued

```
agtttttcta atgagggccc aaatgtaatc acctggctca ccttcgggtg ggcctttctg   2700
cgttgctggc gttttttccat aggctccgcc ccctgacga gcatcacaaa aatcgatgct   2760
caagtcagag gtggcgaaac ccgacaggac tataaagata ccaggcgttt ccccctggaa   2820
gctccctcgt gcgctctcct gttccgaccc tgccgcttac cggatacctg tccgcctttc   2880
tcccttcggg aagcgtggcg cttctcata gctcacgctg taggtatctc agttcggtgt   2940
aggtcgttcg ctccaagctg ggctgtgtgc acgaaccccc cgttcagccc gaccgctgcg   3000
ccttatccgg taactatcgt cttgagtcca acccggtaag cacgactta tcgccactgg   3060
cagcagccac tggtaacagg attagcagag cgaggtatgt aggcggtgct acagagttct   3120
tgaagtggtg gcctaactac ggctacacta gaagaacagt atttggtatc tgcgctctgc   3180
tgaagccagt tacctcggaa aaagagttgg tagctcttga tccggcaaac aaaccaccgc   3240
tggtagcggt ggtttttttg tttgcaagca gcagattacg cgcagaaaaa aaggatctca   3300
agaagatcct ttgatttttct accgaagaaa ggcccaccccg tgaaggtgag ccagtgagtt   3360
gattgcagtc cagttacgct ggagtctgag gctcgtcctg aatgatatca agcttgaatt   3420
cgtt                                                               3424
```

<210> SEQ ID NO 47
<211> LENGTH: 21
<212> TYPE: DNA
<213> ORGANISM: Artificial Sequence
<220> FEATURE:
<223> OTHER INFORMATION: fabI T2 targeting sequence

<400> SEQUENCE: 47
cagcctgctc cggtcggacc g                                              21

<210> SEQ ID NO 48
<211> LENGTH: 45
<212> TYPE: DNA
<213> ORGANISM: Artificial Sequence
<220> FEATURE:
<223> OTHER INFORMATION: C-terminal DAS+4 tag

<400> SEQUENCE: 48
gcggccaacg atgaaaacta ttctgaaaac tatgcggatg cgtct                    45

<210> SEQ ID NO 49
<211> LENGTH: 59
<212> TYPE: DNA
<213> ORGANISM: Artificial Sequence
<220> FEATURE:
<223> OTHER INFORMATION: Primer gltA2-FOR

<400> SEQUENCE: 49
gggacagtta ttagttcgag ttccccgcgc cagcgggat aaaccgaaaa aaaaacccc      59

<210> SEQ ID NO 50
<211> LENGTH: 63
<212> TYPE: DNA
<213> ORGANISM: Artificial Sequence
<220> FEATURE:
<223> OTHER INFORMATION: Primer gltA2-REV

<400> SEQUENCE: 50
gaatgaattg gtcaatacgg tttatccccg ctggcgcggg gaactcgagg tggtaccaga    60
tct                                                                  63

```
<210> SEQ ID NO 51
<211> LENGTH: 28
<212> TYPE: DNA
<213> ORGANISM: Artificial Sequence
<220> FEATURE:
<223> OTHER INFORMATION: Primer G2U-FOR1

<400> SEQUENCE: 51
ccggatgagc attcatcagg cgggcaag                                              28

<210> SEQ ID NO 52
<211> LENGTH: 47
<212> TYPE: DNA
<213> ORGANISM: Artificial Sequence
<220> FEATURE:
<223> OTHER INFORMATION: Primer G2U-REV1

<400> SEQUENCE: 52
cggtttatcc ccgctggcgc ggggaactcg aacttcataa cttttac                         47

<210> SEQ ID NO 53
<211> LENGTH: 34
<212> TYPE: DNA
<213> ORGANISM: Artificial Sequence
<220> FEATURE:
<223> OTHER INFORMATION: Primer G2U-FOR2

<400> SEQUENCE: 53
gcgccagcgg ggataaaccg ttaccattct gttg                                       34

<210> SEQ ID NO 54
<211> LENGTH: 28
<212> TYPE: DNA
<213> ORGANISM: Artificial Sequence
<220> FEATURE:
<223> OTHER INFORMATION: Primer G2U-REV2

<400> SEQUENCE: 54
cttgcccgcc tgatgaatgc tcatccgg                                              28
```